(12) United States Patent
McClain et al.

(10) Patent No.: US 10,232,092 B2
(45) Date of Patent: Mar. 19, 2019

(54) STENTS AND OTHER DEVICES HAVING EXTRACELLULAR MATRIX COATING

(75) Inventors: James B. McClain, Raleigh, NC (US); Arthur J. Benvenuto, Durham, NC (US)

(73) Assignee: Micell Technologies, Inc., Durham, NC (US)

( * ) Notice: Subject to any disclaimer, the term of this patent is extended or adjusted under 35 U.S.C. 154(b) by 342 days.

(21) Appl. No.: 13/090,525

(22) Filed: Apr. 20, 2011

(65) Prior Publication Data

US 2011/0264190 A1     Oct. 27, 2011

Related U.S. Application Data

(60) Provisional application No. 61/326,956, filed on Apr. 22, 2010.

(51) Int. Cl.
| | | |
|---|---|---|
| *A61F 2/82* | (2013.01) |
| *A61L 31/16* | (2006.01) |
| *A61L 31/10* | (2006.01) |
| *A61L 31/14* | (2006.01) |
| *C09D 167/04* | (2006.01) |

(52) U.S. Cl.
CPC .............. *A61L 31/16* (2013.01); *A61L 31/10* (2013.01); *A61L 31/148* (2013.01); *C09D 167/04* (2013.01); *A61L 2300/30* (2013.01); *A61L 2300/62* (2013.01); *A61L 2420/02* (2013.01); *A61L 2420/08* (2013.01)

(58) Field of Classification Search
CPC ..................................................... A61F 2/82
USPC ....................................................... 623/1.42
See application file for complete search history.

(56) References Cited

U.S. PATENT DOCUMENTS

| | | |
|---|---|---|
| 3,087,860 A | 4/1963 | Endicott |
| 3,123,077 A | 3/1964 | Alcamo |
| 3,457,280 A | 7/1969 | Schmitt et al. |
| 3,597,449 A | 8/1971 | Deprospero et al. |

(Continued)

FOREIGN PATENT DOCUMENTS

| | | |
|---|---|---|
| CA | 2237466 A1 | 11/1998 |
| CA | 2589761 | 12/2004 |

(Continued)

OTHER PUBLICATIONS

Serruys, Patrick et al., Comparison of Coronary-Artery Bypass Surgery and Stenting for the Treatment of Multivessel Disease, N. Engl. J. Med., 2001, vol. 344, No. 15, pp. 1117-1124.

(Continued)

*Primary Examiner* — Matthew Schall
(74) *Attorney, Agent, or Firm* — Lerner, David, Littenberg, Krumholz & Mentlik, LLP

(57) ABSTRACT

Provided herein are devices comprising a stent; and a coating on said stent comprising a polymer and an active agent, wherein the active agent comprises at least one of: extracellular matrix and an extracellular matrix component. Provided herein are methods of preparing a device comprising a stent and a coating on said stent; said method comprising: providing a stent; and forming a plurality of layers on said stent; wherein the coating comprises a polymer and at least one of said layers comprises one or more active agents; wherein at least a portion of the active agent comprises at least one of extracellular matrix and an extracellular matrix component.

15 Claims, 2 Drawing Sheets

(56) References Cited

U.S. PATENT DOCUMENTS

| | | |
|---|---|---|
| 3,737,337 A | 6/1973 | Schnoring et al. |
| 3,773,919 A | 11/1973 | Boswell et al. |
| 3,929,992 A | 12/1975 | Sehgal et al. |
| 4,000,137 A | 12/1976 | Dvonch et al. |
| 4,188,373 A | 2/1980 | Krezanoski |
| 4,285,987 A | 8/1981 | Ayer et al. |
| 4,326,532 A | 4/1982 | Hammar |
| 4,336,381 A | 6/1982 | Nagata et al. |
| 4,389,330 A | 6/1983 | Tice et al. |
| 4,474,572 A | 10/1984 | McNaughton et al. |
| 4,474,751 A | 10/1984 | Haslam et al. |
| 4,478,822 A | 10/1984 | Haslam et al. |
| 4,530,840 A | 7/1985 | Tice et al. |
| 4,582,731 A | 4/1986 | Smith |
| 4,606,347 A | 8/1986 | Fogarty et al. |
| 4,617,751 A | 10/1986 | Johansson |
| 4,655,771 A | 4/1987 | Wallsten |
| 4,675,189 A | 6/1987 | Kent et al. |
| 4,733,665 A | 3/1988 | Palmaz |
| 4,734,227 A | 3/1988 | Smith |
| 4,734,451 A | 3/1988 | Smith |
| 4,758,435 A | 7/1988 | Schaaf |
| 4,762,593 A | 8/1988 | Youngner |
| 4,931,037 A | 6/1990 | Wetterman |
| 4,950,239 A | 8/1990 | Gahara |
| 4,985,625 A | 1/1991 | Hurst |
| 5,000,519 A | 3/1991 | Moore |
| 5,090,419 A | 2/1992 | Palestrant |
| 5,096,848 A | 3/1992 | Kawamura |
| 5,102,417 A | 4/1992 | Palmaz |
| 5,104,404 A | 4/1992 | Wolff |
| 5,106,650 A | 4/1992 | Hoy et al. |
| 5,125,570 A | 6/1992 | Jones |
| 5,158,986 A | 10/1992 | Cha et al. |
| 5,185,776 A | 2/1993 | Townsend |
| 5,195,969 A | 3/1993 | Wang et al. |
| 5,243,023 A | 9/1993 | Dezern |
| 5,270,086 A | 12/1993 | Hamlin |
| 5,288,711 A | 2/1994 | Mitchell et al. |
| 5,320,634 A | 6/1994 | Vigil et al. |
| 5,324,049 A | 6/1994 | Mistrater et al. |
| 5,340,614 A | 8/1994 | Perman et al. |
| 5,350,361 A | 9/1994 | Tsukashima et al. |
| 5,350,627 A | 9/1994 | Nemphos et al. |
| 5,342,621 A | 10/1994 | Eury |
| 5,356,433 A | 10/1994 | Rowland et al. |
| 5,360,403 A | 11/1994 | Mische |
| 5,362,718 A | 11/1994 | Skotnicki et al. |
| 5,366,504 A | 11/1994 | Andersen et al. |
| 5,368,045 A | 11/1994 | Clement et al. |
| 5,372,676 A | 12/1994 | Lowe |
| 5,385,776 A | 1/1995 | Maxfield et al. |
| 5,387,313 A | 2/1995 | Thoms |
| 5,403,347 A | 4/1995 | Roby et al. |
| 5,470,603 A | 11/1995 | Staniforth et al. |
| 5,494,620 A | 2/1996 | Liu et al. |
| 5,500,180 A | 3/1996 | Anderson et al. |
| 5,514,379 A | 5/1996 | Weissleder et al. |
| 5,545,208 A | 8/1996 | Wolff et al. |
| 5,556,383 A | 9/1996 | Wang et al. |
| 5,562,922 A | 10/1996 | Lambert |
| 5,569,463 A | 10/1996 | Helmus et al. |
| 5,570,537 A | 11/1996 | Black et al. |
| 5,578,709 A | 11/1996 | Woiszwillo |
| 5,599,576 A | 2/1997 | Opolski |
| 5,605,696 A | 2/1997 | Eury et al. |
| 5,607,442 A | 3/1997 | Fischell et al. |
| 5,609,629 A | 3/1997 | Fearnot et al. |
| 5,626,611 A | 5/1997 | Liu et al. |
| 5,626,862 A | 5/1997 | Brem et al. |
| 5,632,772 A | 5/1997 | Alcime et al. |
| 5,669,932 A | 9/1997 | Fischell et al. |
| 5,674,192 A | 10/1997 | Sahatjian et al. |
| 5,674,242 A | 10/1997 | Phan et al. |
| 5,725,570 A | 3/1998 | Heath |
| 5,733,303 A | 3/1998 | Israel et al. |
| 5,766,158 A | 6/1998 | Opolski |
| 5,800,511 A | 9/1998 | Mayer |
| 5,807,404 A | 9/1998 | Richter |
| 5,811,032 A | 9/1998 | Kawai et al. |
| 5,824,049 A | 10/1998 | Ragheb et al. |
| 5,837,313 A | 11/1998 | Ding et al. |
| 5,843,120 A | 12/1998 | Israel et al. |
| 5,871,436 A | 2/1999 | Eury |
| 5,873,904 A | 2/1999 | Ragheb et al. |
| 5,876,426 A | 3/1999 | Kume et al. |
| 5,876,452 A | 3/1999 | Athanasiou et al. |
| 5,913,895 A | 6/1999 | Burpee et al. |
| 5,924,631 A | 7/1999 | Rodrigues et al. |
| 5,948,020 A | 9/1999 | Yoon et al. |
| 5,957,975 A | 9/1999 | Lafont et al. |
| 5,981,568 A | 11/1999 | Kunz et al. |
| 5,981,719 A | 11/1999 | Woiszwillo et al. |
| 6,013,855 A | 1/2000 | McPherson et al. |
| 6,036,978 A | 3/2000 | Gombotz et al. |
| 6,039,721 A | 3/2000 | Johnson et al. |
| 6,068,656 A | 5/2000 | Von Oepen |
| 6,071,308 A | 6/2000 | Ballou et al. |
| 6,077,880 A | 6/2000 | Castillo et al. |
| 6,090,925 A | 7/2000 | Woiszwillo et al. |
| 6,129,755 A | 10/2000 | Mathis et al. |
| 6,143,037 A | 11/2000 | Goldsten et al. |
| 6,143,314 A | 11/2000 | Chandrashekar et al. |
| 6,146,356 A | 11/2000 | Wang et al. |
| 6,146,404 A | 11/2000 | Kim et al. |
| 6,153,252 A | 11/2000 | Hossainy et al. |
| 6,171,327 B1 | 1/2001 | Daniel et al. |
| 6,190,699 B1 | 2/2001 | Luzzi et al. |
| 6,193,744 B1 | 2/2001 | Ehr et al. |
| 6,206,914 B1 | 3/2001 | Soykan et al. |
| 6,217,608 B1 | 4/2001 | Penn et al. |
| 6,231,599 B1 | 5/2001 | Ley |
| 6,231,600 B1 | 5/2001 | Zhong et al. |
| 6,245,104 B1 | 6/2001 | Alt |
| 6,248,127 B1 | 6/2001 | Shah et al. |
| 6,248,129 B1 | 6/2001 | Froix |
| 6,251,980 B1 | 6/2001 | Lan et al. |
| 6,268,053 B1 | 7/2001 | Woiszwillo et al. |
| 6,273,913 B1 | 8/2001 | Wright et al. |
| 6,284,758 B1 | 9/2001 | Egi et al. |
| 6,299,635 B1 | 10/2001 | Frantzen |
| 6,309,669 B1 | 10/2001 | Setterstrom et al. |
| 6,319,541 B1 | 11/2001 | Pletcher et al. |
| 6,325,821 B1 | 12/2001 | Gaschino et al. |
| 6,336,934 B1 | 1/2002 | Gilson et al. |
| 6,342,062 B1 | 1/2002 | Suon et al. |
| 6,344,055 B1 | 2/2002 | Shukov |
| 6,355,691 B1 | 3/2002 | Goodman |
| 6,358,556 B1 | 3/2002 | Ding et al. |
| 6,361,819 B1 | 3/2002 | Tedeschi et al. |
| 6,362,718 B1 | 3/2002 | Patrick et al. |
| 6,364,903 B2 | 4/2002 | Tseng et al. |
| 6,368,658 B1 | 4/2002 | Schwartz et al. |
| 6,372,246 B1 | 4/2002 | Wei et al. |
| 6,387,121 B1 | 5/2002 | Alt |
| 6,409,716 B1 | 6/2002 | Sahatjian et al. |
| 6,414,050 B1 | 7/2002 | Howdle et al. |
| 6,416,779 B1 | 7/2002 | D-Augustine et al. |
| 6,448,315 B1 | 9/2002 | Lidgren et al. |
| 6,458,387 B1 | 10/2002 | Scott et al. |
| 6,461,380 B1 | 10/2002 | Cox |
| 6,461,644 B1 | 10/2002 | Jackson et al. |
| 6,488,703 B1 | 12/2002 | Kveen et al. |
| 6,495,163 B1 | 12/2002 | Jordan |
| 6,497,729 B1 | 12/2002 | Moussy et al. |
| 6,506,213 B1 | 1/2003 | Mandel et al. |
| 6,517,860 B1 | 2/2003 | Rosser et al. |
| 6,521,258 B1 | 2/2003 | Mandel et al. |
| 6,524,698 B1 | 2/2003 | Schmoock |
| 6,530,951 B1 | 3/2003 | Bates et al. |
| 6,537,310 B1 | 3/2003 | Palmaz et al. |
| 6,541,033 B1 | 4/2003 | Shah |
| 6,572,813 B1 | 6/2003 | Zhang et al. |
| 6,602,281 B1 | 8/2003 | Klein |

(56) References Cited

U.S. PATENT DOCUMENTS

| | | |
|---|---|---|
| 6,610,013 B1 | 8/2003 | Fenster et al. |
| 6,627,246 B2 | 9/2003 | Mehta et al. |
| 6,649,627 B1 | 11/2003 | Cecchi et al. |
| 6,660,176 B2 | 12/2003 | Tepper et al. |
| 6,669,785 B2 | 12/2003 | DeYoung et al. |
| 6,669,980 B2 | 12/2003 | Hanson et al. |
| 6,670,407 B2 | 12/2003 | Howdle et al. |
| 6,682,757 B1 | 1/2004 | Wright |
| 6,706,283 B1 | 3/2004 | Appel et al. |
| 6,710,059 B1 | 3/2004 | Labrie et al. |
| 6,720,003 B2 | 4/2004 | Cheng et al. |
| 6,723,913 B1 | 4/2004 | Barbetta |
| 6,726,712 B1 | 4/2004 | Raeder-Devens et al. |
| 6,736,996 B1 | 5/2004 | Carbonell et al. |
| 6,743,505 B2 | 6/2004 | Antall et al. |
| 6,749,902 B2 | 6/2004 | Yonker et al. |
| 6,755,871 B2 | 6/2004 | Damaso et al. |
| 6,756,084 B2 | 6/2004 | Fulton et al. |
| 6,767,558 B2 | 7/2004 | Wang et al. |
| 6,780,475 B2 | 8/2004 | Fulton et al. |
| 6,794,902 B2 | 9/2004 | Becker et al. |
| 6,800,663 B2 | 10/2004 | Asgarzadeh et al. |
| 6,815,218 B1 | 11/2004 | Jacobsen et al. |
| 6,821,549 B2 | 11/2004 | Jayaraman |
| 6,837,611 B2 | 1/2005 | Kuo et al. |
| 6,838,089 B1 | 1/2005 | Carlsson et al. |
| 6,838,528 B2 | 1/2005 | Zhou |
| 6,858,598 B1 | 2/2005 | McKearn et al. |
| 6,860,123 B1 | 3/2005 | Uhlin et al. |
| 6,868,123 B2 | 3/2005 | Bellas et al. |
| 6,884,377 B1 | 4/2005 | Burnham et al. |
| 6,884,823 B1 | 4/2005 | Pierick et al. |
| 6,897,205 B2 | 5/2005 | Beckert et al. |
| 6,905,555 B2 | 6/2005 | DeYoung et al. |
| 6,908,624 B2 | 6/2005 | Hossainy et al. |
| 6,916,800 B2 | 7/2005 | McKearn et al. |
| 6,923,979 B2 | 8/2005 | Fotland et al. |
| 6,936,270 B2 | 8/2005 | Watson et al. |
| 6,939,569 B1 | 9/2005 | Green et al. |
| 6,973,718 B2 | 12/2005 | Sheppard et al. |
| 7,056,591 B1 | 6/2006 | Pacetti et al. |
| 7,094,256 B1 | 8/2006 | Shah et al. |
| 7,148,201 B2 | 12/2006 | Stern et al. |
| 7,152,452 B2 | 12/2006 | Kokish |
| 7,160,592 B2 | 1/2007 | Rypacek et al. |
| 7,163,715 B1 | 1/2007 | Kramer |
| 7,169,404 B2 | 1/2007 | Hossainy et al. |
| 7,171,255 B2 | 1/2007 | Holupka et al. |
| 7,201,750 B1 | 4/2007 | Eggers et al. |
| 7,201,940 B1 | 4/2007 | Kramer |
| 7,229,837 B2 | 6/2007 | Chen |
| 7,278,174 B2 | 10/2007 | Villalobos |
| 7,279,174 B2 | 10/2007 | Pacetti et al. |
| 7,282,020 B2 | 10/2007 | Kaplan |
| 7,308,748 B2 | 12/2007 | Kokish |
| 7,323,454 B2 | 1/2008 | De Nijs et al. |
| 7,326,734 B2 | 2/2008 | Zi et al. |
| 7,329,383 B2 | 2/2008 | Stinson |
| 7,378,105 B2 | 5/2008 | Burke et al. |
| 7,419,696 B2 | 9/2008 | Berg et al. |
| 7,429,378 B2 | 9/2008 | Serhan et al. |
| 7,444,162 B2 | 10/2008 | Hassan |
| 7,455,658 B2 | 11/2008 | Wang |
| 7,455,688 B2 | 11/2008 | Furst et al. |
| 7,456,151 B2 | 11/2008 | Li et al. |
| 7,462,593 B2 | 12/2008 | Cuttitta et al. |
| 7,485,113 B2 | 2/2009 | Varner et al. |
| 7,498,042 B2 | 3/2009 | Igaki et al. |
| 7,524,865 B2 | 4/2009 | D'Amato et al. |
| 7,537,610 B2 | 5/2009 | Reiss |
| 7,537,785 B2 | 5/2009 | Loscalzo et al. |
| 7,553,827 B2 | 6/2009 | Attawia et al. |
| 7,713,538 B2 | 5/2010 | Lewis et al. |
| 7,727,275 B2 | 6/2010 | Betts et al. |
| 7,745,566 B2 | 6/2010 | Chattopadhyay et al. |
| 7,763,277 B1 | 7/2010 | Canham et al. |
| 7,771,468 B2 | 8/2010 | Whitbourne et al. |
| 7,837,726 B2 | 11/2010 | Von Oepen et al. |
| 7,842,312 B2 | 11/2010 | Burgermeister et al. |
| 7,919,108 B2 | 4/2011 | Rees et al. |
| 7,955,383 B2 | 6/2011 | Krivoruchko et al. |
| 7,967,855 B2 | 6/2011 | Furst et al. |
| 7,972,661 B2 | 7/2011 | Pui et al. |
| 8,070,796 B2 | 12/2011 | Furst et al. |
| 8,109,904 B1 | 2/2012 | Papp |
| 8,295,565 B2 | 10/2012 | Gu et al. |
| 8,298,565 B2 | 10/2012 | Taylor et al. |
| 8,377,356 B2 | 2/2013 | Huang |
| 8,535,372 B1 | 9/2013 | Fox et al. |
| 8,709,071 B1 | 4/2014 | Huang et al. |
| 8,753,659 B2 | 6/2014 | Lewis et al. |
| 8,753,709 B2 | 6/2014 | Hossainy et al. |
| 8,758,429 B2 | 6/2014 | Taylor et al. |
| 8,795,762 B2 | 8/2014 | Fulton et al. |
| 8,834,913 B2 | 9/2014 | Shaw et al. |
| 8,852,625 B2 | 10/2014 | DeYoung et al. |
| 8,900,651 B2 | 12/2014 | McClain et al. |
| 9,433,516 B2 | 9/2016 | McClain et al. |
| 9,486,431 B2 | 11/2016 | McClain et al. |
| 2001/0026804 A1 | 10/2001 | Boutignon |
| 2001/0034336 A1 | 10/2001 | Shah et al. |
| 2001/0037143 A1 | 11/2001 | Oepen |
| 2001/0044629 A1 | 11/2001 | Stinson |
| 2001/0049551 A1 | 12/2001 | Tseng et al. |
| 2002/0007209 A1 | 1/2002 | Scheerder et al. |
| 2002/0051485 A1 | 5/2002 | Bottomley |
| 2002/0051845 A1 | 5/2002 | Mehta et al. |
| 2002/0082680 A1 | 6/2002 | Shanley et al. |
| 2002/0091433 A1 | 7/2002 | Ding et al. |
| 2002/0099332 A1 | 7/2002 | Slepian et al. |
| 2002/0125860 A1 | 9/2002 | Schworn et al. |
| 2002/0133072 A1 | 9/2002 | Wang et al. |
| 2002/0144757 A1 | 10/2002 | Craig et al. |
| 2002/0151959 A1 | 10/2002 | Von Oepen |
| 2003/0001830 A1 | 1/2003 | Wampler et al. |
| 2003/0004563 A1 | 1/2003 | Jackson et al. |
| 2003/0028244 A1 | 2/2003 | Bates et al. |
| 2003/0031699 A1 | 2/2003 | Van Antwerp |
| 2003/0077200 A1 | 4/2003 | Charles et al. |
| 2003/0088307 A1* | 5/2003 | Shulze .................. A61F 2/91 623/1.15 |
| 2003/0125800 A1 | 7/2003 | Shulze et al. |
| 2003/0143315 A1 | 7/2003 | Pui et al. |
| 2003/0170305 A1 | 9/2003 | O'Neil et al. |
| 2003/0180376 A1 | 9/2003 | Dalal et al. |
| 2003/0185964 A1 | 10/2003 | Weber et al. |
| 2003/0204238 A1 | 10/2003 | Tedeschi |
| 2003/0209835 A1 | 11/2003 | Chun et al. |
| 2003/0222017 A1 | 12/2003 | Fulton et al. |
| 2003/0222018 A1 | 12/2003 | Yonker et al. |
| 2003/0232014 A1 | 12/2003 | Burke et al. |
| 2004/0013792 A1 | 1/2004 | Epstein et al. |
| 2004/0018228 A1 | 1/2004 | Fischell et al. |
| 2004/0022400 A1 | 2/2004 | Magrath |
| 2004/0022853 A1 | 2/2004 | Ashton et al. |
| 2004/0044397 A1 | 3/2004 | Stinson |
| 2004/0059290 A1 | 3/2004 | Palasis et al. |
| 2004/0096477 A1 | 5/2004 | Chauhan et al. |
| 2004/0102758 A1 | 5/2004 | Davila et al. |
| 2004/0106982 A1 | 6/2004 | Jalisi |
| 2004/0122205 A1 | 6/2004 | Nathan |
| 2004/0126542 A1 | 7/2004 | Fujiwara et al. |
| 2004/0143317 A1 | 7/2004 | Takashi et al. |
| 2004/0144317 A1 | 7/2004 | Chuman et al. |
| 2004/0147904 A1 | 7/2004 | Hung et al. |
| 2004/0157789 A1 | 8/2004 | Geall |
| 2004/0170685 A1 | 9/2004 | Carpenter et al. |
| 2004/0193177 A1 | 9/2004 | Houghton et al. |
| 2004/0193262 A1 | 9/2004 | Shadduck |
| 2004/0220660 A1 | 11/2004 | Shanley et al. |
| 2004/0224001 A1 | 11/2004 | Pacetti et al. |
| 2004/0236416 A1 | 11/2004 | Falotico |
| 2004/0260000 A1 | 12/2004 | Chaiko |
| 2005/0003074 A1 | 1/2005 | Brown et al. |

(56) References Cited

U.S. PATENT DOCUMENTS

| | | |
|---|---|---|
| 2005/0004661 A1 | 1/2005 | Lewis et al. |
| 2005/0010275 A1 | 1/2005 | Sahatjian et al. |
| 2005/0013872 A1 | 1/2005 | Freyman |
| 2005/0015046 A1 | 1/2005 | Weber et al. |
| 2005/0019747 A1 | 1/2005 | Anderson et al. |
| 2005/0033414 A1 | 2/2005 | Zhang et al. |
| 2005/0038498 A1 | 2/2005 | Dubrow et al. |
| 2005/0048121 A1 | 3/2005 | East et al. |
| 2005/0049694 A1 | 3/2005 | Neary |
| 2005/0060028 A1 | 3/2005 | Horres et al. |
| 2005/0069630 A1 | 3/2005 | Fox et al. |
| 2005/0070989 A1 | 3/2005 | Lye et al. |
| 2005/0070990 A1 | 3/2005 | Stinson |
| 2005/0070997 A1 | 3/2005 | Thornton et al. |
| 2005/0074479 A1 | 4/2005 | Weber et al. |
| 2005/0075714 A1 | 4/2005 | Cheng et al. |
| 2005/0079199 A1 | 4/2005 | Heruth et al. |
| 2005/0079274 A1 | 4/2005 | Palasis et al. |
| 2005/0084533 A1 | 4/2005 | Howdle et al. |
| 2005/0131008 A1 | 6/2005 | Betts et al. |
| 2005/0131513 A1 | 6/2005 | Myers et al. |
| 2005/0147734 A1 | 7/2005 | Seppala et al. |
| 2005/0159704 A1 | 7/2005 | Scott et al. |
| 2005/0166841 A1 | 8/2005 | Robida |
| 2005/0175772 A1 | 8/2005 | Worsham et al. |
| 2005/0177223 A1 | 8/2005 | Palmaz |
| 2005/0191491 A1 | 9/2005 | Wang et al. |
| 2005/0196424 A1 | 9/2005 | Chappa |
| 2005/0208102 A1 | 9/2005 | Schultz |
| 2005/0209244 A1 | 9/2005 | Prescott et al. |
| 2005/0209680 A1 | 9/2005 | Gale et al. |
| 2005/0216075 A1 | 9/2005 | Wang et al. |
| 2005/0220839 A1 | 10/2005 | DeWitt et al. |
| 2005/0222676 A1 | 10/2005 | Shanley et al. |
| 2005/0238829 A1 | 10/2005 | Motherwell et al. |
| 2005/0245637 A1 | 11/2005 | Hossainy et al. |
| 2005/0255327 A1 | 11/2005 | Chaney |
| 2005/0260186 A1 | 11/2005 | Bookbinder et al. |
| 2005/0268573 A1 | 12/2005 | Maxfield et al. |
| 2005/0288481 A1 | 12/2005 | Desnoyer et al. |
| 2005/0288629 A1 | 12/2005 | Kunis |
| 2006/0001011 A1 | 1/2006 | Wilson et al. |
| 2006/0002974 A1 | 1/2006 | Pacetti et al. |
| 2006/0020325 A1 | 1/2006 | Burgermeister et al. |
| 2006/0030652 A1 | 2/2006 | Adams et al. |
| 2006/0045901 A1 | 3/2006 | Weber |
| 2006/0067974 A1 | 3/2006 | Labrecque et al. |
| 2006/0073329 A1 | 4/2006 | Boyce et al. |
| 2006/0089705 A1 | 4/2006 | Ding et al. |
| 2006/0093771 A1 | 5/2006 | Rypacek et al. |
| 2006/0094744 A1 | 5/2006 | Maryanoff et al. |
| 2006/0104969 A1 | 5/2006 | Oray et al. |
| 2006/0106455 A1 | 5/2006 | Furst et al. |
| 2006/0116755 A1 | 6/2006 | Stinson |
| 2006/0121080 A1 | 6/2006 | Lye et al. |
| 2006/0121089 A1 | 6/2006 | Michal et al. |
| 2006/0134168 A1 | 6/2006 | Chappa et al. |
| 2006/0134211 A1 | 6/2006 | Lien et al. |
| 2006/0136041 A1 | 6/2006 | Schmid et al. |
| 2006/0147698 A1 | 7/2006 | Carroll et al. |
| 2006/0153729 A1 | 7/2006 | Stinson et al. |
| 2006/0160455 A1 | 7/2006 | Sugyo et al. |
| 2006/0188547 A1 | 8/2006 | Bezwada |
| 2006/0193886 A1 | 8/2006 | Owens et al. |
| 2006/0193890 A1 | 8/2006 | Owens et al. |
| 2006/0198868 A1 | 9/2006 | DeWitt et al. |
| 2006/0210638 A1 | 9/2006 | Liversidge et al. |
| 2006/0216324 A1 | 9/2006 | Stucke et al. |
| 2006/0222756 A1 | 10/2006 | Davila et al. |
| 2006/0228415 A1 | 10/2006 | Oberegger et al. |
| 2006/0228453 A1 | 10/2006 | Cromack et al. |
| 2006/0235506 A1 | 10/2006 | Ta et al. |
| 2006/0276877 A1 | 12/2006 | Owens et al. |
| 2006/0287611 A1 | 12/2006 | Fleming |
| 2007/0009564 A1 | 1/2007 | McClain et al. |
| 2007/0009664 A1 | 1/2007 | Fallais et al. |
| 2007/0026041 A1 | 2/2007 | DesNoyer et al. |
| 2007/0026042 A1 | 2/2007 | Narayanan |
| 2007/0032864 A1 | 2/2007 | Furst et al. |
| 2007/0038227 A1 | 2/2007 | Massicotte et al. |
| 2007/0038289 A1 | 2/2007 | Nishide et al. |
| 2007/0043434 A1 | 2/2007 | Meerkin et al. |
| 2007/0059350 A1 | 3/2007 | Kennedy et al. |
| 2007/0065478 A1 | 3/2007 | Hossainy |
| 2007/0110888 A1 | 5/2007 | Radhakrishnan et al. |
| 2007/0123973 A1 | 5/2007 | Roth et al. |
| 2007/0123977 A1 | 5/2007 | Cottone et al. |
| 2007/0128274 A1 | 6/2007 | Zhu et al. |
| 2007/0148251 A1 | 6/2007 | Hossainy et al. |
| 2007/0154513 A1 | 7/2007 | Atanasoska et al. |
| 2007/0154554 A1 | 7/2007 | Burgermeister et al. |
| 2007/0196242 A1 | 8/2007 | Boozer et al. |
| 2007/0196423 A1 | 8/2007 | Ruane et al. |
| 2007/0198081 A1 | 8/2007 | Castro et al. |
| 2007/0200268 A1 | 8/2007 | Dave |
| 2007/0203569 A1 | 8/2007 | Burgermeister et al. |
| 2007/0219579 A1* | 9/2007 | Paul, Jr. .................. A61F 2/013 606/200 |
| 2007/0225795 A1 | 9/2007 | Granada et al. |
| 2007/0250157 A1 | 10/2007 | Nishide et al. |
| 2007/0259017 A1 | 11/2007 | Francis |
| 2007/0280992 A1 | 12/2007 | Margaron et al. |
| 2008/0030066 A1 | 2/2008 | Mercier et al. |
| 2008/0051866 A1 | 2/2008 | Chen et al. |
| 2008/0065192 A1 | 3/2008 | Berglund |
| 2008/0071347 A1 | 3/2008 | Cambronne |
| 2008/0071358 A1 | 3/2008 | Weber et al. |
| 2008/0071359 A1 | 3/2008 | Thornton et al. |
| 2008/0075753 A1 | 3/2008 | Chappa |
| 2008/0077232 A1 | 3/2008 | Nishide |
| 2008/0085880 A1 | 4/2008 | Viswanath et al. |
| 2008/0091008 A1 | 4/2008 | Viswanath et al. |
| 2008/0095919 A1 | 4/2008 | McClain et al. |
| 2008/0097575 A1 | 4/2008 | Cottone |
| 2008/0097591 A1 | 4/2008 | Savage et al. |
| 2008/0098178 A1 | 4/2008 | Veazey et al. |
| 2008/0107702 A1 | 5/2008 | Jennissen |
| 2008/0118543 A1 | 5/2008 | Pacetti et al. |
| 2008/0124372 A1 | 5/2008 | Hossainy et al. |
| 2008/0138375 A1 | 6/2008 | Yan et al. |
| 2008/0206304 A1 | 8/2008 | Lindquist et al. |
| 2008/0213464 A1 | 9/2008 | O'Connor |
| 2008/0233267 A1 | 9/2008 | Berglund |
| 2008/0255510 A1 | 10/2008 | Wang |
| 2008/0269449 A1 | 10/2008 | Chattopadhyay et al. |
| 2008/0286325 A1 | 11/2008 | Reyes et al. |
| 2008/0292776 A1 | 11/2008 | Dias et al. |
| 2008/0300669 A1 | 12/2008 | Hossainy |
| 2008/0300689 A1 | 12/2008 | Hossainy |
| 2009/0043379 A1 | 2/2009 | Prescott |
| 2009/0062909 A1 | 3/2009 | Taylor et al. |
| 2009/0068266 A1 | 3/2009 | Raheja et al. |
| 2009/0076446 A1 | 3/2009 | Dubuclet et al. |
| 2009/0082855 A1 | 3/2009 | Borges et al. |
| 2009/0098178 A1 | 4/2009 | Hofmann et al. |
| 2009/0105687 A1 | 4/2009 | Deckman et al. |
| 2009/0105809 A1 | 4/2009 | Lee et al. |
| 2009/0110711 A1 | 4/2009 | Trollsas et al. |
| 2009/0111787 A1 | 4/2009 | Lim et al. |
| 2009/0123515 A1 | 5/2009 | Taylor et al. |
| 2009/0123521 A1 | 5/2009 | Weber et al. |
| 2009/0186069 A1 | 7/2009 | DeYoung et al. |
| 2009/0202609 A1 | 8/2009 | Keough et al. |
| 2009/0216317 A1 | 8/2009 | Cromack et al. |
| 2009/0227949 A1 | 9/2009 | Freyman et al. |
| 2009/0231578 A1 | 9/2009 | Ling et al. |
| 2009/0263460 A1 | 10/2009 | McDonald |
| 2009/0285974 A1 | 11/2009 | Kerrigan |
| 2009/0292351 A1 | 11/2009 | McClain et al. |
| 2009/0292776 A1 | 11/2009 | Nesbitt et al. |
| 2009/0297578 A1 | 12/2009 | Trollsas et al. |
| 2009/0300689 A1 | 12/2009 | Conte et al. |
| 2010/0000328 A1 | 1/2010 | Mahmoud |
| 2010/0006358 A1 | 1/2010 | Ishikawa |

(56) References Cited

U.S. PATENT DOCUMENTS

| | | | |
|---|---|---|---|
| 2010/0015200 A1 | 1/2010 | McClain et al. |
| 2010/0030261 A1 | 2/2010 | McClain et al. |
| 2010/0042206 A1 | 2/2010 | Yadav et al. |
| 2010/0055145 A1 | 3/2010 | Betts et al. |
| 2010/0055294 A1 | 3/2010 | Wang et al. |
| 2010/0063570 A1 | 3/2010 | Pacetti et al. |
| 2010/0063580 A1 | 3/2010 | McClain et al. |
| 2010/0074934 A1 | 3/2010 | Hunter |
| 2010/0131044 A1 | 5/2010 | Patel |
| 2010/0155496 A1 | 6/2010 | Stark et al. |
| 2010/0166869 A1 | 7/2010 | Desai et al. |
| 2010/0196482 A1 | 8/2010 | Radovic-Moreno et al. |
| 2010/0198330 A1 | 8/2010 | Hossainy et al. |
| 2010/0198331 A1 | 8/2010 | Rapoza et al. |
| 2010/0211164 A1 | 8/2010 | McClain et al. |
| 2010/0228348 A1 | 9/2010 | McClain et al. |
| 2010/0233332 A1 | 9/2010 | Xing et al. |
| 2010/0239635 A1 | 9/2010 | McClain et al. |
| 2010/0241220 A1 | 9/2010 | McClain et al. |
| 2010/0256746 A1 | 10/2010 | Taylor et al. |
| 2010/0256748 A1 | 10/2010 | Taylor et al. |
| 2010/0262224 A1 | 10/2010 | Kleiner |
| 2010/0272775 A1 | 10/2010 | Cleek et al. |
| 2010/0272778 A1 | 10/2010 | McClain et al. |
| 2010/0285085 A1 | 11/2010 | Stankus et al. |
| 2010/0298928 A1 | 11/2010 | McClain et al. |
| 2010/0305689 A1 | 12/2010 | Venkatraman et al. |
| 2011/0009953 A1 | 1/2011 | Luk et al. |
| 2011/0034422 A1 | 2/2011 | Kannan et al. |
| 2011/0060073 A1 | 3/2011 | Huang et al. |
| 2011/0159069 A1 | 6/2011 | Shaw et al. |
| 2011/0160751 A1 | 6/2011 | Granja |
| 2011/0172763 A1 | 7/2011 | Ndondo-Lay |
| 2011/0189299 A1 | 8/2011 | Okubo et al. |
| 2011/0190864 A1 | 8/2011 | McClain et al. |
| 2011/0223212 A1 | 9/2011 | Taton et al. |
| 2011/0238161 A1 | 9/2011 | Fulton et al. |
| 2011/0243884 A1 | 10/2011 | O'Shea et al. |
| 2011/0257732 A1 | 10/2011 | McClain et al. |
| 2011/0264190 A1 | 10/2011 | McClain et al. |
| 2011/0301697 A1 | 12/2011 | Hoffmann et al. |
| 2012/0064124 A1 | 3/2012 | McClain et al. |
| 2012/0064143 A1 | 3/2012 | Sharp et al. |
| 2012/0065723 A1 | 3/2012 | Drasler et al. |
| 2012/0101566 A1 | 4/2012 | Mews et al. |
| 2012/0150275 A1 | 6/2012 | Shaw-Klein |
| 2012/0160408 A1 | 6/2012 | Clerc et al. |
| 2012/0172787 A1 | 7/2012 | McClain et al. |
| 2012/0177742 A1 | 7/2012 | McClain et al. |
| 2012/0231037 A1 | 9/2012 | Levi et al. |
| 2012/0271396 A1 | 10/2012 | Zheng et al. |
| 2012/0280432 A1 | 11/2012 | Chen et al. |
| 2012/0290075 A1 | 11/2012 | Mortisen et al. |
| 2012/0323311 A1 | 12/2012 | McClain et al. |
| 2013/0006351 A1 | 1/2013 | Taylor et al. |
| 2013/0035754 A1 | 2/2013 | Shulze et al. |
| 2013/0087270 A1 | 4/2013 | Hossainy et al. |
| 2013/0172853 A1 | 7/2013 | McClain et al. |
| 2014/0343667 A1 | 11/2014 | McClain |
| 2014/0350522 A1 | 11/2014 | McClain et al. |
| 2014/0371717 A1 | 12/2014 | McClain et al. |
| 2015/0024116 A1 | 1/2015 | Matson et al. |
| 2015/0025620 A1 | 1/2015 | Taylor et al. |
| 2015/0250926 A1 | 9/2015 | McClain et al. |
| 2016/0095726 A1 | 4/2016 | McClain et al. |

FOREIGN PATENT DOCUMENTS

| | | | |
|---|---|---|---|
| CA | 2615452 A1 | 1/2007 |
| CA | 2650590 A1 | 11/2007 |
| CA | 2679712 A1 | 7/2008 |
| CA | 2684482 A1 | 10/2008 |
| CA | 2721832 A1 | 12/2009 |
| CN | 2423899 Y | 3/2001 |
| CN | 1465410 | 1/2004 |
| CN | 1575860 A | 2/2005 |
| CN | 1649551 | 8/2005 |
| CN | 1684641 A | 10/2005 |
| CN | 101161300 A | 4/2008 |
| CN | 102481195 A | 5/2012 |
| DE | 4336209 A1 | 3/1995 |
| DE | 29702671 U1 | 4/1997 |
| DE | 29716476 U1 | 12/1997 |
| DE | 19633901 A1 | 2/1998 |
| DE | 29716467 U1 | 2/1998 |
| DE | 19740506 A1 | 3/1998 |
| DE | 19754870 A1 | 8/1998 |
| DE | 19822157 A1 | 11/1999 |
| DE | 69611186 T2 | 5/2001 |
| EP | 0335341 | 10/1989 |
| EP | 0604022 | 6/1994 |
| EP | 800801 A1 | 10/1997 |
| EP | 0876806 A1 | 11/1998 |
| EP | 0982041 | 3/2000 |
| EP | 1195822 A2 | 4/2002 |
| EP | 1325758 A2 | 7/2003 |
| EP | 1327422 A1 | 7/2003 |
| EP | 1454677 | 9/2004 |
| EP | 1502655 A2 | 2/2005 |
| EP | 1909973 A2 | 4/2008 |
| EP | 2197070 A1 | 6/2010 |
| EP | 2293357 A1 | 3/2011 |
| EP | 2293366 A1 | 3/2011 |
| FR | 2758253 A1 | 7/1998 |
| JP | 1994-098902 | 4/1994 |
| JP | H06218063 A | 8/1994 |
| JP | H08206223 A | 8/1996 |
| JP | H09-056807 | 3/1997 |
| JP | H1029524 | 2/1998 |
| JP | H10151207 A | 6/1998 |
| JP | H10314313 A | 12/1998 |
| JP | H1157018 A | 3/1999 |
| JP | 2000316981 A | 11/2000 |
| JP | 2001521503 A | 11/2001 |
| JP | 2002239013 A | 8/2002 |
| JP | 2003-205037 | 7/2003 |
| JP | 2003-533286 | 11/2003 |
| JP | 2003-5339493 | 11/2003 |
| JP | 2003533492 | 11/2003 |
| JP | 2004512059 A | 4/2004 |
| JP | 2004/173770 | 6/2004 |
| JP | 2004-518458 | 6/2004 |
| JP | 2004-529674 | 9/2004 |
| JP | 2004528060 A | 9/2004 |
| JP | 2005-505318 | 2/2005 |
| JP | 2005168646 A | 6/2005 |
| JP | 2005519080 A | 6/2005 |
| JP | 2005-523119 | 8/2005 |
| JP | 2005-523332 | 8/2005 |
| JP | 2005-296690 | 10/2005 |
| JP | 2006506191 A | 2/2006 |
| JP | 2006512175 A | 4/2006 |
| JP | 2007502250 A | 2/2007 |
| JP | 2007215620 A | 8/2007 |
| JP | 2009-501566 | 1/2009 |
| JP | 2009529399 A | 8/2009 |
| JP | 2010052503 A | 3/2010 |
| JP | 2010515539 A | 5/2010 |
| JP | 2010516307 A | 5/2010 |
| JP | 2011517589 A | 6/2011 |
| JP | 2012527318 A | 11/2012 |
| JP | 2013153822 A | 8/2013 |
| KR | 10-2004-0034064 | 4/2004 |
| KR | 10-1231197 B1 | 2/2013 |
| WO | WO-2011/009096 A1 | 1/1920 |
| WO | 9409010 A1 | 4/1994 |
| WO | WO-95/006487 | 3/1995 |
| WO | 9616691 A1 | 6/1996 |
| WO | WO-96/20698 | 7/1996 |
| WO | 9632907 A1 | 10/1996 |
| WO | 9641807 A1 | 12/1996 |
| WO | WO-97/045502 | 12/1997 |
| WO | 9802441 A2 | 1/1998 |
| WO | 9908729 A1 | 2/1999 |

(56) References Cited

FOREIGN PATENT DOCUMENTS

| WO | 9915530 A1 | 4/1999 |
|---|---|---|
| WO | 9917680 A1 | 4/1999 |
| WO | 99016388 A1 | 4/1999 |
| WO | 0006051 A1 | 2/2000 |
| WO | 0025702 A1 | 5/2000 |
| WO | 00032238 A1 | 6/2000 |
| WO | 0114387 A1 | 3/2001 |
| WO | WO-2001/054662 | 8/2001 |
| WO | 0187345 A1 | 11/2001 |
| WO | 0187368 A1 | 11/2001 |
| WO | WO-2001-087371 | 11/2001 |
| WO | WO-2001/087372 | 11/2001 |
| WO | 0226281 A1 | 4/2002 |
| WO | WO-2002/040702 | 5/2002 |
| WO | WO 2002/043799 | 6/2002 |
| WO | 02055122 A1 | 7/2002 |
| WO | WO-2002-074194 A2 | 9/2002 |
| WO | WO-2002/090085 | 11/2002 |
| WO | 02100456 A1 | 12/2002 |
| WO | WO-2003/039553 | 5/2003 |
| WO | WO-2003-082368 A | 10/2003 |
| WO | 03090684 A2 | 11/2003 |
| WO | WO-2003/101624 A1 | 12/2003 |
| WO | WO-2004/009145 | 1/2004 |
| WO | 2004028406 A1 | 4/2004 |
| WO | WO-2004/028589 | 4/2004 |
| WO | WO-2004/043506 | 5/2004 |
| WO | WO-2004/045450 | 6/2004 |
| WO | WO-2004/098574 | 11/2004 |
| WO | 2005018696 A1 | 3/2005 |
| WO | WO-2005/042623 A1 | 5/2005 |
| WO | WO-2005/063319 | 7/2005 |
| WO | WO-2005/069889 | 8/2005 |
| WO | WO-2005/117942 A2 | 12/2005 |
| WO | WO-2006/014534 | 2/2006 |
| WO | WO-2006/052575 | 5/2006 |
| WO | 2006063430 A1 | 6/2006 |
| WO | WO-2006/065685 | 6/2006 |
| WO | WO-2006/083796 A2 | 8/2006 |
| WO | WO-2006/099276 A2 | 9/2006 |
| WO | 2007017707 A2 | 1/2007 |
| WO | 2007017708 A3 | 1/2007 |
| WO | WO-2007-002238 | 1/2007 |
| WO | WO-2007/011707 A2 | 1/2007 |
| WO | WO-2007/011708 A2 | 1/2007 |
| WO | WO-2007/092179 | 8/2007 |
| WO | 2007106441 A2 | 9/2007 |
| WO | WO-2007/127363 | 11/2007 |
| WO | WO 2007/143609 | 12/2007 |
| WO | 2008024626 A2 | 2/2008 |
| WO | WO-2008/042909 | 4/2008 |
| WO | WO-2008/046641 | 4/2008 |
| WO | WO-2008/046642 | 4/2008 |
| WO | WO-2008/052000 | 5/2008 |
| WO | WO-2008/070996 | 6/2008 |
| WO | WO 2008/086369 | 7/2008 |
| WO | WO 2008/131131 | 10/2008 |
| WO | WO-2008/0148013 | 12/2008 |
| WO | 09039553 A1 | 4/2009 |
| WO | 2009051614 A1 | 4/2009 |
| WO | WO-2009/051614 | 4/2009 |
| WO | WO-2009/051780 | 4/2009 |
| WO | 2009096822 A1 | 8/2009 |
| WO | 2009113605 A1 | 9/2009 |
| WO | 2009120361 A2 | 10/2009 |
| WO | WO-2009/0146209 | 12/2009 |
| WO | 2010001932 A1 | 1/2010 |
| WO | WO 2010/009335 | 1/2010 |
| WO | WO-2010/075590 | 7/2010 |
| WO | 2010086863 A2 | 8/2010 |
| WO | WO-2010/111196 A2 | 9/2010 |
| WO | WO-2010/111232 A2 | 9/2010 |
| WO | WO-2010/111238 A2 | 9/2010 |
| WO | WO-2010/120552 A2 | 10/2010 |
| WO | WO-2010/121187 A2 | 10/2010 |
| WO | 2010135369 A1 | 11/2010 |
| WO | 10136604 A1 | 12/2010 |
| WO | 2010136604 A1 | 12/2010 |
| WO | WO-2010/136604 A1 | 12/2010 |
| WO | WO-2011/097103 | 8/2011 |
| WO | 2011119159 A1 | 9/2011 |
| WO | WO-2011/119762 | 9/2011 |
| WO | WO-2011/130448 | 10/2011 |
| WO | WO-2011/133655 | 10/2011 |
| WO | 2011140519 A2 | 11/2011 |
| WO | 2012009684 A2 | 1/2012 |
| WO | WO-2012/009684 | 1/2012 |
| WO | WO-2012/034079 | 3/2012 |
| WO | 2012078955 A1 | 6/2012 |
| WO | WO-2012/082502 | 6/2012 |
| WO | WO-2012/092504 | 7/2012 |
| WO | WO-2012/142319 | 10/2012 |
| WO | WO-2012/166819 | 12/2012 |
| WO | 2013003644 A1 | 1/2013 |
| WO | WO-2013/012689 | 1/2013 |
| WO | WO-2013/025535 | 2/2013 |
| WO | WO-2013/059509 | 4/2013 |
| WO | WO-2013/173657 | 11/2013 |
| WO | WO-2013/177211 | 11/2013 |
| WO | WO-2014/063111 | 4/2014 |
| WO | WO-2014/165264 | 10/2014 |
| WO | 2014186532 A1 | 11/2014 |

OTHER PUBLICATIONS

PCT/US2011/032371, International Search Report dated Jul. 7, 2011.
Abreu Filho et al., "Influence of metal alloy and the profile of coronary stents in patients with multivessel coronary disease," Clinics 66(6):985-989 (2011).
Akoh et al., "One-Stage Synthesis of Raffinose Fatty Acid Polyesters." Journal Food Science 52:1570 (1987).
Albert et al., "Antibiotics for preventing recurrent urinary tract infection in non-pregnant women," Cochrane Database System Rev. 3, CD001209 (2004).
Au et al., "Methods to improve efficacy of intravesical mitomycin C: Results of a randomized phase III trial," Journal of the National Cancer Institute, 93(8), 597-604 (2001).
AU2006270221 Exam Report dated Apr. 6, 2010.
AU2007243268 Exam Report dated May 15, 2013.
AU2007243268 Exam Report dated Aug. 31, 2011.
AU2009251504 Exam Report dated Dec. 8, 2011.
AU2009270849 Exam Report dated Feb. 14, 2012.
AU2011232760 Exam Report dated Apr. 10, 2013.
AU2011256902 Exam Report dated Jun. 13, 2013.
AU2012203203 Exam Report dated Apr. 12, 2013.
AU2012203577 Exam Report dated Jun. 7, 2013.
AU2011256902 Office Action dated Jun. 10, 2014.
Balss et al., "Quantitative spatial distribution of sirolumus and polymers in drug-eluting stents using confocal Raman microscopy," J. of Biomedical Materials Research Part A, 258-270 (2007).
Belu et al., "Three-Dimensional Compositional Analysis of Drug Eluting Stent Coatings Using Cluster Secondary Ioan Mass Spectroscopy," Anal. Chem. 80:624-632 (2008).
Belu, et al., "Chemical imaging of drug eluting coatings: Combining surface analysis and confocal Rama microscopy" J. Controlled Release 126: 111-121 (2008).
Boneff, "Topical Treatment of Chronic Prostatitis and Premature Ejaculation," International Urology and Nephrology 4(2):183-186 (1971).
Bookbinder et al., "A recombinant human enzyme for enhanced interstitial transport of therapeutics," Journal of Controlled Release 114:230-241 (2006).
Borchert et al., "Prevention and treatement of urinary tract infection with probiotics: Review and research perspective," Indian Journal Urol. 24(2):139-144 (2008).
Brunstein et al., "Histamine, a vasoactive agent with vascular disrupting potential improves tumour response by enhancing local drug delivery," British Journal of Cancer 95:1663-1669 (2006).

(56) References Cited

OTHER PUBLICATIONS

Bugay et al., "Raman Analysis of Pharmaceuticals," in "Applications of Vibrational Spectroscopy in Pharmaceutical Research and Development," Ed. Pivonka, D.E., Chalmers, J.M., Griffiths, P.R. Wiley and Sons, p. 1-24. (2007).
CA 2757276 Office Action dated Feb. 15, 2013.
CA 2757276 Office Action dated Feb. 5, 2014.
CA 2794704 Office Action dated Feb. 7, 2014.
CA 2613280 Office Action dated Oct. 2, 2012.
CA 2615452 Office Action dated Dec. 19, 2012.
CA 2615452 Office action dated Oct. 8, 2013.
CA 2650590 Office action dated Jul. 23, 2013.
CA 2613280 Office action dated Dec. 10, 2013.
CA 2667228 Office action dated Jan. 22, 2014.
CA 2679712 Office action dated Feb. 24, 2014.
CA 2684482 Office action dated Nov. 10, 2011.
CA 2684482 Office action dated Jul. 11, 2012.
CA 2688314 Office action dated Jun. 6, 2012.
CA 2667228 office action dated May 7, 2013.
CA 2730995 Office action dated May 29, 2013.
CA 2730995 Office action dated Sep. 26, 2012.
CA 2730995 Office action dated Feb. 20, 2014.
CA 2756307 Office action dated Feb. 18, 2013.
CA 2756307 Office action dated Mar. 24,2014.
CA 2756386 Office action dated Mar. 15, 2013.
CA 2756388 Office action dated Apr. 11, 2013.
CA 2756388 Office action dated Apr. 14, 2014.
CA 2759015 Office action dated Apr. 8, 2013.
CA 2759015 Office action dated Jul. 21, 2014.
CA 2756386 Office action dated Oct. 24, 2013.
CA 2756386 Office action dated May 16, 2014.
CA 2805631 Office action dated Jan. 17, 2014.
CA 2823355 Office action dated Apr. 14, 2014.
Cadieux et al., "Use of triclosan-eluting ureteral stents in patients with long-term stents," J. Endourol (Epub) (Jun. 19, 2009).
Channon et al., "Nitric Oxide Synthase in Atherosclerosis and Vascular Injury: Insights from Experimental Gene Therapy," Arteriosclerosis, Thrombosis and Vascular Biology, 20(8):1873-1881 (2000).
Chen et al. Immobilization of heparin on a silicone surface through a heterobifunctional PEG spacer. Biomaterials. 26(35):7418-24 (2005).
Chlopek et al. "The influence of carbon fibres on the resorption time and mechanical properties of the lactide-glycolide co-polymer." J. Biomater. Sci. Polymer Edn, vol. 18, No. 11, pp. 1355-1368 (2007).
Clair and Burks, "Thermoplastic/Melt-Processable Polyimides," NASA Conf. Pub. #2334 pp. 337-355 (1984).
CN 2006800258093 Office action dated May 30, 2012.
CN 200780047425.6 Office action dated Aug. 3, 2012.
CN 200780047425.6 Office action dated Feb. 28, 2013.
CN 200880007308.1 Office action dated Jul. 3, 2013.
CN 200880007308.1 Office action dated Nov. 23, 2011.
CN 200880007308.1 Office action dated Oct. 18, 2012.
CN 200880007308.1 Office action dated Jan. 2, 2014.
CN 200880020515 Office action dated Jul. 22, 2013.
CN 200880020515 Office action dated Oct. 9, 2012.
CN 200880020515 Office action dated Apr. 15, 2014.
CN 200880100102.3 Office action dated Apr. 11, 2013.
CN 200880100102.3 Office action dated Jun. 1, 2012.
CN 200880100102.3 Office action dated Dec. 11, 2013.
CN 200880100102.3 Office action dated Aug. 27, 2014.
CN 200980122691 Office action dated Oct. 10, 2012.
CN 200980136432.2 Office action dated Jan. 14, 2013.
CN 200980136432.2 Office action dated Nov. 4, 2013.
CN 200980136432.2 Office action dated Jul. 3, 2014.
CN 201080024973.9 Office action dated Dec. 20, 2013.
CN 201080024973.9 Office action dated Aug. 7, 2014.
CN 201210206265.8 Office action dated Sep. 15, 2014.
Cohen, et al. "Sintering Technique for the Preparation of Polymer Matrices for the Controlled Release of Macromolecules." Journal of Pharamceutical Sciences, vol. 73, No. 8, p. 1034-1037 (1984).
Colombo et al. "Selection of Coronary Stents," Journal of the American College of Cardiology, vol. 40, No. 6, p. 1021-1033. (2002).
CRC Handbook of chemistry and physics. 71st ed. David R. Lide, Editor-in-Chief. Boca Raton, FL, CRC Press; 6-140 (1990).
Cyrus et al., "Intramural delivery of rapamycin with alphavbeta3-targeted paramagnetic nanoparticles inhibits stenosis after balloon injury," Arterioscler Thromb Vasc Biol 28:820-826 (2008).
DERWENT-ACC-No. 2004-108578 Abstracting 2004003077; Jan. 8, 2004; 3 pages.
DiStasi et al., "Percutaneous sequential bacillus Calmette-Guerin and mitomycin C for panurothelial carcinomatosis," Can. J. Urol. 12(6):2895-2898 (2005).
Domb and Langer, "Polyanhydrides. I. Preparation of High Molecular Weight Polyanhydrides." J. Polym Sci. 25:3373-3386 (1987).
Domingo, C. et al., "Precipication of ultrafine organic crystals from the rapid expansion of supercritical solutions over a capillary and a frit nozzle," J. Supercritical Fluids 10:39-55 (1997).
Dzik-Jurasz, "Molecular imaging in vivo: an introduction," The British Journal of Radiology, 76:S98-S109 (2003).
EA 200901254 Office Action dated Jul. 29, 2013.
EA 200901254/28 Office Action dated Jun. 28, 2012.
EA 201001497 Office Action dated Feb. 13, 2013.
EA 201001497 Office Action dated Jul. 29, 2013.
Electrostatic Process, Wiley Encyclopedia of Electrical and Electronics Engineering, John Wiley & Sons, Inc. 1999; 7:15-39.
Eltze et al., "Imidazoquinolinon, imidazopyridine, and isoquinolindione derivatives as novel and potent inhibitors of the poly (ADP-ribose) polymerase (PARP): a comparison with standard PARP inhibitors," Mol. Pharmacol 74(6):1587-1598 (2008).
EP06773731.2 Search Report dated Oct. 2, 2012.
EP06787258.0 Office Action dated Mar. 15, 2013.
EP06787258.0 Search Report dated Feb. 6, 2012.
EP07756094.4 Office Action dated Jan. 21, 2014.
EP07756094.4 Office Action dated May 29, 2013.
EP07756094.4 Search Report dated Aug. 31, 2012.
EP08705772.5 Office Action dated Oct. 30, 2013.
EP08705772.5 Search Report dated Feb. 20, 2013.
EP08733210.2 Office action dated Jul. 16, 2013.
EP08733210.2 Search Report dated Oct. 23, 2012.
EP08756215.3 Search Report dated Oct. 5, 2011.
EP08756215.3 Search Report dated Jan. 28, 2013.
EP09755571.8 Office Action dated Dec. 13, 2013.
EP09755571.8 Search Report dated Apr. 9, 2013.
EP09798764.8 Search Report dated Sep. 30, 2013.
EP09805981.9 Office Action dated Feb. 13, 2013.
EP10756676.2 Search Report dated Jan. 31, 2014.
EP10756696.0 Search Report dated Oct. 10, 2013.
EP10764884.2 Search Report dated Oct. 28, 2013.
EP10765295.0 Search Report dated Oct. 17, 2013.
EP11769546.0 Search Report dated Sep. 19, 2013.
EP10800642.0 Search Report dated Mar. 19, 2014.
EP11772624.0 Search Report dated Jun. 5, 2014.
EP09798764.8 Office Action dated Jun. 30, 2014.
EP11807601.7 Search Report dated Sep. 17, 2014.
EP11852627.6 Search Report dated Sep. 17, 2014.
Ettmayer et al. Lessons learned from marketed and investigational prodrugs. J Med Chem. 47(10):2393-404 (2004).
Fibbi et al., "Chronic inflammation in the pathogenesis of benign prostatic hyperplasia," Int J Androl. 1:33(3):475-88 (2010).
Fleischmann et al., "High Expression of Gastrin-Releasing Peptide Receptors in the Vascular bed of Urinary Tract Cancers: Promising Candidates for Vascular Targeting Applications." Endocr. Relat. Cancer 16(2):623-33 (2009).
Froehlich et al., "Conscious sedation for gastroscopy: patient tolerance and cardiorespiratory parameters," Gastroenterology 108(3):697-704 (1995).
Fujiwara et al., "Insulin-like growth factor 1 treatment via hydrogels rescues cochlear hair cells from ischemic injury," NeuroReport 19(16):1585-1588 (2008).

(56) References Cited

OTHER PUBLICATIONS

Fulton et al. Thin Fluoropolymer films and nanoparticle coatings from the rapid expansion of supercritical carbon dioxide solutions with electrostatic collection, Polymer Communication. p. 2627-3632 (2003).
Green et al., "Simple conjugated polymer nanoparticles as biological labels," Proc Roy Soc A. published online Jun. 24, 2009 doi:10.1098/rspa.2009.0181.
Griebenow et al., "On Protein Denaturation in Aqueous-Organic Mixtures but not in Pure Organic Solvents," J. Am Chem Soc., vol. 118. No. 47, 11695-11700 (1996).
Hamilos et al., "Differential effects of Drug-Eluting Stents on Local Endothelium-Dependent Coronary Vasomotion." JACC vol. 51, No. 22, 2008, Endothelium and DES p. 2123-9 (2008).
Han, et al., "Studies of a Novel Human Thrombomodulin Immobilized Substrate: Surface Characterization and Anticoagulation Activity Evaluation." J. Biomater. Sci. Polymer Edn, 12(10), 1075-1089 (2001).
Hartmann et al., "Tubo-ovarian abscess in virginal adolescents: exposure of the underlying etiology," J. Pediatr Adolesc Gynecol, 22(3):313-16 (2009).
Hasegawa et al., "Nylong 6/Na-montmorillonite nanocomposites prepared by compounding Nylon 6 with Na-montmorillonite slurry," Polymer 44:2933-2937 (2003).
Hinds, WC. Aerosol Technology, Properties, Behavior and Measurement of Airborne Particles, Department of Environmental Health Sciences, Harvard University School of Public Health, Boston, Massachusetts. p. 283-314 (1982).
Hladik et al., "Can a topical microbicide prevent rectal HIV transmission?" PLoS Med. 5(8):e167 (2008).
Iconomidou et al., "Secondary Structure of Chorion Proteins of the Teleosatan Fish Dentex dentex by ATR FR-IR and FT-Raman Spectroscopy," J. of Structural Biology, 132, 112-122 (2000).
ID-W00201003529 Office action dated Apr. 28, 2014.
IL-208648 Official Notification dated Feb. 9, 2012.
IL-201550 Official Notification dated Dec. 8, 2013.
IN-368/DELNP/2008 Exam Report dated Oct. 17, 2011.
IN-6884/DELNP/2009 Office Action dated Oct. 31, 2013.
IN-7740/DELNP/2009 Office Action dated Jul. 29, 2014.
Jackson et al., "Characterization of perivascular poly(lactic-co-glycolic acid) films containing paclitaxel" *Int. J. of Pharmaceutics*, 283:97-109 (2004), incorporated in its entirety herein by reference.
Jensen et al., Neointimal hyperplasia after sirollmus-eluting and paclitaxel-eluting stend implantation in diabetic patients: the randomized diabetes and drug eluting stent (DiabeDES) intravascular ultrasound trial. European heart journal (29), pp. 2733-2741. Oct. 2, 2008. Retrieved from the Internet. Retrieved on [Jul. 17, 2012]. URL:<http://eurheartj.oxfordjournals.org/content/29/22/2733.full.pdf> entire document.
Jewell, et al., "Release of Plasmid DNA from Intravascular Stents Coated with Ultrathin Multilayered Polyelectrolyte Films" *Biomacromolecules*. 7: 2483-2491 (2006).
Johns, H.E, J.R.Cunningham, Thomas, Charles C., Publisher, "The Physics of Radiology," Springfield, IL, pp. 133-143 (1983).
Joner et al. "Site-specific targeting of nanoparticle prednisolone reduces in-stent restenosis in a rabbit model of established atheroma," Arterioscler Thromb Vasc Biol. 28:1960-1966 (2008).
Jovanovic et al. "Stabilization of Proteins in Dry Powder Formulations Using Supercritical Fluid Technology," Pharm. Res. 21(11) (2004).
JP 2008-521633 Office Action dated Oct. 12, 2012.
JP 2008-521633 Office Action dated Dec. 28, 2011.
JP 2008-521633 Office Action dated Oct. 3, 2014.
JP-2009-534823 Office Action dated Apr. 23, 2013.
JP-2009-534823 Office Action dated Feb. 21, 2012.
JP-2009-534823 Office Action dated Sep. 20, 2012.
JP-2009-545647 Office Action dated Jun. 5, 2012.
JP-2009-545647 Office Action dated May 14, 2013.
JP-2009-545647 Office Action dated Apr. 22, 2014.
JP-2010-504253 Office Action dated Dec. 12, 2011.
JP-2010-504253 Office Action dated Dec. 7, 2012.
JP-2010-510441 Office action dated May 7, 2013.
JP-2011-505248 Office action dated Jun. 4, 2013.
JP-2011-518920 Office action dated Dec. 17, 2012.
JP-2011-518920 Office action dated Oct. 23, 2013.
JP-2012-503677 Office action dated Jan. 18, 2013.
JP-2012-503677 Office action dated Nov. 1, 2013.
JP-2012-151964 Office Action dated Dec. 10, 2013.
JP-2013-024508 Office Action dated May 2, 2014.
JP-2013-190903 Office Action dated Sep. 2, 2014.
Kazemi et al., "The effect of betamethasone gel in reducing sore throat, cough, and hoarseness after laryngo-tracheal intubation," Middle East J. Anesthesiol. 19(1):197-204 (2007).
Kehinde et al., "Bacteriology of urinary tract infection associated with indwelling J ureteral stents," J. Endourol. 18(9):891-896 (2004).
Kelly et al., "Double-balloon trapping technique for embolization of a large wide-necked superior cerebellar artery aneurysm: case report," Neurosurgery 63(4 Suppl 2):291-292 (2008).
Khan et al., "Chemistry and the new uses of Sucrose: How Important?" Pur and Appl. Chem 56:833-844 (1984).
Khan et al., "Cyclic Acetals of 4,1',6'-Trichloro-4,1',6',-Trideoxy-Trideoxy-galacto-Sucrose and their Conversion into Methyl Ether Derivatives." Carb. Res. 198:275-283 (1990).
Khan et al., "Enzymic Regioselective Hydrolysis of Peracetylated Reducing Disaccharides, Specifically at the Anomeric Centre: Intermediates for the Synthesis of Oligosaccharides." Tetrahedron Letters 34:7767 (1933).
Khayankarn et al., "Adhesion and Permeability of Polyimide-Clay Nanocomposite Films for Protective Coatings," Journal of Applied Polymer Science, vol. 89, 2875-2881 (2003).
Koh et al., A novel nanostructured poly(lactic-co-glycolic-acid)-multi-walled carbon nanotube composite for blood-contacting applications: Thrombogenicity studies, Acta Biomaterialia 5:3411-3422 (2009).
KR10-2008-7003756 Office Action dated Sep. 23, 2013.
KR10-2008-7003756 Office Action dated Oct. 30, 2012.
KR10-2013-7031237 Office Action dated Mar. 17, 2014.
Kurt et al., "Tandem oral, rectal and nasal administrations of Ankaferd Blood Stopper to control profuse bleeding leading to hemodynamic instability," Am J. Emerg. Med. 27(5):631, e1-2 (2009).
Labhasetwar et al., "Arterial uptake of biodegradable nanoparticles: effect of surface modifications," Journal of Pharmaceutical Sciences, vol. 87, No. 10, Oct. 1998; 1229-1234.
Lamm et al., "Bladder Cancer: Current Optimal Intravesical Treatment: Pharmacologic Treatment," Urologic Nursing 25(5):323-6, 331-2 (Oct. 26, 2005).
Latella et al., "Nanoindentation hardness. Young's modulus, and creep behavior of organic-inorganic silica-based sol-gel thin films on copper," J Mater Res 23(9): 2357-2365 (2008).
Lawrence et al., "Rectal tacrolimus in the treatment of resistant ulcerative proctitis," Aliment. Pharmacol Ther. 28(10):1214-20 (2008).
Lee et al., "Novel therapy for hearing loss: delivery of insulin-like growth factor 1 to the cochlea using gelatin hydrogel," Otol. Neurotol. 28(7):976-81 (2007).
Lehmann et al, "Drug treatment of nonviral sexually transmitted diseases: specific issues in adolescents," Pediatr Drugs 3(7):481-494 (2001).
Mahoney et al., "Three-Dimensional Compositional Analysis of Drug Eluting Stent Coatings Using Cluster Secondary Ion mass Spectrometry," Anal. Chem. , 80, 624-632 (2008).
Mario, C.D. et al., "Drug-Eluting Bioabsorbable Magnesium Stent," J. Interventional Cardiology 16(6):391-395 (2004).
Matsumoto, D, et al. Neointimal Coverage of Sirolimus-Eluting Stents at 6-month Follow-up: Evaluated by Optical Coherence Tomography, European Heart Journal, 28:961-967 (2006).
McAlpine, J.B. et al., "Revised NMR Assignments for Rapamycine," J. Antibiotics 44:688-690 (1991).
Mehik et al., "Alfuzosin treatment for chronic prostatitis/chronic pelvic pain syndrome: a prospecitve, randomized, double-blind, placebo-controlled, pilot study," Urology 62(3):425-429 (2003).

(56) References Cited

OTHER PUBLICATIONS

Mei et al., "Local Delivery of Modified Paclitaxel-Loaded Poly(ε-caprolactone)/Pluronic F68 Nanoparticles for Long-Term Inhibition of Hyperplasia," Journal of Pharmaceutical Sciences, vol. 98, No. 6, Jun. 2009.
Melonakos et al., Treatment of low-grade bulbar transitional cell carcinoma with urethral instillation of mitomycin C, Oct. 28, 2008, Adv. Urol., 173694 Epub.
Merrett et al., "Interaction of corneal cells with transforming growth factor beta2-modified poly dimethyl siloxane surfaces," Journal of Biomedical Materials Research, Part A, vol. 67A, No. 3, pp. 981-993 (2003).
Merriam-Webster Online Dictionary, obtained online at: http://www.merriam-webster.com/dictionary/derivative, downloaded Jan. 23, 2013.
Middleton and Tipton, Synthetic biodegradable polymers as orthopedic devises. Biomaterials 21:2335-46.(2000).
Minchin, "Nanomedicine: sizing up targets with nanoparticles," Nature Nanotechnology, vol. 33:12-13 (2008).
Minoque et al., "Laryngotracheal topicalization with lidocaine before intubation decreases the incidence of coughing on emergence from general anesthesia," Anesth. Analg. 99(4):1253-1257 (2004).
Mishima et al. "Microencapsulation of Proteins by Rapid Expansion of Supercritical Solution with a Nonsolvent," AIChE J. 46(4):857-65 (2000).
Mocco et al., "Pharos neurovascular intracranail stent: Elective use for a symptomatic stenosis refractory to medical therapy," Catheter Cardiovasc. Interv. (epub) (Mar. 2009).
Mollen et al., "Prevalence of tubo-ovarian abcess in adolescents diagnosed with pelvice inflammatory disease in a pediatric emergency department," Pediatr. Emerg. Care, 22(9): 621-625 (2006).
Moroni et al., "Post-ischemic brain damage:targeting PARP-1 within the ischemic neurovaschular units as a realistic avenue to stroke treatment," FEBS J. 276(1):36-45 (2009).
Muhlen et al., "Magnetic Resonance Imaging Contrast Agent Targeted Toward Activated Platelets Allows in Vivo Detection of Thrombosis and Monitoring of Thrombolysis Circulation," 118:258-267 (2008).
Murphy et al., "Chronic prostatitis: management strategies," Drugs 69(1): 71-84 (2009).
MX/a/2010/01148 Office Action dated Feb. 11, 2014.
NZ 588549 Examination Report dated Mar. 28, 2011.
NZ 600814 Examination Report dated Jun. 29, 2012.
O'Neil et al., "Extracellular matrix binding mixed micelles for drug delivery applications," Journal of Controlled Release 137:146-151 (2009).
O'Donnell et al., "Salvage intravesical therapy with interferon-alpha 2b plus low dose bacillus Calmette-Guerin alone previously failed," Journ. Urology, 166(4):1300-1304 (2001).
Olbert et al., "In vitro and in vivo effects of CpG-Oligodeoxynucleotides (CpG-ODN) on murine transitional cell carcinoma and on the native murine urinary bladder wall," Anticancer Res. 29(6):2067-2076 (2009).
Ong and Serruys, "Technology Insight: an overview of research in drug-eluting stents," Nat. Clin. Parct. Cardiovas. Med. 2(12):647-658 (2005).
PCT/US06/24221 International Preliminary Report on Patentability dated Dec. 24, 2007.
PCT/US06/24221 International Search Report dated Jan. 29, 2007.
PCT/US06/27321 International Preliminary Report on Patentability dated Jan. 16, 2008.
PCT/US06/27321 International Search Report dated Oct. 16, 2007.
PCT/US06/27322 International Preliminary Report on Patentability dated Jan. 16, 2008.
PCT/US06/27322 International Search Report dated Apr. 25, 2007.
PCT/US07/10227 International Preliminary Report on Patentability dated Oct. 28, 2008.
PCT/US07/10227 International Search Report dated Aug. 8, 2008.
PCT/US07/80213 International Preliminary Report on Patentability dated Apr. 7, 2009.
PCT/US07/80213 International Search Report dated Apr. 16, 2008.
PCT/US07/82275 International Search Report dated Apr. 18, 2008.
PCT/US07/82775 International Preliminary Report on Patentablity dated Apr. 28, 2009.
PCT/US08/11852 International Preliminary Report on Patentability dated Apr. 20, 2010.
PCT/US08/11852 International Search Report dated Dec. 19, 2008.
PCT/US08/50536 International Preliminary Report on Patentability dated Jul. 14, 2009.
PCT/US08/50536 International Search Report dated Jun. 2, 2008.
PCT/US08/60671 International Preliminary Report on Patentability dated Oct. 20, 2009.
PCT/US08/60671 International Search Report dated Sep. 5, 2008.
PCT/US08/64732 International Preliminary Report on Patentability dated Dec. 1, 2009.
PCT/US08/64732 International Search Report dated Sep. 4, 2008.
PCT/US09/41045 International Preliminary Report on Patentability dated Oct. 19, 2010.
PCT/US09/41045 International Search Report dated Aug. 11, 2009.
PCT/US09/50883 International Preliminary Report on Patentability dated Jan. 18, 2011.
PCT/US09/50883 International Search Report dated Nov. 17, 2009.
PCT/US09/69603 International Preliminary Report on Patentability dated Jun. 29, 2011.
PCT/US09/69603 International Search Report dated Nov. 5, 2010.
PCT/US10/28195 International Preliminary Report on Patentability dated Sep. 27, 2011.
PCT/US10/28195 Search Report and Written Opinion dated Jan. 21, 2011.
PCT/US10/28253 International Preliminary Report on Patentability dated Sep. 27, 2011.
PCT/US10/28253 Search Report and Written Opinion dated Dec. 6, 2010.
PCT/US10/28265 International Report on Patentability dated Sep. 27, 2011.
PCT/US10/28265 Search Report and Written Opinion dated Dec. 3, 2010.
PCT/US10/29494 International Preliminary Report on Patentability dated Oct. 4, 2011.
PCT/US10/29494 Search Report and Written Opinion dated Feb. 7, 2011.
PCT/US10/31470 International Preliminary Report on Patentability dated Oct. 18, 2011.
PCT/US10/31470 Search Report and Written Opinion dated Jan. 28, 2011.
PCT/US10/42355 International Preliminary Report on Patentability dated Jan. 17, 2012.
PCT/US10/42355 Search Report dated Sep. 2, 2010.
PCT/US11/032371 International Report on Patentability dated Oct. 16, 2012.
PCT/US11/032371 International Search Report dated Jul. 7, 2011.
PCT/US11/044263 International Search Report, International Preliminary Report on Patentability and Written Opinion dated Feb. 9, 2012.
PCT/US11/051092 International Preliminary Report on Patentability dated Mar. 21, 2013.
PCT/US11/051092 International Search Report dated Mar. 27, 2012.
PCT/US11/051092 Written Opinion dated Mar. 27, 2012.
PCT/US11/22623 International Preliminary Report on Patentability dated Aug. 7, 2012.
PCT/US11/22623 Search Report and Written Opinion dated Mar. 28, 2011.
PCT/US11/29667 International Search Report and Written Opinion dated Jun. 1, 2011.
PCT/US11/67921 International Preliminary Report on Patentability dated Jul. 11, 2013.
PCT/US11/67921 Search Report and Written Opinion dated Jun. 22, 2012.
PCT/US12/040040 International Search Report dated Sep. 7, 2012.
PCT/US12/33367 International Preliminary Report on Patentability dated Oct. 15, 2013.
PCT/US12/33367 International Search Report dated Aug. 1, 2012.

(56) References Cited

OTHER PUBLICATIONS

PCT/US12/46545 International Search Report dated Nov. 20, 2012.
PCT/US13/41466 International Search Report and Written Opinion dated Oct. 17, 2013.
PCT/US13/42093 International Search Report and Written Opinion dated Oct. 24, 2013.
PCT/US2011/033225 International Search Report and Written Opinion dated Jul. 7, 2011.
PCT/US2012/60896 International Search Report and Written Opinion dated Dec. 28, 2012.
PCT/US2013/065777 International Search Report and Written Opinion dated Jan. 29, 2014.
PCT/US2014/025017 International Search Report and Written Opinion dated Jul. 7, 2014.
PCT/US2014/038117 International Search Report and Written Opinion dated Oct. 7, 2014.
Perry et al., Chemical Engineer's Handbook, 5th Edition, McGraw-Hill, New York, 1973; 20-106.
Plas et al., "Tubers and tumors: rapamycin therapy for benign and malignant tumors", Curr Opin Cell Bio 21: 230-236, (2009).
Poling et al., The Properties of Gases and Liquids. McGraw-Hill. 9:1-9.97 (2001).
Pontari, "Chronic prostatitis/chronic pelvic pain syndrome in elderly men: toward better understanding and treatment," Drugs Aging 20(15):1111-1115 (2003).
Pontari, "Inflammation and anti-inflammatory therapy in chronic prostatits," Urology 60(6Suppl):29-33 (2002).
Putkisto, K. et al. "Polymer Coating of Paper Using Dry Surface Treatment—Coating Structure and Performance", ePlace newsletter, Apr. 12, 2004, vol. 1, No. 8, pp. 1-20.
Raganath et al., "Hydrogel matrix entrapping PLGA-paclitaxel microspheres: drug delivery with near zero-order release and implantability advantages for malignant brain tumour," Pharm Res (Epub) Jun. 20, 2009.
Ranade et al., "Physical characterization of controlled release of paclitaxel from the TAXUS Express2 drug-eluting stent," J. Biomed Mater. Res. 71(4):625-634 (2004).
Reddy et al., "Inhibition of apoptosis through localized delivery of rapamycin-loaded nanoparticles prevented neointimal hyperplasia and reendothelialized injured artery," Circ Cardiovasc Interv 1:209-216 (2008).
Ristikankare et al., "Sedation, topical pharnygeal anesthesia and cardiorespiratory safety during gastroscopy," J. Clin Gastorenterol. 40(1):899-905 (2006).
Sahajanand Medical Technologies (Supralimus Core; Jul. 6, 2008).
Salo et al., "Biofilm formation by *Escherichia coli* isolated from patients with urinary tract infections," Clin Nephrol. 71(5):501-507 (2009).
Saxena et al., "Haemodialysis catheter-related bloodstream infections: current treatment options and strategies for prevention," Swiss Med Wkly 135:127-138 (2005).
Schetsky, L. McDonald, "Shape Memory Alloys", Encyclopedia of Chemical Technology (3d Ed), John Wiley & Sons 1982, vol. 20 pp. 726-736.
Scheuffler et al., "Crystal Structure of Human Bone Morphogenetic Protein-2 at 2.7 Angstrom resolution," Journal of Molecular Biology, vol. 287, Issue 1, Mar. 1999, retrieved online at http://www.sciencedirect.com/science/article/pii/S002283699925901.
Schmidt et al., "A Comparison of the Mechanical Performance Characteristics of Seven Drug-Eluting Stent Systems," Catheterization and Cardiovascular Interventions 73:350-360 (2009).
Schmidt et al., "In vitro measurement of quality parameters of stent-catheter systems," Biomed Techn 50(S1):1505-1506 (2005).
Schmidt et al., "New aspects of in vitro testing of arterial stents based on the new European standard," EN 14299, [online] (2009), [retrieved on Mar. 10, 2001] http://www.lib0ev.de/pl/pdf/EN14299.pdf (2009).
Schmidt et al., "Trackability, Crossability, and Pushability of Coronary Stent Systems—An Experimental Approach," Biomed Techn 47:1, S. 124-126 (2002).

Schreiber, S.L. et al., "Atomic Structure of the Rapamycin Human Immunophilin FKBP-12 Complex," J. Am. Chem. Soc. 113:7433-7435 (1991).
Sen et al., "Topical heparin: A promising agent for the prevention of tracheal stenosis in airway surgery," J. Surg. Res (Epub ahead of print) Feb. 21, 2009.
SG201007602-4 Examination Report dated Feb. 13, 2013.
SG201007602-4 Written Opinion dated May 25, 2012.
Shekunov et al. "Crystallization Processes in Pharmaceutical Technology and Drug Delivery Design." Journal of Crystal Growth 211, pp. 122-136 (2000).
Simpson et al., "Hyaluronan and hyaluronidase in genitourinary tumors." Front Biosci. 13:5664-5680 (2009).
Smith et al., "Mitomycin C and the endoscopic treatment of laryngotracheal stenosis: are two applications better than one?" Laryngoscope 119(2):272-283 (2009).
Sumathi et al., "Controlled comparison between betamethasone gel and lidocaine jelly applied over tracheal tube to reduce postoperative sore throat, cough, and hoarseness of voice," Br. J. Anaesth. 100(2):215-218 (2008).
Szabadits et al., "Flexibility and trackability of laser cut coronary stent systems," Acta of Bioengineering and Biomechanics 11(3):11-18 (2009).
Testa, B. Prodrug research: futile or fertile? Biochem Pharmacol. Dec. 1, 2004;68(11):2097-106.
Thalmann et al., "Long-term experience with bacillus Calmette-Guerin therapy of upper urinary tract transitional cell carcinoma in patients not eligible for surgery," J Urol. 168(4 Pt 1):1381-1385 (2002).
Torchlin, "Micellar Nanocarriers: Pharmaecutial Perspectives," Pharmaceutical Research, vol. 24, No. 1, Jan. 2007.
U.S. Appl. No. 11/158,724 Office action dated Dec. 31, 2013.
U.S. Appl. No. 11/158,724 Office action dated May 23, 2013.
U.S. Appl. No. 11/158,724 Office action dated Sep. 17, 2009.
U.S. Appl. No. 11/158,724 Office action dated Sep. 26, 2012.
U.S. Appl. No. 11/158,724 Office action dated Sep. 8, 2008.
U.S. Appl. No. 11/158,724 Office action dated Jun. 25, 2014.
U.S. Appl. No. 11/877,591 Final office action dated Nov. 4, 2013.
U.S. Appl. No. 11/877,591 Office action dated Feb. 29, 2012.
U.S. Appl. No. 11/877,591 Office action dated Jul. 1, 2013.
U.S. Appl. No. 11/877,591 Office action dated Sep. 21, 2012.
U.S. Appl. No. 11/877,591 Office action dated May 7, 2014.
U.S. Appl. No. 11/877,591 Final Office Action dated Sep. 29, 2014.
U.S. Appl. No. 11/995,685 Office action dated Aug. 20, 2010.
U.S. Appl. No. 11/995,685 Office Action dated Nov. 24, 2009.
U.S. Appl. No. 11/995,685 Advisory Action dated Oct. 9, 2014.
U.S. Appl. No. 11/995,687 Office Action dated Apr. 6, 2012.
U.S. Appl. No. 11/995,687 Office Action dated Sep. 28, 2011.
U.S. Appl. No. 12/298,459 Office Action dated Apr. 6, 2012.
U.S. Appl. No. 12/298,459 Office Action dated Aug. 10, 2011.
U.S. Appl. No. 12/298,459 Office Action dated May 31, 2013.
U.S. Appl. No. 12/426,198 Office Action dated Feb. 6, 2012.
U.S. Appl. No. 12/426,198 Office Action dated Feb. 7, 2014.
U.S. Appl. No. 12/426,198 Office Action dated Mar. 23, 2011.
U.S. Appl. No. 12/443,959 Office Action dated Dec. 13, 2012.
U.S. Appl. No. 12/443,959 Office Action dated Feb. 15, 2012.
U.S. Appl. No. 12/504,597 Final Office Action dated Oct. 3, 2012.
U.S. Appl. No. 12/504,597 Office Action dated Apr. 1, 2014.
U.S. Appl. No. 12/504,597 Office Action dated Dec. 5, 2011.
U.S. Appl. No. 12/522,379 Office Action dated Apr. 8, 2014.
U.S. Appl. No. 12/522,379 Final Office Action dated Aug. 28, 2013.
U.S. Appl. No. 12/522,379 Office Action dated Dec. 26, 2012.
U.S. Appl. No. 12/595,848 Office Action dated Jan. 13, 2012.
U.S. Appl. No. 12/595,848 Office Action dated Mar. 15, 2013.
U.S. Appl. No. 12/595,848 Office Action dated Oct. 22, 2013.
U.S. Appl. No. 12/595,848 Office Action dated Jun. 3, 2014.
U.S. Appl. No. 12/601,101 Office Action dated Dec. 27, 2012.
U.S. Appl. No. 12/601,101 Office Action dated Feb. 13, 2014.
U.S. Appl. No. 12/601,101 Office Action dated Mar. 27, 2012.
U.S. Appl. No. 12/601,101 Office action dated May 22, 2013.
U.S. Appl. No. 12/648,106 Final Office Action dated Sep. 25, 2012.
U.S. Appl. No. 12/648,106 Office Action dated Jan. 30, 2012.
U.S. Appl. No. 12/648,106 Office Action dated Sep. 18, 2013.

(56) References Cited

OTHER PUBLICATIONS

U.S. Appl. No. 12/729,156 Final Office Action dated Oct. 16, 2012.
U.S. Appl. No. 12/729,156 Office Action dated Feb. 1, 2012.
U.S. Appl. No. 12/729,156 Office Action dated Feb. 13, 2014.
U.S. Appl. No. 12/729,156 Office action dated May 8, 2013.
U.S. Appl. No. 12/729,580 Final Action dated Nov. 14, 2013.
U.S. Appl. No. 12/729,580 Office Action dated Apr. 10, 2012.
U.S. Appl. No. 12/729,580 Office Action dated Jan. 22, 2013.
U.S. Appl. No. 12/729,580 Office Action dated Sep. 10, 2014.
U.S. Appl. No. 12/729,603 Final Office Action dated Oct. 10, 2012.
U.S. Appl. No. 12/729,603 Office Action dated Mar. 27, 2012.
U.S. Appl. No. 12/729,603 Office Action dated Jun. 25, 2014.
U.S. Appl. No. 12/738,411 Final Office action dated Apr. 11, 2013.
U.S. Appl. No. 12/738,411 Office action dated Aug. 21, 2013.
U.S. Appl. No. 12/738,411 Office action dated Feb. 6, 2014.
U.S. Appl. No. 12/738,411 Office action dated May 30, 2014.
U.S. Appl. No. 12/748,134 Office action dated Jul. 18, 2013.
U.S. Appl. No. 12/751,902 Office action dated Dec. 19, 2013.
U.S. Appl. No. 12/751,902 Office action dated Jul. 13, 2012.
U.S. Appl. No. 12/762,007 Final Office action dated Oct. 22, 2013.
U.S. Appl. No. 12/762,007 Final Office action dated Apr. 30, 2014.
U.S. Appl. No. 12/762,007 Office action dated Feb. 11, 2013.
U.S. Appl. No. 13/014,632 Office action dated Jan. 10, 2014.
U.S. Appl. No. 13/014,632 Office action dated May 8, 2013.
U.S. Appl. No. 13/086,335 Office action dated May 22, 2013.
U.S. Appl. No. 13/086,335 Office action dated Apr. 4, 2014.
U.S. Appl. No. 13/229,473 Office action dated Jun. 17, 2013.
U.S. Appl. No. 13/340,472 Office action dated Apr. 26, 2013.
U.S. Appl. No. 13/340,472 Office action dated Jan. 15, 2014.
U.S. Appl. No. 13/340,472 Office action dated Aug. 29, 2014.
U.S. Appl. No. 13/384,216 Final action dated Nov. 6, 2013.
U.S. Appl. No. 13/384,216 Office action dated Apr. 24, 2013.
U.S. Appl. No. 13/605,904 Office action dated Jun. 28, 2013.
U.S. Appl. No. 13/605,904 Office action dated Nov. 27, 2012.
U.S. Appl. No. 13/445,723 Office action dated Mar. 14, 2014.
U.S. Appl. No. 11/995,685 Office action dated Jun. 18, 2014.
Unger et al., "Poly(ethylene carbonate): A thermoelastic and biodegradable biomaterial for drug eluting stent coatings?" Journal of Controlled Release, vol. 117, Issue 3, 312-321 (2007).
Verma et al., "Effect of surface properties on nanoparticle-cell interactions," Small 6(1):12-21 (2010).
Wagenlehner et al., "A pollen extract (Cernilton) in patients with inflammatory chronic prostatitis/chronic pelvic pain syndrome: a multicentre, randomized, prospective, double-blind, placebo-controlled phase 3 study," Eur Urol 9 (Epub) (Jun. 3, 2009).
Wang et al. "Synthesis, characterization, biodegradation, and drug delivery application of biodegradable lactic/glycolic acid polymers: I. Synthesis and characterization" J. Biomater. Sci. Polymer Edn. 11(3):301-318 (2000).
Wang et al. Controlled release of sirolimus from a multilayered PLGA stent matrix. Biomaterials 27:5588-95 (2000).
Wang et al., "Treatment with melagatran alone or in combination with thrombolytic therapy reduced ischemic brain injury," Exp. Neurol 213(1):171-175 (2008).
Warner et al., "Mitomycin C and airway surgery: how well does it work?" Ontolaryngol Head Neck Surg. 138(6):700-709 (2008).
Wermuth, CG Similarity in drugs: reflections on analogue design. Drug Discov Today. 11(7-8):348-54(2006).
Witjes et al., "Intravesical pharmacotherapy for non-muscle-invasive bladder cancer: a critical analysis of currently available drugs, treatment schedules, and long-term results," Eur. Urol. 53(1):45-52 (2008).
Wu et al., "Study on the preparation and characterization of biodegradable polylactide/multi-walled carbon nanotubes nanocomposites." Polymer 48 (2007) 4449-4458.

Xu et al., "Biodegradation of poly(l-lactide-co-glycolide tube stents in bile" Polymer Degradation and Stability. 93:811-817 (2008).
Xue et al., "Spray-as-you-go airway topical anesthesia in patients with a difficult airway: a randomized, double-blind comparison of 2% and 4% lidocaine," Anesth. Analg. 108(2): 536-543 (2009).
Yepes et al., "Tissue-type plasminogen activator in the ischemic brain: more than a thrombolytic," Trends Neurosci. 32(1):48-55 (2009).
Yousof et al., "Reveratrol exerts its neuroprotective effect by modulating mitochondrial dysfunction and associated cell death during cerebral ischemia," Brain Res. 1250:242-253 (2009).
Zhou et al. Synthesis and Characterization of Biodegradable Low Molecular Weight Aliphatic Polyesters and Their Use in Protein-Delivery Systems. J Appl Polym Sci 91:1848-56 (2004).
Zilberman et al., Drug-Eluting bioresorbable stents for various applications, Annu Rev Biomed Eng., 8:158-180 (2006).
Analytical Ultracentrifugation of Polymers and Nanoparticles, W. Machtle and L. Borger, (Springer) 2006, p. 41.
Chalmers, et al. (2007) Wiley and Sons.
European International Search Report of PCT/EP01/05736 dated Oct. 24, 2001.
Finn et al. Differential Response of Delayed Healing . . . Circulation vol. 112 (2005) 270-8.
Greco et al. (Journal of Thermal Analysis and Calorimetry, vol. 72 (2003) 1167-1174.).
Handschumacher, R.E. et al., Purine and Pyrimidine Antimetabolites, Chemotherapeutic Agents, pp. 712-732, Ch. XV1-2, 3rd Edition, Edited by J. Holland, et al., Lea and Febigol, publishers.
Higuchi, Rate of Release of Medicaments from Ointment Bases Containing Drugs in Suspension, Journal of Pharmaceutical Sciences, vol. 50, No. 10, p. 874, Oct. 1961.
Ji, et al., "96-Wellliquid-liquid extraction liquid chromatographytandem mass spectrometry method for the quantitative determination of ABT-578 in human blood samples" Journal of Chromatography B. 805:67-75 (2004).
Ju et al., J. Pharm. Sci. vol. 84, No. 12, 1455-1463.
Levit, et al., "Supercritical C02 Assisted Electrospinning" J. of Supercritical Fluids, 329-333, vol. 31, Issue 3, (Nov. 2004).
Lewis, D. H., "Controlled Release of Bioactive Agents from Lactides/Glycolide Polymers" in Biodegradable Polymers as Drug Delivery Systems, Chasin, M. and Langer, R., eds., Marcel Decker (1990).
Luzzi, L.A., J. Phann. Psy. 59:1367 (1970).
Park et al., Pharm. Res. (1987) 4(6):457-464.
PCT/EP01/05736 International Preliminary Examination Report dated Jan. 14, 2002.
PCT/EP2000/004658 International Search Report from dated Sep. 15, 2000.
PCT/US06/27321 Written Opinion dated Oct. 16, 2007.
PCT/US11/33225 International Search Report and Written Opinion dated Jul. 7, 2011.
PCT/US11/44263 International Search Report and Written Opinion dated Feb. 9, 2012.
PCT/US12/50408 International Search Report dated Oct. 16, 2012.
PCT/US13/41466 International Preliminary Report on Patentability dated Nov. 18, 2014.
PCT/US13/42093 International Preliminary Report on Patentability dated Nov. 25, 2014.
Extended European Search Report for Application No. 14797966.0 dated Dec. 19, 2016.
David Grant, Crystallization Impact on the Nature and Properties of the Crystalline Product, 2003, SSCI, http://www.ssci-inc.com/Information/RecentPublications/ApplicationNotes/CrystallizationImpact/tabid/138/Default.aspx.
Search Report from Singapore Application No. 2013054127 dated Jul. 26, 2017, 5 pages.
Third Party Submission for Application No. JP2015-538086 dated Jun. 4, 2018.

* cited by examiner

STENTS AND OTHER DEVICES HAVING EXTRACELLULAR MATRIX COATING

CROSS REFERENCE

This application claims the benefit of U.S. Provisional Application No. 61/326,956, filed Apr. 22, 2010, the entire content of which is incorporated herein by reference in its entirety.

This application relates to U.S. Provisional Application No. 61/243,955, filed Sep. 18, 2009, PCT US09/41045 filed Apr. 17, 2009; PCT/US2010/28253, filed Mar. 23, 2009, and PCT US2008/60671 filed Apr. 17, 2008. The contents of these applications are incorporated herein by reference in their entirety.

BACKGROUND OF THE INVENTION

Coated stents are used to address the drawbacks of bare stents, namely to treat restenosis and to promote healing of the vessel after opening the blockage by PCI/stenting. Some current drug eluting stents can have physical, chemical and therapeutic legacy in the vessel over time. Others may have less legacy, bur are not optimized for thickness, deployment flexibility, access to difficult lesions, and minimization of vessel wall intrusion.

SUMMARY OF THE INVENTION

Provided herein is a device comprising a stent; and a coating on said stent comprising a polymer and an active agent, wherein the active agent comprises at least one of: extracellular matrix and an extracellular matrix component.

Provided herein is a device comprising a substrate; and a coating on said substrate comprising a polymer and an active agent, wherein the active agent comprises at least one of: extracellular matrix and an extracellular matrix component.

In some embodiments, the coating comprises a plurality of layers. In some embodiments at least one of said layers comprises the polymer. In some embodiments, at least one of said layers comprises the active agent. In some embodiments, the polymer and the active agent are in different layers. In some embodiments, the coating is a laminate coating.

In some embodiments, the extracellular matrix component comprises at least one of: heparin sulfate, chondroitin sulfate, keratan sulfate, hyaluronic acid, collagen, elastin, fibronectin, laminin, merosin, tenascin, vitronectin, and fibrillin.

In some embodiments, the polymer is at least one of: a bioabsorbable polymer and a durable polymer. In some embodiments, bioabsorbable polymer comprises a PLGA copolymer. In some embodiments, bioabsorbable polymer is selected from the group PLGA, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid). In some embodiments, the durable polymer comprises at least one of a polyester, aliphatic polyester, polyanhydride, polyethylene, polyorthoester, polyphosphazene, polyurethane, polycarbonate urethane, aliphatic polycarbonate, silicone, a silicone containing polymer, polyolefin, polyamide, polycaprolactam, polyamide, polyvinyl alcohol, acrylic polymer, acrylate, polystyrene, epoxy, polyethers, celluiosics, expanded polytetrafluoroethylene, phosphorylcholine, polyethyleneyerphthalate, polymethylmethavrylate, poly(ethylmethacrylate/n-butylmethacrylate), parylene C, polyethylene-co-vinyl acetate, polyalkyl methacrylates, polyalkylene-co-vinyl acetate, polyalkylene, polyalkyl siloxanes, polyhydroxyalkanoate, polyfluoroalkoxyphasphazine, poly(styrene-b-isobutylene-b-styrene), poly-butyl methacrylate, poly-byta-diene, and blends, combinations, homopolymers, condensation polymers, alternating, block, dendritic, crosslinked, and copolymers thereof.

In some embodiments, the device has at least one active agent layer defined by a three-dimensional physical space occupied by the active agent and said three dimensional physical space is free of polymer. In some embodiments, at least some of the active agent in said three dimensional physical space defining said at least one active agent layer is in contact with polymer particles present in a polymer layer adjacent to said at least one active agent layer defined by said three-dimensional space free of polymer. In some embodiments, the stent has a stent longitudinal length and the coating has a coating outer surface along said stent longitudinal length, wherein said coating comprises active agent present in the coating below said coating outer surface. In some embodiments, the stent has a stent longitudinal length and the coating has a coating outer surface along said stent longitudinal length, wherein said coating comprises active agent present in the coating up to at least 1 μm below said coating outer surface. In some embodiments, the stent has a stent longitudinal length and the coating has a coating outer surface along said stent longitudinal length, wherein said coating comprises active agent present in the coating up to at least 5 μm below said coating outer surface. In some embodiments, said stent has a stent longitudinal axis and a stent length along said stent longitudinal axis, wherein said coating is conformal to the stent along substantially said stent length. In some embodiments, said stent has a stent longitudinal axis and a stent length along said stent longitudinal axis, wherein said coating is conformal to the stent along at least one of: at least 75% of said stent length, at least 85% of said stent length, at least 90% of said stent length, at least 95% of said stent length, and at least 99% of said stent length. In some embodiments, said stent has a stent longitudinal axis and a plurality of struts along said stent longitudinal axis, wherein said coating is conformal to at least one of: at least 50% of said struts, at least 75% of said struts, at least 90% of said struts, and at least 99% of said struts. In some embodiments, coating conformality is shown by an electron microscopy examination of the device.

In some embodiments, said stent has a stent longitudinal axis and a stent length along said stent longitudinal axis, wherein said coating has a substantially uniform thickness along substantially said stent length. In some embodiments, said stent has a stent longitudinal axis and a stent length along said stent longitudinal axis, wherein said coating has a substantially uniform thickness along at least one of: at least 75% of said stent length, and at least 95% of said stent length. In some embodiments, said stent has a stent longitudinal axis and a stent length along said stent longitudinal axis, wherein said coating has an average thickness determined by an average calculated from coating thickness values measured at a plurality of points along said stent longitudinal axis; wherein a thickness of the coating measured at any point along stent longitudinal axis is at least one of: from about 75% to about 125% of said average thickness, and from about 95% to about 105% of said average thickness.

In some embodiments, the polymer comprises an intimate mixture of two or more polymers.

In some embodiments, said coating has a thickness of at least one of: from about 5 µm to about 50 µm, from about 10 µm to about 20 µm, and from about 50 µm to about 80 µm.

In some embodiments, the device has at least one active agent layer defined by a three-dimensional physical space occupied by the active agent and said three dimensional physical space is free of polymer. In some embodiments, at least some of the active agent in said three dimensional physical space defining said at least one active agent layer is in contact with polymer particles present in a polymer layer adjacent to said at least one active agent layer defined by said three-dimensional space free of polymer. In some embodiments, the substrate has a substrate longitudinal length and the coating has a coating outer surface along said stent longitudinal length, wherein said coating comprises active agent present in the coating below said coating outer surface. In some embodiments, the substrate has a substrate longitudinal length and the coating has a coating outer surface along said stent longitudinal length, wherein said coating comprises active agent present in the coating up to at least 1 µm below said coating outer surface. In some embodiments, the substrate has a substrate longitudinal length and the coating has a coating outer surface along said stent longitudinal length, wherein said coating comprises active agent present in the coating up to at least 5 µm below said coating outer surface. In some embodiments, the substrate has a substrate longitudinal axis and a substrate length along said substrate longitudinal axis, wherein said coating is conformal to the substrate along substantially said substrate length. In some embodiments, the substrate has a substrate longitudinal axis and a substrate length along said substrate longitudinal axis, wherein said coating is conformal to the substrate along at least one of: at least 75% of said substrate length, at least 85% of said substrate length, at least 90% of said substrate length, at least 95% of said substrate length, and at least 99% of said substrate length. In some embodiments, the coating conformality is shown by an electron microscopy examination of the device. In some embodiments, the substrate has a substrate longitudinal axis and a substrate length along said substrate longitudinal axis, wherein said coating has a substantially uniform thickness along substantially said substrate length. In some embodiments, the substrate has a substrate longitudinal axis and a substrate length along said substrate longitudinal axis, wherein said coating has a substantially uniform thickness along at least one of: at least 75% of said substrate length, and at least 95% of said substrate length. In some embodiments, the substrate has a substrate longitudinal axis and a substrate length along said stent longitudinal axis, wherein said coating has an average thickness determined by an average calculated from coating thickness values measured at a plurality of points along said substrate longitudinal axis; wherein a thickness of the coating measured at any point along stent longitudinal axis is at least one of: from about 75% to about 125% of said average thickness, and from about 95% to about 105% of said average thickness. In some embodiments, the polymer comprises an intimate mixture of two or more polymers. In some embodiments, the coating has a thickness of at least one of: from about 5 µm to about 50 µm, from about 10 µm to about 20 µm, and from about 50 µm to about 80 µm.

Provided herein is a device comprising: a stent; a plurality of layers that form a laminate coating on said stent, wherein a first layer comprises a first polymer, a second layer comprises an active agent, a third layer comprises a second polymer, a fourth layer comprises the active agent, and a fifth layer comprises a third polymer, wherein the active agent comprises at least one of: extracellular matrix and an extracellular matrix component.

Provided herein is a device comprising: a substrate; a plurality of layers that form a laminate coating on said stent, wherein a first layer comprises a first polymer, a second layer comprises an active agent, a third layer comprises a second polymer, a fourth layer comprises the active agent, and a fifth layer comprises a third polymer, wherein the active agent comprises at least one of: extracellular matrix and an extracellular matrix component.

In some embodiments, the extracellular matrix component comprises at least one of: heparin sulfate, chondroitin sulfate, keratan sulfate, hyaluronic acid, collagen, elastin, fibronectin, laminin, merosin, tenascin, vitronectin, and fibrillin.

In some embodiments, at least two of said first polymer, said second polymer and said third polymer are the same polymer. In some embodiments, said first polymer, said second polymer and said third polymer are the same polymer.

In some embodiments, at least one of said first polymer, said second polymer and said third polymer is a bioabsorbable polymer. In some embodiments, the bioabsorbable polymer comprises a PLGA copolymer. In some embodiments, the bioabsorbable polymer is selected from the group PLGA, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid).

In some embodiments, at least one of said first polymer, said second polymer and said third polymer is a durable polymer. In some embodiments, the durable polymer comprises at least one of a polyester, aliphatic polyester, polyanhydride, polyethylene, polyorthoester, polyphosphazene, polyurethane, polycarbonate urethane, aliphatic polycarbonate, silicone, a silicone containing polymer, polyolefin, polyamide, polycaprolactam, polyamide, polyvinyl alcohol, acrylic polymer, acrylate, polystyrene, epoxy, polyethers, celluiosics, expanded polytetrafluoroethylene, phosphorylcholine, polyethyleneyerphthalate, polymethylmethavrylate, poly(ethylmethacrylate/n-butylmethacrylate), parylene C, polyethylene-co-vinyl acetate, polyalkyl methacrylates, polyalkylene-co-vinyl acetate, polyalkylene, polyalkyl siloxanes, polyhydroxyalkanoate, polyfluoroalkoxyphasphazine, poly(styrene-b-isobutylene-b-styrene), poly-butyl methacrylate, poly-byta-diene, and blends, combinations, homopolymers, condensation polymers, alternating, block, dendritic, crosslinked, and copolymers thereof.

In some embodiments, at least two of said first polymer, said second polymer and said third polymer are different polymers.

Provided herein is a method of preparing a device comprising a stent and a plurality of layers that form a laminate coating on said stent; said method comprising: providing a stent; and forming a plurality of layers on said stent; wherein at least one of said layers comprises a polymer and at least one of said layers comprises one or more active agents; wherein at least a portion of the active agent comprises at least one of extracellular matrix and an extracellular matrix component.

Provided herein is a method of preparing a device comprising a substrate and a plurality of layers that form a laminate coating on said substrate; said method comprising: providing a substrate; and forming a plurality of layers on said substrate to form said laminate coating on said substrate; wherein at least one of said layers comprises a polymer and at least one of said layers comprises one or more active agents; wherein at least a portion of the active agent comprises at least one of extracellular matrix and an extracellular matrix component.

In some embodiments, the extracellular matrix component comprises at least one of: heparin sulfate, chondroitin sulfate, keratan sulfate, hyaluronic acid, collagen, elastin, fibronectin, laminin, merosin, tenascin, vitronectin, and fibrillin.

Provided herein is a method of preparing a device comprising a stent and a plurality of layers that form a laminate coating on said stent; said method comprising: providing a stent; and forming a plurality of layers to form said laminate coating on said stent; wherein at least one of said layers comprises a polymer and at least one of said layers comprises an active agent comprising at least one of extracellular matrix and an extracellular matrix component, wherein said method creates at least one active agent layer defined by a three-dimensional physical space occupied by the active agent and said three dimensional physical space is free of polymer.

Provided herein is a method of preparing a device comprising a substrate and a plurality of layers that form a laminate coating on said substrate; said method comprising: providing a substrate; and forming a plurality of layers to form said laminate coating on said substrate; wherein at least one of said layers comprises a polymer and at least one of said layers comprises an active agent comprising at least one of extracellular matrix and an extracellular matrix component, wherein said method creates at least one active agent layer defined by a three-dimensional physical space occupied by the active agent and said three dimensional physical space is free of polymer.

Provided herein is a method of preparing a device comprising a stent and a plurality of layers that form a laminate coating on said stent; said method comprising: (a) providing a stent; (b) discharging at least one active agent in dry powder form through a first orifice; (c) forming a supercritical or near supercritical fluid solution comprising at least one supercritical fluid solvent and at least one polymer and discharging said supercritical or near supercritical fluid solution through a second orifice under conditions sufficient to form solid particles of the polymer; (d) depositing the polymer and particles of the active agent onto said stent, wherein an electrical potential is maintained between the substrate and the polymer and active agent particles, thereby forming said coating; and (e) sintering said polymer under conditions that do not substantially modify activity of said active agent, wherein said active agent comprises at least one of extracellular matrix and an extracellular matrix component.

Provided herein is a method of preparing a device comprising a stent and a plurality of layers that form a laminate coating on said substrate; said method comprising: (a) providing a substrate; (b) discharging at least one active agent in dry powder form through a first orifice; (c) forming a supercritical or near supercritical fluid solution comprising at least one supercritical fluid solvent and at least one polymer and discharging said supercritical or near supercritical fluid solution through a second orifice under conditions sufficient to form solid particles of the polymer; (d) depositing the polymer and particles of the active agent onto said substrate, wherein an electrical potential is maintained between the substrate and the polymer and active agent particles, thereby forming said coating; and (e) sintering said polymer under conditions that do not substantially modify activity of said active agent, wherein said active agent comprises at least one of extracellular matrix and an extracellular matrix component.

In some embodiments, step (b) comprises discharging the active agent wherein at least a portion of the active agent is in active form before the method begins, during the method steps, and when the method steps are complete. In some embodiments, step (c) comprises forming solid particles of a bioabsorbable polymer. In some embodiments, step (c) comprises forming solid particles of a durable polymer.

In some embodiments, step (e) comprises forming a polymer layer having a length along a horizontal axis of said device wherein said polymer layer has a layer portion along said length, wherein said layer portion is free of active agent. In some embodiments, step (e) comprises contacting said polymer with a densified fluid. In some embodiments, step (e) comprises contacting said polymer with a densified fluid for a period of time at a temperature of from about 5° C. and 150° C. and a pressure of from about 10 psi to about 500 psi. In some embodiments, step (e) comprises contacting said polymer with a densified fluid for a period of time at a temperature of from about 25° C. and 95° C. and a pressure of from about 25 psi to about 100 psi. In some embodiments, step (e) comprises contacting said polymer with a densified fluid for a period of time at a temperature of from about 50° C. and 85° C. and a pressure of from about 35 psi to about 65 psi.

Provided herein is a method of preparing a device comprising a stent and a plurality of layers that form a laminate coating on said stent; said method comprising: (a) providing a stent; (b) forming a supercritical or near supercritical fluid solution comprising at least one supercritical fluid solvent and a first polymer, discharging said supercritical or near supercritical fluid solution under conditions sufficient to form solid particles of said first polymer, depositing said first polymer particles onto said stent, wherein an electrical potential is maintained between the stent and the first polymer, and sintering said first polymer; (c) depositing active agent particles in dry powder form onto said stent, wherein an electrical potential is maintained between the stent and said active agent particles, and wherein said active agent comprises at least one of extracellular matrix and an extracellular matrix component; and (d) forming a supercritical or near supercritical fluid solution comprising at least one supercritical fluid solvent and a second polymer and discharging said supercritical or near supercritical fluid solution under conditions sufficient to form solid particles of said second polymer, wherein an electrical potential is maintained between the stent and the second polymer, and sintering said second polymer.

Provided herein is a method of preparing a device comprising a substrate and a plurality of layers that form a laminate coating on said substrate; said method comprising: (a) providing a substrate; (b) forming a supercritical or near supercritical fluid solution comprising at least one supercritical fluid solvent and a first polymer, discharging said supercritical or near supercritical fluid solution under conditions sufficient to form solid particles of said first polymer, depositing said first polymer particles onto said substrate, wherein an electrical potential is maintained between the substrate and the first polymer, and sintering said first polymer; (c) depositing active agent particles in dry powder form onto said substrate, wherein an electrical potential is maintained between the substrate and said active agent particles, and wherein said active agent comprises at least one of extracellular matrix and an extracellular matrix component; and (d) forming a supercritical or near supercritical fluid solution comprising at least one supercritical fluid solvent and a second polymer and discharging said supercritical or near supercritical fluid solution under conditions sufficient to form solid particles of said second polymer, wherein an electrical potential is maintained between the substrate and the second polymer, and sintering said second polymer.

In some embodiments, step (c) and step (d) are repeated at least once. In some embodiments, steps (c) and step (d) are repeated 2 to 20 times.

In some embodiments, the active agent comprises at least one of extracellular matrix and an extracellular matrix component, wherein at least a portion of the active agent is in active form before the method begins, during the method steps, and when the method steps are complete.

In some embodiments, said first and second polymers are bioabsorbable. In some embodiments, said first and second polymers are durable.

In some embodiments, step (d) comprises forming a polymer layer having a length along a horizontal axis of said device wherein said polymer layer has a layer portion along said length, wherein said layer portion is free of active agent.

In some embodiments, sintering said first and/or sintering said second polymer comprises contacting said first and/or second polymer with a densified fluid.

In some embodiments, said contacting step is carried out for a period of from about 1 minute to about 60 minutes. In some embodiments, said contacting step is carried out for a period of from about 10 minutes to about 30 minutes.

In some embodiments, maintaining said electrical potential between said polymer particles and or active agent particles and said stent comprises maintaining a voltage of from about 5 kvolts to about 100 kvolts. In some embodiments, maintaining said electrical potential between said polymer particles and or active agent particles and said stent comprises maintaining a voltage of from about 20 kvolts to about 30 kvolts.

Provided herein is a device prepared by any process described herein.

Provided herein is a method of treating a subject comprising delivering a device described herein in a body lumen of the subject. Provided herein is a method of treating a subject comprising delivering a device described herein in a body of the subject.

Provided herein is a method of treating a subject comprising delivering in the body of the subject a device comprising: a stent; and a plurality of layers that form a laminate coating on said stent, wherein a first layer comprises a first polymer, a second layer comprises an active agent, a third layer comprises a second polymer, a fourth layer comprises the active agent, and a fifth layer comprises a third polymer, wherein the active agent comprises at least one of extracellular matrix and an extracellular matrix component, wherein at least a portion of the active agent is in active form, and wherein at least one of said first polymer, second polymer and third polymer comprises a PLGA copolymer. In some embodiments, the active agent is in active form before the method begins, during the method steps, and when the method steps are complete.

Provided herein is a method of treating a subject comprising delivering in the body of the subject a device comprising: a substrate; and a plurality of layers that form a laminate coating on said stent, wherein a first layer comprises a first polymer, a second layer comprises an active agent, a third layer comprises a second polymer, a fourth layer comprises the active agent, and a fifth layer comprises a third polymer, wherein the active agent comprises at least one of extracellular matrix and an extracellular matrix component, wherein at least a portion of the active agent is in active form, and wherein at least one of said first polymer, second polymer and third polymer comprises a PLGA copolymer. In some embodiments, the active agent is in active form before the method begins, during the method steps, and when the method steps are complete.

In some embodiments, said method comprises treating restenosis in a blood vessel of the subject.

Provided herein is a method of treating a subject comprising delivering in the body of the subject a device comprising: a stent; and a plurality of layers that form a laminate coating on said stent, wherein a first layer comprises a first polymer, a second layer comprises an active agent, a third layer comprises a second polymer, a fourth layer comprises the active agent, and a fifth layer comprises a third polymer, wherein the active agent comprises at least one of extracellular matrix and an extracellular matrix component, wherein at least a portion of the active agent is in active form, and wherein at least one of said first polymer, second polymer and third polymer comprises a durable polymer. In some embodiments, the active agent is in active form before the method begins, during the method steps, and when the method steps are complete.

Provided herein is a method of treating a subject comprising delivering in the body of the subject a device comprising: a substrate; and a plurality of layers that form a laminate coating on said substrate, wherein a first layer comprises a first polymer, a second layer comprises an active agent, a third layer comprises a second polymer, a fourth layer comprises the active agent, and a fifth layer comprises a third polymer, wherein the active agent comprises at least one of extracellular matrix and an extracellular matrix component, wherein at least a portion of the active agent is in active form, and wherein at least one of said first polymer, second polymer and third polymer comprises a durable polymer. In some embodiments, the active agent is in active form before the method begins, during the method steps, and when the method steps are complete.

In some embodiments, said method comprises treating restenosis in a blood vessel of the subject.

Provided herein is a device comprising: a stent; and a coating comprising an active agent comprising at least one of extracellular matrix and an extracellular matrix component, wherein at least a portion of the active agent is in active form, and a bioabsorbable polymer wherein the coating has an initial polymer amount; wherein when said device is delivered in a body lumen of a subject, at least about 75% of polymer is released from the device 90 days or more after the device is delivered in the body lumen of the subject.

In some embodiments, when said device is delivered in a body lumen of a subject about 75% of polymer is released from the device about 90 days after the device is delivered in the body lumen of the subject. In some embodiments, when said device is delivered in a body lumen of a subject about 85% of polymer is released from the device about 90 days after the device is delivered in the body lumen of the subject. In some embodiments, when said device is delivered in a body lumen of a subject about 100% of polymer is released from the device about 90 days after the device is delivered in the body lumen of the subject. In some embodiments, the active agent is in active form before the method begins, during the method steps, and when the method steps are complete.

In some embodiments, the subject is a pig and the amount of polymer released from the device is determined as follows: delivering the device in the pig's blood vessel lumen; euthanizing the pig at predetermined period of time after the device is delivered in the pig's blood vessel lumen and explanting the device; and measuring the amount of polymer released from the device. In some embodiments, measuring the amount of polymer released from the device comprises LC/MS/MS measurements. In some embodiments, measuring the amount released from the device comprises weight loss measurement. In some embodiments, weight loss measurement comprises measuring an amount of polymer remaining in the device and subtracting said remaining amount from the initial amount present in the device prior to delivering the device to the pig's blood vessel lumen.

Provided herein is a method of treating a subject comprising delivering a device as described herein in a body lumen.

In some embodiments, coating on an albuminal surface of said stent has a greater thickness than coating on a luminal surface of said stent. In some embodiments, a ratio of coating on the albuminal surface to coating on the luminal surface of the device is 80:20. In some embodiments, a ratio of coating on the albuminal surface to coating on the luminal surface of the device is 75:25. In some embodiments, a ratio of coating on the albuminal surface to coating on the luminal surface of the device is 70:30. In some embodiments, a ratio of coating on the albuminal surface to coating on the luminal surface of the device is 60:40.

In some embodiments, said stent is a coronary stent, a vascular stent, a peripheral stent, billiary stent, and intercranial stent.

Provided herein is a stent delivery system comprising: an elongate member having an inflation lumen and a guidewire lumen therein; a balloon having an interior that is in fluid communication with the inflation lumen; and a coated stent mounted on the balloon, wherein the coated stent comprises a stent and a plurality of layers that form a coating on said stent; wherein at least one of said layers comprises a polymer and at least one of said layers comprises an active agent, wherein the active agent comprises at least one of: extracellular matrix and an extracellular matrix component.

In some embodiments, the coating is a laminate coating.

In some embodiments, the extracellular matrix component comprises at least one of: heparin sulfate, chondroitin sulfate, keratan sulfate, hyaluronic acid, collagen, elastin, fibronectin, laminin, merosin, tenascin, vitronectin, and fibrillin.

In some embodiments, the polymer is at least one of: a bioabsorbable polymer and a durable polymer.

Provided herein is a method of preparing a stent delivery system comprising an elongate member having an inflation lumen and a guidewire lumen therein, a balloon having an interior that is in fluid communication with the inflation lumen, a stent and a plurality of layers that form a laminate coating on said stent; said method comprising: providing the stent; forming a coated stent by forming a plurality of layers to form said laminate coating on said stent; wherein at least one of said layers comprises a polymer and at least one of said layers comprises an active agent comprising at least one of extracellular matrix and an extracellular matrix component; and mounting the coated stent to the balloon, wherein said method creates at least one active agent layer on the stent, the active agent layer defined by a three-dimensional physical space occupied by the active agent and said three dimensional physical space is free of polymer.

Provided herein is a coated implantable medical device, comprising: a substrate; and a coating disposed on said substrate, wherein said coating comprises at least one polymer and an agent comprising at least one of extracellular matrix and an extracellular matrix component; wherein substantially all of the active agent remains within said coating and on said substrate until the implantable device is deployed at an intervention site inside the body of a subject, wherein upon deployment of said medical device in the body of said subject a portion of the active agent is delivered at said intervention site along with at least a portion of said polymer, and wherein the coated device is adapted to be delivered to a body lumen.

In some embodiments, upon deployment within the body of the subject, the coating partially or entirely dissociates from or is transferred from the device and the active agent is deposited at the site of placement of the device within the body along with at least a portion of said polymer. In some embodiments, the coating formulation provides at least one of: at least 10% deposition of the active agent within the body, at least 20% deposition of the active agent within the body, at least 30% deposition of the active agent within the body, at least 50% deposition of the active agent within the body, at least 75% deposition of the active agent within the body, at least 85% deposition of the active agent within the body, at least 90% deposition of the active agent within the body, at least 95% deposition of the active agent within the body, and at least 99% deposition of the active agent within the body.

In some embodiments, deposition is achieved within one day after deployment of the device within the body. In some embodiments, deposition is achieved instantaneously after deployment of the device within the body. In some embodiments, the coating dissociates from the substrate upon deployment of the device at the body site by plastic deformation of the coating, by compressive force, shear force, internally generated and/or externally generated force, shearing of the coating from the surface of the device, and/or bulk migration of the coating from the device into the tissue at the body site.

In some embodiments, the coating dissociates from the substrate through facile bulk flow under stress. In some embodiments, the coating comprises laminated layers that allow direct control of the transfer of plastic deformation, shear and bulk-migration.

In some embodiments, the extracellular matrix component comprises at least one of: heparin sulfate, chondroitin sulfate, keratan sulfate, hyaluronic acid, collagen, elastin, fibronectin, laminin, merosin, tenascin, vitronectin, and fibrillin.

In some embodiments, the substrate is an angioplasty balloon.

In some embodiments, the substrate is a cutting balloon.

In some embodiments, the coating comprises a soft material that undergoes plastic deformation at pressures provided by the inflation of the balloon. In some embodiments, the coating comprises a soft material that undergoes plastic deformation at pressures provided by the inflation of the balloon at 2-25 ATM. In some embodiments, the coating comprises a soft material that undergoes plastic deformation at pressures provided by the inflation of the balloon at 10-18 ATM.

In some embodiments, the coating comprises material that dissociates upon implant in the body in response to external stimuli. In some embodiments, stimuli comprise stimuli that induce a chemical transformation of the coating material. In some embodiments, the chemical transformation involves an acid base reaction. In some embodiments, the stimuli that induce a chemical transformation of the coating material comprise one or more of light, heat, and radiation. In some embodiments, the stimuli comprise stimuli that induce mechanical forces to augment the transfer of the coating into the tissue. In some embodiments, the stimuli that induce mechanical forces to augment the transfer of the coating into the tissue comprise ultrasound, translation, rotation, vibration and combinations thereof. In some embodiments, the coating comprises material that dissociates upon implant in the body in response to in-situ enzymatic reactions and/or material that dissociates upon implant in the body due to hydrolysis of the polymer, resulting in a week bond between the coating and the device.

In some embodiments, the at least one polymer is a durable polymer. In some embodiments, the durable polymer is selected from the group consisting of: polyester, aliphatic polyester, polyanhydride, polyethylene, polyorthoester, polyphosphazene, polyurethane, polycarbonate urethane, aliphatic polycarbonate, silicone, a silicone containing polymer, polyolefin, polyamide, polycaprolactam, polyamide, polyvinyl alcohol, acrylic polymer, acrylate, polystyrene, epoxy, polyethers, celluiosics, expanded polytetrafluoroethylene, phosphorylcholine, polyethyleneyerphthalate, polymethylmethavrylate, poly(ethylmethacrylate/n-butylmethacrylate), parylene C, polyethylene-co-vinyl acetate, polyalkyl methacrylates, polyalkylene-co-vinyl acetate, polyalkylene, polyalkyl siloxanes, polyhydroxyalkanoate, polyfluoroalkoxyphasphazine, poly(styrene-b-isobutylene-b-styrene), poly-butyl methacrylate, poly-bytadiene, and blends, combinations, homopolymers, condensation polymers, alternating, block, dendritic, cross-linked, and copolymers thereof.

In some embodiments, the coating comprises one or more resorbable polymers. In some embodiments, the one or more resorbable polymers are selected the group consisting of: PLGA (poly(lactide-co-glycolide); DLPLA—poly(dl-lactide); LPLA—poly(l-lactide); PGA—polyglycolide; PDO—poly(dioxanone); PGA-TMC—poly(glycolide-co-trimethylene carbonate); PGA-LPLA—poly(1-lactide-co-glycolide); PGA-DLPLA—poly(dl-lactide-co-glycolide); LPLA-DLPLA—poly(l-lactide-co-dl-lactide); and PDO-PGA-TMC—poly(glycolide-co-trimethylene carbonate-co-dioxanone). In some embodiments, the one or more resorbable polymers comprise between 1% and 95% glycolic acid content PLGA-based polymer. In some embodiments, the coating comprises a polymer having a dry modulus between 3,000 and 12,000 KPa.

In some embodiments, the coating comprises a hydrogel.

In some embodiments, the polymer film comprises a microstructure. In some embodiments, active agent particles are sequestered or encapsulated within said microstructure. In some embodiments, said microstructure comprises microchannels, micropores and/or microcavities.

In some embodiments, the coating is formed on said substrate through a process comprising depositing said polymer active agent by an e-RESS, an e-SEDS, or an e-DPC process. In some embodiments, forming said coating provides improved adherence of the coating to the substrate prior to deployment of the medical device at a body site and facilitates dissociation of said coating from said substrate after deployment of the medical device at said body site.

In some embodiments, the device is a cutting balloon having coated wire shaped in the form of an outward pointing wedge.

In some embodiments, the coating forms a sheath.

In some embodiments, the device comprises an inflatable balloon. In some embodiments, the coating comprises a soft material that undergoes plastic deformation at pressures provided by the inflation of the balloon. In some embodiments, the coating comprises a soft material that undergoes plastic deformation at pressures provided by the inflation of the balloon at 2-25 ATM. In some embodiments, the coating comprises a soft material that undergoes plastic deformation at pressures provided by the inflation of the balloon at 10-18 ATM.

In some embodiments, the polymer becomes soft after implantation. In some embodiments, the coating comprises a polymer that becomes soft after implant by hydration, degradation or by a combination of hydration and degradation.

In some embodiments, the device is adapted for delivery to at least one of a peripheral artery, a peripheral vein, a carotid artery, a vein, an aorta, and a biliary duct. In some embodiments, the device is adapted for delivery to a superficial femoral artery. In some embodiments, the device is adapted for delivery to a renal artery. In some embodiments, the device is adapted for delivery to an iliac artery. In some embodiments, the device is adapted for delivery to a bifurcated vessel. In some embodiments, the device is adapted for delivery to a vessel having a side branch at an intended delivery site of the vessel.

In some embodiments, the polymer is a durable polymer. In some embodiments, the polymer comprises a cross-linked durable polymer. In some embodiments, the polymer comprises a thermoset material. In some embodiments, the polymer comprises a cross-linked bioabsorbable polymer.

In some embodiments, the coating comprises a plurality of layers deposited on a device framework to form said device. In some embodiments, the plurality of layers comprises five layers deposited as follows: a first polymer layer, a first active agent layer, a second polymer layer, a second active agent layer and a third polymer layer. In some embodiments, the active agent and polymer are in the same layer; in separate layers or form overlapping layers. In some embodiments, the plurality of layers comprises at least 4 or more layers. In some embodiments, the plurality of layers comprises 10, 20, 50, or 100 layers. In some embodiments, the plurality of layers comprises at least one of: at least 10 layers, at least 20 layers, at least 50 layers, or at least 100 layers. In some embodiments, the plurality of layers comprises alternate active agent and polymer layers. In some embodiments, the active agent layers are substantially free of polymer and the polymer layers are substantially free of active agent. In some embodiments, the polymer provides radial strength for the device. In some embodiments, the polymer provides durability for the device. In some embodiments, the polymer is impenetrable by a broken piece of the device framework.

In some embodiments, the device is adapted for delivery to at least one of a peripheral artery, a peripheral vein, a carotid artery, a vein, an aorta, and a biliary duct.

Provided herein is a method of delivering a therapeutic agent to a site within the body of the subject comprising: providing a coated implantable medical device, comprising a substrate; and a coating disposed on said substrate, wherein said coating comprises at least one polymer and at least one active agent comprising at least one of extracellular matrix and an extracellular matrix component; wherein substantially all of the active agent remains within said coating and on said substrate until the implantable device is deployed at an intervention site inside the body of a subject and wherein upon deployment of said medical device in the body of said subject a portion of said active agent is delivered at said intervention site; and disposing the medical device at a selected site within the body of the subject, wherein the device is adapted for delivery to a body lumen.

In some embodiments, upon deployment within the body of the subject, the coating partially or entirely dissociates from the device and the active agent is deposited at the site of placement of the device within the body. In some embodiments, the coating formulation provides at least one of: at least 10% deposition of the active agent within the body, at least 20% deposition of the active agent within the body, at least 30% deposition of the active agent within the body, at least 50% deposition of the active agent within the body, at least 75% deposition of the active agent within the body, at least 85% deposition of the active agent within the body, at least 90% deposition of the active agent within the body, at least 95% deposition of the active agent within the body, and at least 99% deposition of the active agent within the body. In some embodiments, the coating dissociates from the substrate upon deployment of the device at the body site by plastic deformation of the coating, by compressive force, shear force, internally generated and/or externally generated force, shearing of the coating from the surface of the device, and/or bulk migration of the coating from the device into the tissue at the body site. In some embodiments, the method further comprises applying external stress so that the coating dissociates from the substrate through facile bulk flow under stress.

In some embodiments, the coating comprises biodegradable materials that are mechanically sound at the time of implant, then over time degrade to lose their cohesion and/or adhesion to the surface of the device.

In some embodiments, the extracellular matrix component comprises at least one of: heparin sulfate, chondroitin sulfate, keratan sulfate, hyaluronic acid, collagen, elastin, fibronectin, laminin, merosin, tenascin, vitronectin, and fibrillin.

In some embodiments, the substrate is an angioplasty balloon. In some embodiments, the substrate is a cutting balloon. In some embodiments, the coating comprises a soft material that undergoes plastic deformation at pressures provided by the inflation of the balloon and the method further comprises applying at pressures provided by the inflation of the balloon. In some embodiments, the method comprises applying the inflation of the balloon at 2-25 ATM.

In some embodiments, the coating comprises material that dissociates upon implant in the body in response to external stimuli. In some embodiments, the method comprises providing stimuli that induce a chemical transformation of the coating material. In some embodiments, the chemical transformation involves an acid base reaction. In some embodiments, the stimuli comprise one or more of light, heat, and radiation. In some embodiments, the method comprises providing stimuli that induce mechanical forces to augment the transfer of the coating into the tissue. In some embodiments, the stimuli that induce mechanical forces to augment the transfer of the coating into the tissue comprise ultrasound, translation, rotation, vibration and combinations thereof. In some embodiments, the coating comprises material that dissociates upon implant in the body in response to in-situ enzymatic reactions.

In some embodiments, the site in the body of the subject is the site of at least one of: a tumor or a void created by removal of tissue/tumor; vascular occlusion or stenosis; an infection; a wound; a diseased conduit in the body; and a conduit in the body fluidly connected to a disease site.

In some embodiments, the device is adapted for delivery to at least one of a superficial femoral artery, a renal artery, an iliac artery, and a bifurcated vessel a vessel having a side branch at an intended delivery site of the vessel. In some embodiments, the device is adapted for delivery to at least one of a peripheral artery, a peripheral vein, a carotid artery, a vein, an aorta, and a biliary duct.

Provided herein is a bioabsorbable device comprising a bioabsorbable substrate comprising a first active agent; and a coating on said substrate wherein the coating comprises a first polymer, wherein the first active agent comprises at least one of: extracellular matrix and an extracellular matrix component.

Provided herein is a bioabsorbable device comprising a bioabsorbable substrate; and a coating on said substrate wherein the coating comprises a first polymer and a first active agent, wherein the first active agent comprises at least one of: extracellular matrix and an extracellular matrix component.

In some embodiments, the extracellular matrix component comprises at least one of: heparin sulfate, chondroitin sulfate, keratan sulfate, hyaluronic acid, collagen, elastin, fibronectin, laminin, merosin, tenascin, vitronectin, and fibrillin.

In some embodiments, the bioabsorbable device is a bioabsorbable stent. In some embodiments, the bioabsorbable substrate comprises a bioabsorbable metal framework. In some embodiments, the bioabsorbable metal framework comprises magnesium. In some embodiments, the first polymer degrades by bulk erosion. In some embodiments, the bioabsorbable substrate comprises a second polymer. In some embodiments, the first polymer and the second polymer are the same polymer. In some embodiments, the second polymer degrades by surface erosion. In some embodiments the first polymer degrades by surface erosion.

In some embodiments, the coating comprises a second active agent. In some embodiments, the bioabsorbable substrate comprises a second active agent. In some embodiments, the second active agent comprises at least one of a pharmaceutical agent and a biologic agent. In some embodiments, the pharmaceutical agent comprises a macrolide immunosuppressive (limus) drug. In some embodiments, the macrolide immunosuppressive (limus) drug comprises one or more of: rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4 (S)-yl)-prop-2'-en-1'-yl]-rapamycin, (2':E,4'S)-40-O-(4',5'-Dihydroxypent-2'-en-1'-yl)-rapamycin, 40-O-(2-Hydroxy) ethoxycar-bonylmethyl-rapamycin, 40-O-(3-Hydroxy) propyl-rapamycin, 40-O-(6-Hydroxy)hexyl-rapamycin, 40-O-[2-(2-Hydroxy)ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy) ethyl-rapamycin, 40-O-(2-Nicotinoyloxy)ethyl-rapamycin, 40-O-[2-(N-Morpholino)acetoxy]ethyl-rapamycin, 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin, 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof.

In some embodiments, the device is delivered to a target tissue and returns endothelial function to the target tissue at 28 days from device delivery. In some embodiments, the endothelial function is determined using Rapid Atrial Pacing. In some embodiments, the endothelial function is determined using acetylcholine challenge testing in an animal model. In some embodiments, the endothelial function is determined by detection of eNOS protein in an animal model.

Provided herein is a method of preparing a bioabsorbable device; said method comprising: providing a bioabsorbable substrate comprising a first active agent; and forming a coating on said substrate wherein the coating comprises a first polymer, wherein at least a portion of the active agent comprises at least one of extracellular matrix and an extracellular matrix component.

Provided herein is a method of preparing a bioabsorbable device; said method comprising providing a bioabsorbable substrate; and forming a coating on said substrate wherein the coating comprises a first polymer and a first active agent, wherein the first active agent comprises at least one of: extracellular matrix and an extracellular matrix component.

In some embodiments, the extracellular matrix component comprises at least one of: heparin sulfate, chondroitin sulfate, keratan sulfate, hyaluronic acid, collagen, elastin, fibronectin, laminin, merosin, tenascin, vitronectin, and fibrillin.

In some embodiments, the bioabsorbable device is a bioabsorbable stent. In some embodiments, the bioabsorbable substrate comprises a bioabsorbable metal framework. In some embodiments, the bioabsorbable metal framework comprises magnesium. In some embodiments, the first polymer degrades by bulk erosion. In some embodiments, the bioabsorbable substrate comprises a second polymer. In some embodiments, the first polymer and the second polymer are the same polymer. In some embodiments, the second polymer degrades by surface erosion. In some embodiments the first polymer degrades by surface erosion.

In some embodiments, the coating comprises a second active agent. In some embodiments, the bioabsorbable substrate comprises a second active agent. In some embodiments, the second active agent comprises at least one of a pharmaceutical agent and a biologic agent. In some embodiments, the pharmaceutical agent comprises a macrolide immunosuppressive (limus) drug. In some embodiments, the macrolide immunosuppressive (limus) drug comprises one or more of: rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4 (S)-yl)-prop-2'-en-1'-yl]-rapamycin, (2':E,4'S)-40-O-(4',5'-Dihydroxypent-2'-en-1'-yl)-rapamycin, 40-O-(2-Hydroxy)ethoxycar-bonylmethyl-rapamycin, 40-O-(3-Hydroxy)propyl-rapamycin, 40-O-(6-Hydroxy)hexyl-rapamycin, 40-O-[2-(2-Hydroxy)ethoxy]ethyl-rapamycin, 40-O-[(3 S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin, 40-O-(2-Nicotinoyloxy)ethyl-rapamycin, 40-O-[2-(N-Morpholino)acetoxy]ethyl-rapamycin, 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin, 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof.

In some embodiments, the device is delivered to a target tissue and returns endothelial function to the target tissue at 28 days from device delivery. In some embodiments, the endothelial function is determined using Rapid Atrial Pacing. In some embodiments, the endothelial function is determined using acetylcholine challenge testing in an animal model. In some embodiments, the endothelial function is determined by detection of eNOS protein in an animal model.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
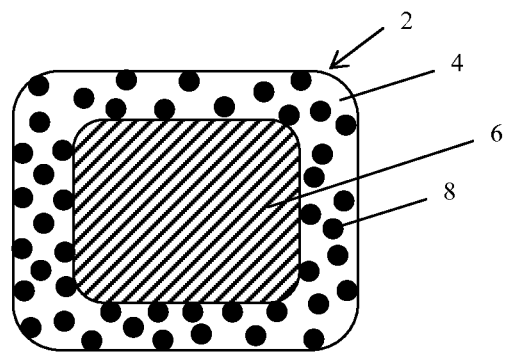
FIG. 1 depicts a cross sectional view of a device according to an embodiment herein, for non-limiting example, a stent strut, comprising a substrate coated with a polymer and ECM or at least one ECM component.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments contemplated herein will be apparent to those skilled in the art in light of the instant disclosure, which do not depart from the instant invention. Hence, the following specification is intended to illustrate selected embodiments of the invention, and not to exhaustively specify all permutations, combinations and variations thereof.

Definitions

As used in the present specification, the following words and phrases are generally intended to have the meanings as set forth below, except to the extent that the context in which they are used indicates otherwise.

"Substrate" as used herein, refers to any surface upon which it is desirable to deposit a coating comprising a polymer and a pharmaceutical or biological agent, wherein the coating process does not substantially modify the morphology of the pharmaceutical agent or the activity of the biological agent. Biomedical implants are of interest for the present invention; however the present invention is not intended to be restricted to this class of substrates. Interventional devices are also of interest for the present invention; however the present invention is not intended to be restricted to this class of substrates. Diagnostic devices are also of interest for the present invention; however the present invention is not intended to be restricted to this class of substrates. Those of skill in the art will appreciate alternate substrates that could benefit from the coating process described herein, such as pharmaceutical tablet cores, as part of an assay apparatus or as components in a diagnostic kit (e.g. a test strip).

"Biomedical implant" as used herein refers to any implant for insertion into the body of a human or animal subject, including but not limited to stents (e.g., coronary stents, vascular stents including peripheral stents and graft stents, urinary tract stents, urethral/prostatic stents, rectal stent, oesophageal stent, biliary stent, pancreatic stent), electrodes, catheters, leads, implantable pacemaker, cardioverter or defibrillator housings, joints, screws, rods, ophthalmic implants, femoral pins, bone plates, grafts, anastomotic devices, perivascular wraps, sutures, staples, shunts for hydrocephalus, dialysis grafts, colostomy bag attachment devices, ear drainage tubes, leads for pace makers and implantable cardioverters and defibrillators, vertebral disks, bone pins, suture anchors, hemostatic barriers, clamps, screws, plates, clips, vascular implants, tissue adhesives and sealants, tissue scaffolds, various types of dressings (e.g., wound dressings), bone substitutes, intraluminal devices, vascular supports, etc. In some embodiments, the substrate is selected from the group consisting of: stents, joints, screws, rods, pins, plates, staples, shunts, clamps, clips, sutures, suture anchors, electrodes, catheters, leads, grafts, dressings, pacemakers, pacemaker housings, cardioverters, cardioverter housings, defibrillators, defibrillator housings, prostheses, ear drainage tubes, ophthalmic implants, orthopedic devices, vertebral disks, bone substitutes, anastomotic devices, perivascular wraps, colostomy bag attachment devices, hemostatic barriers, vascular implants, vascular supports, tissue adhesives, tissue sealants, tissue scaffolds and intraluminal devices. The implant may be temporarily used in or permanently implanted in the body of a human or animal subject. The implant may only be used in a transient manner in or on the body of the subject, for non-limiting example: during a medical procedure that does not leave the implant in or on the subject once the medical procedure is completed.

The implants may be formed from any suitable material, including but not limited to polymers (including stable or inert polymers, organic polymers, organic-inorganic copolymers, inorganic polymers, and biodegradable polymers), metals, metal alloys, inorganic materials such as silicon, and composites thereof, including layered structures with a core of one material and one or more coatings of a different material. Substrates made of a conducting material facilitate electrostatic capture. However, the invention contemplates the use of electrostatic capture, as described below, in conjunction with substrate having low conductivity or which are non-conductive. To enhance electrostatic capture when a non-conductive substrate is employed, the substrate is processed for example while maintaining a strong electrical field in the vicinity of the substrate.

In some embodiments, the implant comprises a stainless steel material. In some embodiments, the implant comprises a material comprising a cobalt chromium alloy. In some embodiments, the implant comprises a material comprising the following percentages by weight: about 0.05 to about 0.15 C, about 1.00 to about 2.00 Mn, about 0.04 Si, about 0.03 P, about 0.3 S, about 19.0 to about 21.0 Cr, about 9.0 to about 11.0 Ni, about 14.0 to about 16.00 W, about 3.0 Fe, and Bal. Co. In some embodiments, the implant comprises a material comprising at most the following percentages by weight: about 0.025 C, about 0.15 Mn, about 0.15 Si, about 0.015 P, about 0.01 S, about 19.0 to about 21.0 Cr, about 33 to about 37 Ni, about 9.0 to about 10.5 Mo, about 1.0 Fe, about 1.0 Ti, and Bal. Co. In some embodiments, the implant comprises a material comprising L605 alloy. In some embodiments, the implant comprises a material comprising a platinum chromium alloy instead of a cobalt-chromium alloy. In some embodiments, the implant comprises a material comprising MP35N alloy. In some embodiments, the implant comprises a material comprising the following percentages by weight: about 35 Ni, about 35Cr, about 20 Co, and about 10 Mo. In some embodiments, the implant comprises a material comprising a cobalt chromium nickel alloy. In some embodiments, the implant comprises a material comprising Elgiloy®/Phynox®. In some embodiments, the implant comprises a material comprising the following percentages by weight: about 39 to about 41 Co, about 19 to about 21 Cr, about 14 to about 16 Ni, about 6 to about 8 Mo, and Balance Fe. In some embodiments, the implant comprises a material comprising a platinum chromium alloy. In some embodiments, the implant comprises an alloy as described in U.S. Pat. No. 7,329,383 incorporated in its entirety herein by reference. In some embodiments, the implant comprises an alloy as described in U.S. patent application Ser. No. 11/780,060 incorporated in its entirety herein by reference. In some embodiments, the implant comprises a material comprising stainless steel, 316L stainless steel, BioDur® 108 (UNS S29108), 304L stainless steel, and an alloy including stainless steel and 5-60% by weight of one or more radiopaque elements such as Pt, IR, Au, W, PERSS® as described in U.S. Publication No. 2003/001830 incorporated in its entirety herein by reference, U.S. Publication No. 2002/0144757 incorporated in its entirety herein by reference, and U.S. Publication No. 2003/0077200 incorporated in its entirety herein by reference, nitinol, a nickel-titanium alloy, cobalt alloys, Elgiloy®, L605 alloys, MP35N alloys, titanium, titanium alloys, Ti-6Al-4V, Ti-50Ta, Ti-10Ir, platinum, platinum alloys, niobium, niobium alloys, Nb-1Zr, Co-28Cr-6Mo, tantalum, and tantalum alloys. Other examples of materials that are comprised in the device (or substrate thereof) are described in U.S. Publication No. 2005/0070990 incorporated in its entirety herein by reference, and U.S. Publication No. 2006/0153729 incorporated in its entirety herein by reference. Other materials include elastic biocompatible metal such as superelastic or pseudo-elastic metal alloys, as described, for example in Schetsky, L. McDonald, "Shape Memory Alloys", Encyclopedia of Chemical Technology (3d Ed), John Wiley & Sons 1982, vol. 20 pp. 726-736 incorporated herein by reference, and U.S. Publication No. 2004/0143317 incorporated in its entirety herein by reference.

Subjects into which biomedical implants of the invention may be applied or inserted include both human subjects (including male and female subjects and infant, juvenile, adolescent, adult and geriatric subjects) as well as animal subjects (including but not limited to pig, rabbit, mouse, dog, cat, horse, monkey, etc.) for veterinary purposes and/or medical research.

In a preferred embodiment the biomedical implant is an expandable intraluminal vascular graft or stent (e.g., comprising a wire mesh tube) that can be expanded within a blood vessel by an angioplasty balloon associated with a catheter to dilate and expand the lumen of a blood vessel, such as described in U.S. Pat. No. 4,733,665 to Palmaz.

In some embodiments, the substrate is an interventional device. An "interventional device" as used herein refers to any device for insertion into the body of a human or animal subject, which may or may not be left behind (implanted) for any length of time including, but not limited to, angioplasty balloons, cutting balloons.

In some embodiments, the substrate is a diagnostic device. A "diagnostic device" as used herein refers to any device for insertion into the body of a human or animal subject in order to diagnose a condition, disease or other of the patient, or in order to assess a function or state of the body of the human or animal subject, which may or may not be left behind (implanted) for any length of time.

In some embodiments, the substrate is a surgical tool. A "surgical tool" as used herein refers to a tool used in a medical procedure that may be inserted into (or touch) the body of a human or animal subject in order to assist or participate in that medical procedure.

"Pharmaceutical agent" as used herein refers to any of a variety of drugs or pharmaceutical compounds that can be used as active agents to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). It is possible that the pharmaceutical agents of the invention may also comprise two or more drugs or pharmaceutical compounds. Pharmaceutical agents, include but are not limited to those noted in Ser. No. 12/751,902 filed Mar. 31, 2010, Ser. No. 12/762,007 filed Apr. 16, 2010, and 61/243,955 filed Sep. 18, 2009, each of which is titled: Stents Having Bioabsorbable Layers, and all of which are incorporated herein in their entirety by reference.

In some embodiments, the device has an active agent content of from about 5 µg to about 500 µg. In some embodiments, device has an active agent content of from about 100 µg to about 160 µg.

"Pharmaceutical agent" as used herein refers to any of a variety of drugs or pharmaceutical compounds that can be used as active agents to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). It is possible that the pharmaceutical agents of the invention may also comprise two or more drugs or pharmaceutical compounds. Pharmaceutical agents, include but are not limited to antirestenotic agents, antidiabetics, analgesics, antiinflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti parkinson agents, thyroid therapeutic agents, spasmolytics, platelet aggregation inhibitors, vitamins, cytostatics and metastasis inhibitors, phytopharmaceuticals, chemotherapeutic agents and amino acids. Examples of suitable active ingredients are acarbose, antigens, beta-receptor blockers, non-steroidal antiinflammatory drugs [NSAIDs], cardiac glycosides, acetylsalicylic acid, virustatics, aclarubicin, acyclovir, cisplatin, actinomycin, alpha- and beta-sympatomimetics, (dimeprazole, allopurinol, alprostadil, prostaglandins, amantadine, ambroxol, amlodipine, methotrexate, S-aminosalicylic acid, amitriptyline, amoxicillin, anastrozole, atenolol, azathioprine, balsalazide, beclomethasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cefalosporins, cetirizine, chenodeoxycholic acid, ursodeoxycholic acid, theophylline and theophylline derivatives, trypsins, cimetidine, clarithromycin, clavulanic acid, clindamycin, clobutinol, clonidine, cotrimoxazole, codeine, caffeine, vitamin D and derivatives of vitamin D, colestyramine, cromoglicic acid, coumarin and coumarin derivatives, cysteine, cytarabine, cyclophosphamide, ciclosporin, cyproterone, cytabarine, dapiprazole, desogestrel, desonide, dihydralazine, diltiazem, ergot alkaloids, dimenhydrinate, dimethyl sulphoxide, dimethicone, domperidone and domperidan derivatives, dopamine, doxazosin, doxorubizin, doxylamine, dapiprazole, benzodiazepines, diclofenac, glycoside antibiotics, desipramine, econazole, ACE inhibitors, enalapril, ephedrine, epinephrine, epoetin and epoetin derivatives, morphinans, calcium antagonists, irinotecan, modafinil, orlistat, peptide antibiotics, phenyloin, riluzoles, risedronate, sildenafil, topiramate, macrolide antibiotics, oestrogen and oestrogen derivatives, progestogen and progestogen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitors, fluconazole, fludarabine, fluarizine, fluorouracil, fluoxetine, flurbiprofen, ibuprofen, flutamide, fluvastatin, follitropin, formoterol, fosfomicin, furosemide, fusidic acid, gallopamil, ganciclovir, gemfibrozil, gentamicin, ginkgo, Saint John's wort, glibenclamide, urea derivatives as oral antidiabetics, glucagon, glucosamine and glucosamine derivatives, glutathione, glycerol and glycerol derivatives, hypothalamus hormones, goserelin, gyrase inhibitors, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramine, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mepindolol, meprobamate, meropenem, mesalazine, mesuximide, metamizole, metformin, methotrexate, methylphenidate, methylprednisolone, metixene, metoclopramide, metoprolol, metronidazole, mianserin, miconazole, minocycline, minoxidil, misoprostol, mitomycin, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, oxaceprol, oxacillin, oxiconazole, oxymetazoline, pantoprazole, paracetamol, paroxetine, penciclovir, oral penicillins, pentazocine, pentifylline, pentoxifylline, perphenazine, pethidine, plant extracts, phenazone, pheniramine, barbituric acid derivatives, phenylbutazone, phenyloin, pimozide, pindolol, piperazine, piracetam, pirenzepine, piribedil, piroxicam, pramipexole, pravastatin, prazosin, procaine, promazine, propiverine, propranolol, propyphenazone, prostaglandins, protionamide, proxyphylline, quetiapine, quinapril, quinaprilat, ramipril, ranitidine, reproterol, reserpine, ribavirin, rifampicin, risperidone, ritonavir, ropinirole, roxatidine, roxithromycin, ruscogenin, rutoside and rutoside derivatives, sabadilla, salbutamol, salmeterol, scopolamine, selegiline, sertaconazole, sertindole, sertralion, silicates, sildenafil, simvastatin, sitosterol, sotalol, spaglumic acid, sparfloxacin, spectinomycin, spiramycin, spirapril, spironolactone, stavudine, streptomycin, sucralfate, sufentanil, sulbactam, sulphonamides, sulfasalazine, sulpiride, sultamicillin, sultiam, sumatriptan, suxamethonium chloride, tacrine, tacrolimus, taliolol, tamoxifen, taurolidine, tazarotene, temazepam, teniposide, tenoxicam, terazosin, terbinafine, terbutaline, terfenadine, terlipressin, tertatolol, tetracyclins, teryzoline, theobromine, theophylline, butizine, thiamazole, phenothiazines, thiotepa, tiagabine, tiapride, propionic acid derivatives, ticlopidine, timolol, timidazole, tioconazole, tioguanine, tioxolone, tiropramide, tizanidine, tolazoline, tolbutamide, tolcapone, tolnaftate, tolperisone, topotecan, torasemide, antioestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpin, troxerutine, tulobuterol, tyramine, tyrothricin, urapidil, ursodeoxycholic acid, chenodeoxycholic acid, valaciclovir, valproic acid, vancomycin, vecuronium chloride, Viagra, venlafaxine, verapamil, vidarabine, vigabatrin, viloazine, vinblastine, vincamine, vincristine, vindesine, vinorelbine, vinpocetine, viquidil, warfarin, xantinol nicotinate, xipamide, zafirlukast, zalcitabine, zidovudine, zolmitriptan, zolpidem, zoplicone, zotipine and the like. See, e.g., U.S. Pat. No. 6,897,205; see also U.S. Pat. No. 6,838,528; U.S. Pat. No. 6,497,729, incorporated herein by reference in their entirety.

In some embodiments, the pharmaceutical agent is selected from one or more of sirolimus, everolimus, zotarolimus and biolimus. In some embodiments, the pharmaceutical agent comprises a macrolide immunosuppressive (limus) drug. In some embodiments, the macrolide immunosuppressive drug comprises one or more of: rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E, 4'S)-40-O-(4',5'-Dihydroxypent-2'-en-1'-yl)-rapamycin, 40-O-(2-Hydroxy)ethoxycar-bonylmethyl-rapamycin, 40-O-(3-Hydroxy)propyl-rapamycin, 40-O-(6-Hydroxy)hexyl-rapamycin, 40-O-[2-(2-Hydroxy)ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin, 40-O-(2-Nicotinoyloxy)ethyl-rapamycin, 40-O-[2-(N-Morpholino)acetoxy]ethyl-rapamycin, 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin, 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof.

As used herein, the pharmaceutical agent sirolimus may also and/or alternatively be called rapamycin, or vice versa, unless otherwise noted with regard to a particular term—for nonlimiting example, 42-Epi-(tetrazolyl)rapamycin is tacrolimus as noted herein.

The pharmaceutical agents may, if desired, also be used in the form of their pharmaceutically acceptable salts or derivatives (meaning salts which retain the biological effectiveness and properties of the compounds of this invention and which are not biologically or otherwise undesirable), and in the case of chiral active ingredients it is possible to employ both optically active isomers and racemates or mixtures of diastereoisomers. As well, the pharmaceutical agent may include a prodrug, a hydrate, an ester, a derivative or analogs of a compound or molecule. In some embodiments, the pharmaceutical agent is selected from a prodrug, a derivative, an analog, a hydrate, an ester, and a salt of another pharmaceutical agent.

In some embodiments, the pharmaceutical agent is, at least in part, crystalline. As used herein, the term crystalline may include any number of the possible polymorphs of the crystalline form of the pharmaceutical agent, including for non-limiting example a single polymorph of the pharmaceutical agent, or a plurality of polymorphs of the pharmaceutical agent. The crystalline pharmaceutical agent (which may include a semi-crystalline form of the pharmaceutical agent, depending on the embodiment) may comprise a single polymorph of the possible polymorphs of the pharmaceutical agent. The crystalline pharmaceutical agent (which may include a semi-crystalline form of the pharmaceutical agent, depending on the embodiment) may comprise a plurality of polymorphs of the possible polymorphs of the crystalline pharmaceutical agent. The polymorph, in some embodiments, is a packing polymorph, which exists as a result of difference in crystal packing as compared to another polymorph of the same crystalline pharmaceutical agent. The polymorph, in some embodiments, is a conformational polymorph, which is conformer of another polymorph of the same crystalline pharmaceutical agent. The polymorph, in some embodiments, is a pseudopolymorph. The polymorph, in some embodiments, is any type of polymorph—that is, the type of polymorph is not limited to only a packing polymorph, conformational polymorph, and/or a pseudopolymorph. When referring to a particular pharmaceutical agent herein which is at least in part crystalline, it is understood that any of the possible polymorphs of the pharmaceutical agent are contemplated.

The pharmaceutical agents may, if desired, also be used in the form of their pharmaceutically acceptable salts or derivatives (meaning salts which retain the biological effectiveness and properties of the compounds of this invention and which are not biologically or otherwise undesirable), and in the case of chiral active ingredients it is possible to employ both optically active isomers and racemates or mixtures of diastereoisomers. As well, the pharmaceutical agent may include a prodrug, a hydrate, an ester, a derivative or analogs of a compound or molecule.

A "pharmaceutically acceptable salt" may be prepared for any pharmaceutical agent having a functionality capable of forming a salt, for example an acid or base functionality. Pharmaceutically acceptable salts may be derived from organic or inorganic acids and bases. The term "pharmaceutically-acceptable salts" in these instances refers to the relatively non-toxic, inorganic and organic base addition salts of the pharmaceutical agents.

"Prodrugs" are derivative compounds derivatized by the addition of a group that endows greater solubility to the compound desired to be delivered. Once in the body, the prodrug is typically acted upon by an enzyme, e.g., an esterase, amidase, or phosphatase, to generate the active compound.

"Stability" as used herein in refers to the stability of the drug in a polymer coating deposited on a substrate in its final product form (e.g., stability of the drug in a coated stent). The term stability will define 5% or less degradation of the drug in the final product form.

"Active biological agent" as used herein refers to a substance, originally produced by living organisms, that can be used to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). It is possible that the active biological agents of the invention may also comprise two or more active biological agents or an active biological agent combined with a pharmaceutical agent, a stabilizing agent or chemical or biological entity. Although the active biological agent may have been originally produced by living organisms, those of the present invention may also have been synthetically prepared, or by methods combining biological isolation and synthetic modification. By way of a non-limiting example, a nucleic acid could be isolated form from a biological source, or prepared by traditional techniques, known to those skilled in the art of nucleic acid synthesis. Furthermore, the nucleic acid may be further modified to contain non-naturally occurring moieties. Non-limiting examples of active biological agents include peptides, proteins, enzymes, glycoproteins, nucleic acids (including deoxyribonucleotide or ribonucleotide polymers in either single or double stranded form, and unless otherwise limited, encompasses known analogues of natural nucleotides that hybridize to nucleic acids in a manner similar to naturally occurring nucleotides), antisense nucleic acids, fatty acids, antimicrobials, vitamins, hormones, steroids, lipids, polysaccharides, carbohydrates and the like. They further include, but are not limited to, antirestenotic agents, antidiabetics, analgesics, antiinflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti parkinson agents, thyroid therapeutic agents, spasmolytics, platelet aggregation inhibitors, vitamins, cytostatics and metastasis inhibitors, phytopharmaceuticals and chemotherapeutic agents. Preferably, the active biological agent is a peptide, protein or enzyme, including derivatives and analogs of natural peptides, proteins and enzymes. The active biological agent may also be a hormone, gene therapies, RNA, siRNA, and/or cellular therapies (for non-limiting example, stem cells or T-cells). An active agent may be (or comprise) extracellular matrix and/or an extracellular matrix component.

"Active agent" as used herein refers to any pharmaceutical agent or active biological agent as described herein.

"Activity" as used herein refers to the ability of a pharmaceutical or active biological agent to prevent or treat a disease (meaning any treatment of a disease in a mammal, including preventing the disease, i.e. causing the clinical symptoms of the disease not to develop; inhibiting the disease, i.e. arresting the development of clinical symptoms; and/or relieving the disease, i.e. causing the regression of clinical symptoms). Thus the activity of a pharmaceutical or active biological agent should be of therapeutic or prophylactic value. An active agent that has activity as noted herein may be referred to as being in "active form."

"Secondary, tertiary and quaternary structure" as used herein are defined as follows. The active biological agents of the present invention will typically possess some degree of secondary, tertiary and/or quaternary structure, upon which the activity of the agent depends. As an illustrative, non-limiting example, proteins possess secondary, tertiary and quaternary structure. Secondary structure refers to the spatial arrangement of amino acid residues that are near one another in the linear sequence. The α-helix and the β-strand are elements of secondary structure. Tertiary structure refers to the spatial arrangement of amino acid residues that are far apart in the linear sequence and to the pattern of disulfide bonds. Proteins containing more than one polypeptide chain exhibit an additional level of structural organization. Each polypeptide chain in such a protein is called a subunit. Quaternary structure refers to the spatial arrangement of subunits and the nature of their contacts. For example hemoglobin consists of two α and two β chains. It is well known that protein function arises from its conformation or three dimensional arrangement of atoms (a stretched out polypeptide chain is devoid of activity). Thus one aspect of the present invention is to manipulate active biological agents, while being careful to maintain their conformation, so as not to lose their therapeutic activity.

"Extracellular matrix" or "ECM" as used herein is a complex structural entity surrounding and supporting cells that are found within mammalian tissues. "Extracellular matrix component" as used herein comprises at least one of: heparin sulfate, chondroitin sulfate, keratan sulfate, hyaluronic acid, collagen, elastin, fibronectin, laminin, merosin, tenascin, vitronectin, and fibrillin.

In mammalian tissues the ECM is most commonly found in connective tissues such as tendon, cartilage, bone or dermis of the skin. The ECM is often referred to as the connective tissue. The extracellular matrix includes the interstitial matrix and the basement membrane. Interstitial matrix is present between various animal cells (i.e., in the intercellular spaces). Gels of polysaccharides and fibrous proteins fill the interstitial space and act as a compression buffer against the stress placed on the ECM.

Basement membranes are sheet-like depositions of ECM on which various epithelial cells rest. The basement membrane surrounding the blood vessel endothelium is a thin specialized network of extracellular matrix (ECM) proteins that serves many functions. Composed of proteins and proteoglycans, such as collagen, laminin, entactin, fibronectin, heparin sulfate and perlecan, this membrane acts as a physical barrier between the epithelium and underlying tissues. It provides cell surface anchorage (via integrins, receptor kinases, and cell surface proteoglycans), induces cellular differentiation, gives architectural support, and limits the migration of normal cells. The ability of tumor cells to degrade the ECM components of the basement membrane and surrounding tissues is directly correlated with metastatic potential. By releasing proteolytic enzymes (e.g. MMP collagenases, plasminogen activators, cathepsins), cancer cells are able to breach the membrane and penetrate the blood vessel wall. Collagen, the primary structural element of the basement membrane and tissue scaffolding protein, represents the main deterrent in the migration of tumor cells.

Changes in the amount and organization of the ECM components change the type and form of the ECM. The ECM is produced and maintained by the cells that inhabit it. The proteins within the ECM can be divided into several classes (i.e. classes of biomolecules) based upon their structure and function within the ECM. The most prominent class is the structural class of ECM proteins. These consist primarily of the collagen and elastin families of proteins. Collagen fibers strengthen and organize the matrix; elastin fibers provide flexibility and resilience. Another class is of specialized proteins, such as fibrillin, fibronectin, laminin, merosin, tenascin, and vitronectin serve less of a structural role and more of an adhesive or integral role within the ECM matrix; these proteins allow for cell attachment and form crosslinks within the matrix gel. Finally, numerous proteoglycans and heparan sulfate containing proteins form the highly hydrated gel-like mixture that helps stabilize the matrix within its aqueous environment. Proteoglycans are comprised of a protein core to which is attached long chains of glycosaminoglycans (GAGs) forming extremely complex high molecular weight components of the ECM. Another GAG which is a component of ECM is hyaluronic acid, a non-sulfate GAG.

Due to its diverse nature and composition, the ECM can serve many functions, such as providing support and anchorage for cells, segregating tissues from one another, and regulating intercellular communication. The ECM regulates a cell's dynamic behavior. In addition, it sequesters a wide range of cellular growth factors, and acts as a local depot for them. Changes in physiological conditions can trigger protease activities that cause local release of such depots. This allows the rapid and local growth factor-mediated activation of cellular functions, without de novo synthesis.

Formation of the extracellular matrix is used for processes like growth, wound healing and fibrosis. An understanding of ECM structure and composition also helps in comprehending the dynamics of tumor invasion and metastasis in cancer biology as metastasis often involves the destruction of extracellular matrix by enzymes such as serine and threonine proteases and matrix metalloproteinase.

Components of the ECM are produced intracellularly by resident cells, and secreted into the ECM via exocytosis. Once secreted they then aggregate with the existing matrix. The ECM is composed of an interlocking mesh of fibrous proteins and glycosaminoglycans (GAGs).

Glycosaminoglycans (GAGs) are the most abundant heteropolysaccharides in the body. GAGs are carbohydrate polymers and are usually attached to extracellular matrix proteins to form proteoglycans (hyaluronic acid is a notable exception, see below). These molecules are long unbranched polysaccharides containing a repeating disaccharide unit. The disaccharide units contain either of two modified sugars, N-acetylgalactosamine (GalNAc) or N-acetylglucosamine (GlcNAc), and a uronic acid such as glucuronate or iduronate. GAGs are highly negatively charged molecules, with extended conformation that imparts high viscosity to the solution. GAGs are located primarily on the surface of cells or in the extracellular matrix (ECM). Along with the high viscosity of GAGs comes low compressibility, which makes these molecules ideal for a lubricating fluid in the joints. At the same time, their rigidity provides structural integrity to cells and provides passageways between cells, allowing for cell migration. The specific GAGs of physiological significance are hyaluronic acid, dermatan sulfate, chondroitin sulfate, heparin, heparan sulfate, and keratan sulfate.

The majority of GAGs in the body are linked to core proteins, forming proteoglycans (also called mucopolysaccharides). The GAGs extend perpendicularly from the core in a brush-like structure. The linkage of GAGs to the protein core involves a specific trisaccharide composed of two galactose residues and a xylose residue (GAG-GalGalXyl-O—CH$_2$-protein). The trisaccharide linker is coupled to the protein core through an O-glycosidic bond to a S residue in the protein. The protein cores of proteoglycans are rich in S and T residues, which allows multiple GAG attachments.

Proteoglycans have a net negative charge that attracts water molecules, keeping the ECM and resident cells hydrated. Proteoglycans may also help to trap and store growth factors within the ECM. Different types of proteoglycan which are components of the extracellular matrix and are found within the extracellular matrix include Heparin Sulfate, Chondroitin Sulfate, and Keratan Sulfate.

Heparan sulfate (HS) is a linear polysaccharide found in all animal tissues. It occurs as a proteoglycan (PG) in which two or three HS chains are attached in close proximity to cell surface or extracellular matrix proteins. It is in this form that HS binds to a variety of protein ligands and regulates a wide variety of biological activities, including developmental processes, angiogenesis, blood coagulation and tumour metastasis.

In the extracellular matrix, especially basement membranes, the multi-domain proteins perlecan, agrin and collagen XVIII are the main proteins to which heparan sulfate is attached.

Chondroitin sulfates contribute to the tensile strength of cartilage, tendons, ligaments and walls of the aorta. They have also been known to affect neuroplasticity.

Keratan sulfates have a variable sulfate content and unlike many other GAGs, do not contain uronic acid. They are present in the cornea, cartilage, bones and the horns of animals.

A non-proteoglycan polysaccharide component of the ECM is hayaluronic acid. Hyaluronic acid (or "hyaluronan" or "hyaluronate" and may also or alternatively be used in its salt form i.e. as sodium hyaluronate) is a polysaccharide consisting of alternative residues of D-glucuronic acid and N-acetylglucosamine, and unlike other GAGs is not found as a proteoglycan. Hyaluronic is unique among the GAGs in that it does not contain any sulfate and is not found covalently attached to proteins as a proteoglycan. It is, however, a component of non-covalently formed complexes with proteoglycans in the ECM. Hyaluronic acid in the extracellular space confers upon tissues the ability to resist compression by providing a counteracting turgor (swelling) force by absorbing a lot of water. Hyaluronic acid polymers are very large (with molecular weights of 100,000-10,000,000) and can displace a large volume of water. This property makes them excellent lubricators and shock absorbers. Hyaluronic acid is thus found in abundance in the ECM of load-bearing joints. It is also a chief component of the interstitial gel. Hyaluronic acid is found on the inner surface of the cell membrane and is translocated out of the cell during biosynthesis.

Hyaluronic acid acts as an environmental cue that regulates cell behavior during embryonic development, healing processes, inflammation and tumor development. It interacts with a specific transmembrane receptor, CD44.

Fibrous components (e.g. structural proteins) of the ECM include collagen and elastin.

Collagens are, in most animals, the most abundant protein in the ECM. In fact, collagen is the most abundant protein in the human body and accounts for 90% of bone matrix protein content. Collagens are present in the ECM as fibrillar proteins and give structural support to resident cells.

Collagen is exocytosed in precursor form (procollagen a longer precursor protein), which is then cleaved by procollagen proteases to allow extracellular assembly. Type I procollagen contains an additional 150 amino acids at the N-terminus and 250 at the C-terminus. These pro-domains are globular and form multiple intrachain disulfide bonds. The disulfides stabilize the proprotein allowing the triple helical section to form.

There are at least 30 different collagen genes dispersed through the human genome. These 30 genes generate proteins that combine in a variety of ways to create over 20 different types of collagen fibrils.

Collagen is the main protein component of connective tissues and basement membrane, and occurs in a number of forms (Type I-XVIII) that vary in their tensile strength and tissue localization. Rigid or flexible structure and structural changes in many body tissues are often a result of changes in collagen composition, as is cellular restriction and compartmentalization. The collagen can be divided into several families according to the types of structure they form: Fibrillar (Type I, II, III, V, XI); Facit (Type IX, XII, XIV); Short chain (Type VIII, X); Basement membrane (Type IV); Other (Type VI, VII, XIII). Types I, II and III are the most abundant and form fibrils of similar structure. Type IV collagen forms a two-dimensional reticulum and is a major component of the basal lamina. Collagens are predominantly synthesized by fibroblasts but epithelial cells also synthesize these proteins.

The table below lists the characteristics of the 12 most characterized types of collagen fibrils. As indicated above there are at least 20 different types of collagen fibrils in the various ECMs of the body.

Types of Collagen

| Type | Chain Composition | Gene Symbol(s) | Structural Details | Localization |
|---|---|---|---|---|
| I | [α1(I)]2[α(I)] | COL1A1, COL1A2 | 300 nm, 67 nm banded fibrils | skin, tendon, bone, etc. |
| II | [α1(II)]3 | COL2A1 | 300 nm, small 67 nm fibrils | cartilage, vitreous humor |
| III | [α1(III)]3 | COL3A1 | 300 nm, small 67 nm fibrils | skin, muscle, frequently with type I |
| IV | [α1(IV)2[α2(IV)] | COL4A1 thru COL4A6 | 390 nm C-term globular domain, nonfibrillar | all basal lamina |
| V | [α1(V)][α2(V)][α3(V)] | COL5A1, COL5A2, COL5A3 | 390 nm N-term globular domain, small fibers | most interstitial tissue, assoc. with type I |
| VI | [α1(VI)][α2(VI)][α3(VI)] | COL6A1, COL6A2, COL6A3 | 150 nm, N + C term. globular domains, microfibrils, 100 nm banded fibrils | most interstitial tissue, assoc. with type I |
| VII | [α1(VII)]3 | COL7A1 | 450 nm, dimer | epithelia |
| VIII | [α1(VIII)]3 | COL8A1, COL8A2 | | some endothelial cells |
| IX | [α1(IX)][α2(IX)][α3(IX)] | COL9A1, COL9A2, COL9A3 | 200 nm, N-term. globular domain, bound proteoglycan | cartilage, assoc. with type II |
| X | [α1(X)]3 | COL10A1 | 150 nm, C-term. globular domain | hypertrophic and mineralizing cartilage |
| XI | [α1(XI)][α2(XI)][α3(XI)] | COL11A1, COL11A2 | 300 nm, small fibers | cartilage |
| XII | α1(XII) | COL12A1 | | interacts with types I and III |

The fundamental higher order structure of collagens is a long and thin diameter rod-like protein. Type I collagen for instance is 300 nm long, 1.5 nm in diameter and consists of 3 coiled subunits composed of two α1(I) chains and one α2(I) chain. Each chain consists of 1050 amino acids wound around each other in a characteristic right-handed triple helix. There are 3 amino acids per turn of the helix and every third amino acid is a G. Collagens are also rich in proline and hydroxyproline. The bulky pyrollidone rings of proline reside on the outside of the triple helix.

Lateral interactions of triple helices of collagens result in the formation of fibrils roughly 50 nm diameter. The packing of collagen is such that adjacent molecules are displaced approximately ¼ of their length (67 nm). This staggered array produces a striated effect that can be seen in the electron microscope.

Collagen fibers begin to assemble in the ER and Golgi complexes. The signal sequence is removed and numerous modifications take place in the collagen chains. Specific proline residues are hydroxylated by prolyl 4-hydroxylase and prolyl 3-hydroxylase. Specific lysine residues also are hydroxylated by lysyl hydroxylase. Both prolyl hydraoxylases are absolutely dependent upon vitamin C as co-factor. Glycosylations of the O-linked type also occurs during Golgi transit. Following completion of processing the pro-collagens are secreted into the extracellular space where extracellular enzymes remove the pro-domains. The collagen molecules then polymerize to form collagen fibrils. Accompanying fibril formation is the oxidation of certain lysine residues by the extracellular enzyme lysyl oxidase forming reactive aldehydes. These reactive aldehydes form specific cross-links between two chains thereby, stabilizing the staggered array of the collagens in the fibril.

Diseases such as osteogenesis imperfecta and epidermolysis bullosa are linked with genetic defects in collagen-encoding genes.

Elastins, in contrast to collagens, give elasticity to tissues, allowing them to stretch when needed and then return to their original state. This is useful in blood vessels, the lungs, in skin, and the ligamentum nuchae, and these tissues contain high amounts of elastins. Elastins are synthesized by fibroblasts and smooth muscle cells. Elastins are highly insoluble, and tropoelastins are secreted inside a chaperone molecule, which releases the precursor molecule upon contact with a fiber of mature elastin. Tropoelastins are then deaminated to become incorporated into the elastin strand. Diseases such as cutis laxa and Williams syndrome are associated with deficient or absent elastin fibers in the ECM.

Other components of ECM include specialized proteins such as fibronectin, laminin, merosin (laminin-2), tenascin, vitronectin, and fibrillin.

Fibronectin is a high molecular weight glycoprotein that binds integrins as well as components of the extracellular matrix (ECM) including collagen, fibrin, and heparin. Fibronectins are proteins that connect cells with collagen fibers in the ECM, allowing cells to move through the ECM. Fibronectins bind collagen and cell surface integrins, causing a reorganization of the cell's cytoskeleton and facilitating cell movement. Fibronectins are secreted by cells in an unfolded, active form. Binding to integrins unfolds fibronectin molecules, allowing them to form dimers so that they can function properly. Fibronectins also help at the site of tissue injury by binding to platelets during blood clotting and facilitating cell movement to the affected area during wound healing.

Fibronectin can be found in the blood plasma in its soluble form, which is composed of two 250 kDa subunits joined together by disulfide bonds. Fibronectin attaches cells to all matrices except type IV that involves laminin as the adhesive molecule. Fibronectins are dimers of 2 similar peptides. Each chain is 60-70 nm long and 2-3 nm thick. The insoluble form that was formerly called cold-insoluble globulin is a large complex of cross-linked subunits.

There are several main isoforms of fibronectin, all of which are the product of a single gene—that is, at least 20 different fibronectin chains have been identified that arise by alternative RNA splicing of the primary transcript from a single fibronectin gene. The structure of these isoforms are made of three types of repeated internal regions called I, II and III that exhibit different lengths and presence or absence of disulfide bonds. Alternative splicing of the pre-mRNA leads to the combination of these three types of regions but also to a variable region. Fibronectin is involved in the wound healing process and so can be used as a therapeutic agent. It is also one of the few proteins for which production increases with age without any associated pathology. In addition, polymeric forms of fibronectin inhibit tumor growth, angiogenesis and metastasis.

Fibronectins contain at least 6 tightly folded domains each with a high affinity for a different substrate such as heparan sulfate, collagen (separate domains for types I, II and III), fibrin and cell-surface receptors. The cell-surface receptor-binding domain contains a consensus amino acid sequence, RGDS.

Laminin is a large, noncollagenous, basement membrane glycoprotein with diverse biological functions including differentiation, migration, and adhesion of normal and tumor cells. Laminin proteins are found in the basal laminae of virtually all animals. Rather than forming collagen-like fibers, laminins form networks of web-like structures that resist tensile forces in the basal lamina. They also assist in cell adhesion. Laminins bind other ECM components such as collagens, nidogens, and entactins.

The protein Laminin is complex, consisting of three different polypeptide chains (a b g) that are bound to each other by disulfide bonds into a cross-shaped molecule comprising one long and three short arms with globules at each end. The a-2 chain is a subunit of laminin-2 (merosin) and laminin-4 (S-merosin). Its cell binding ability (via membranebound integrin receptors) makes laminin an effective substrate coating for stimulating and enhancing cell migration and neurite outgrowth. In laminin from placenta, the A chain is replaced with merosin, and in laminin found near the neuromuscular junction, the B1 chain is replaced by s-laminin (synapse laminin).

A number of laminin subtypes have been identified with varied binding properties. For example, laminin-5 is a basement membrane extracellular matrix macromolecule that provides an attachment substrate for both adhesion and migration in a wide variety of cell types, including epithelial cells, fibroblasts, neurons and leukocytes. Laminin-5 is a preferred adhesion substrate for epithelial cells. Compared to fibronectin, collagen, or vitronectin, cells of epithelial origin will adhere to laminin-5 faster and will spread to a larger extent. Furthermore, laminin-5 protein can be used, in most applications, at coating concentrations in the 1 ig/mL or lower range, which is approximately 10-fold lower than most other extracellular matrix macromolecules.

All basal laminae contain a common set of proteins and GAGs. These are type IV collagen, heparan sulfate proteoglycans, entactin and laminin. The basal lamina is often referred to as the type IV matrix. Each of the components of the basal lamina is synthesized by the cells that rest upon it. Laminin anchors cell surfaces to the basal lamina.

Representative Matrix Types Produced by Vertebrate Cells

| Collagen | Anchor | Proteoglycan | Cell-Surface Receptor | Cells |
|---|---|---|---|---|
| I | fibronectin | chondroitin and dermatan sulfates | integrin | fibroblasts |
| II | fibronectin | chondroitin sulfate | integrin | chondrocytes |
| III | fibronectin | heparan sulfate and heparin | integrin | quiescent hepatocytes, epithelial; assoc. fibroblasts |
| IV | laminin | heparan sulfate and heparin | laminin receptors | all epithelial cells, endothelial cells, regenerating hepatocytes |
| V | fibronectin | heparan sulfate and heparin | integrin | quiescent fibroblasts |
| VI | fibronectin | heparan sulfate | integrin | quiescent fibroblasts |

Merosin is a basement membrane-associated ECM protein, similar in size and structure to other laminins. Merosin is found in placenta, peripheral nerve, and is the predominant laminin variant in skeletal muscle basement membranes. Defects in the protein result in a devastating form of congenital muscular dystrophy (MDC1A). The protein structure consists of three laminin chains (a b g). Merosin forms a link between the peripheral membrane protein a-dystroglycan and the basal lamina. Binding to cells via a high affinity receptor, merosin and other laminins are thought to mediate the attachment, migration and organization of cells into tissues during embryonic development by interacting with other extracellular matrix components.

The tenascin family of cell adhesion matrix glycoproteins is involved in diverse substrate-adhesion interactions in developmental, adult and tumor tissues. The best known isoforms are tenascin —C, —X, —R, —Y and —W, with tenascin-C being fairly well characterized. The basic structure includes a linear portion of 14EGF-like repeats towards the N-terminal end followed by eight or more FnIII domains, depending upon species and splice variant.

Cell migration is a fundamental function of normal cellular processes, including embryonic development, angiogenesis, wound healing, immune response, and inflammation. Cell migration is governed by a variety of factors, including cell surface adhesion receptor binding to extracellular matrix (ECM) proteins. One such matrix protein is vitronectin (VN). VN is a widely distributed high molecular weight glycoprotein found in most extracellular matrices and blood plasma that is known to promote cell adhesion and affect cell morphology, migration, differentiation, and cytoskeletal organization.

Fibrillin is a glycoprotein, which is essential for the formation of elastic fibers found in connective tissue. To date, 3 forms of fibrillin have been described (Fibrillin-1, -2, and -3). Fibrillin-1 is a major component of the microfibrils that form a sheath surrounding the amorphous elastin. It is believed that the microfibrils are composed of end-to-end polymers of fibrillin. (Fibrillin-2 and is thought to play a role in early elastogenesis. Fibrillin-3 is believed to be located mainly in the brain, but may also be present in gonads and ovaries, as it has been localized in the gonads and ovaries of field mice.)

Many cells bind to components of the extracellular matrix. Cell adhesion can occur in two ways; by focal adhesions, connecting the ECM to actin filaments of the cell, and hemidesmosomes, connecting the ECM to intermediate filaments such as keratin. This cell-to-ECM adhesion is regulated by specific cell surface cellular adhesion molecules (CAM) known as integrins. Integrins are cell surface proteins that bind cells to ECM structures, such as fibronectin and laminin, and also to integrin proteins on the surface of other cells.

Fibronectins bind to ECM macromolecules and facilitate their binding to transmembrane integrins. The attachment of fibronectin to the extracellular domain initiates intracellular signaling pathways as well as association with the cellular cytoskeleton via a set of adaptor molecules such as actin.

There are many cell types that contribute to the development of the various types of extracellular matrix found in plethora of tissue types. The local components of ECM determine the properties of the connective tissue.

Fibroblasts are the most common cell type in connective tissue ECM, in which they synthesize, maintain and provide a structural framework; fibroblasts secrete the precursor components of the ECM, including the ground substance. Chondrocytes are found in cartilage and produce the cartilagenous matrix. Osteoblasts are responsible for bone formation.

Extracellular Matrix cells have been found to cause regrowth and healing of tissue. In human fetuses, for example, the extracellular matrix works with stem cells to grow and regrow all parts of the human body, and fetuses can regrow anything that gets damaged in the womb. Scientists have long believed that the matrix stops functioning after full development. It has been used in the past to help horses heal torn ligaments, but it is being researched further as a device for tissue regeneration in humans.

In terms of injury repair and tissue engineering, the extracellular matrix serves two main purposes. First, it prevents the immune system from triggering from the injury and responding with inflammation and scar tissue. Next, it facilitates the surrounding cells to repair the tissue instead of forming scar tissue.

For medical applications, the cells required are usually (although not always) extracted from pig bladders, an easily accessible and relatively unused source. It is currently being used regularly to treat ulcers by closing the hole in the tissue that lines the stomach, but further research is currently being done by many universities as well as the U.S. Government for wounded soldier applications. As of early 2007, testing was being carried out on a military base in Texas. Scientists are using a powdered form on Iraq War veterans whose hands were damaged in the war.

Use of ECM, whether alone or in conjunction with another therapeutic agent (another biologic agent or pharmaceutical agent) may be used to restore endothelial function at the location of delivery. For non-limiting example, although vessels visualized by SEM at 28 days following implantation of a stent—particularly a drug-coated stent, may show complete endothelialization, the function of that endothelial tissue may not be restored. However, a stent comprising ECM, or at least one component thereof, can restore this endothelial function at 28 days, at least. This can be shown by Rapid Atrial Pacing testing as described in Hamilos et al. JACC Vol. 51, No. 22, 2008, Endothelium and DES Jun. 3, 2008:2123-9 incorporated herein in its entirety by reference. Restored endothelial function can be shown in animal studies which determine endothelial function by acetylcholine challenge (ACH) testing by determining the presence of Nitric Oxide (NO). Normal vessels dilate in response to exercise or acetylcholine (ACH). The dilation response is dependent on the endothelial production of NO (Nitric Oxide). In contrast, atherosclerotic vessels are characterized by having endothelial dysfunction and constrict in response to exercise or ACH. This is explained by either a loss of endothelial cells or loss of eNOS expression and NO production. Despite 100% endothelialization as determined by immunohistochemistry or by SEM, a vessel may not have full endothelial function. Endothelial function, thus, may be shown by evidence of eNOS staining by immunohistochemistry, or by presence of eNOS (endothelial Nitric Oxide Synthase) mRNA expression as determined by RT-PCR. eNOS protein level may alternatively be detected by Western blot analysis tested in an animal model to determine restored endothelial function.

"Polymer" as used herein, refers to a series of repeating monomeric units that have been cross-linked or polymerized. Any suitable polymer can be used to carry out the present invention. It is possible that the polymers of the invention may also comprise two, three, four or more different polymers. In some embodiments, of the invention only one polymer is used. In some preferred embodiments a combination of two polymers are used. Combinations of polymers can be in varying ratios, to provide coatings with differing properties. Those of skill in the art of polymer chemistry will be familiar with the different properties of polymeric compounds.

"Copolymer" as used herein refers to a polymer being composed of two or more different monomers. A copolymer may also and/or alternatively refer to random, block, graft, copolymers known to those of skill in the art.

"Biocompatible" as used herein, refers to any material that does not cause injury or death to the animal or induce an adverse reaction in an animal when placed in intimate contact with the animal's tissues. Adverse reactions include for example inflammation, infection, fibrotic tissue formation, cell death, or thrombosis. The terms "biocompatible" and "biocompatibility" when used herein are art-recognized and mean that the referent is neither itself toxic to a host (e.g., an animal or human), nor degrades (if it degrades) at a rate that produces byproducts (e.g., monomeric or oligomeric subunits or other byproducts) at toxic concentrations, causes inflammation or irritation, or induces an immune reaction in the host. It is not necessary that any subject composition have a purity of 100% to be deemed biocompatible. Hence, a subject composition may comprise 99%, 98%, 97%, 96%, 95%, 90% 85%, 80%, 75% or even less of biocompatible agents, e.g., including polymers and other materials and excipients described herein, and still be biocompatible.

To determine whether a polymer or other material is biocompatible, it may be necessary to conduct a toxicity analysis. Such assays are well known in the art. One example of such an assay may be performed with live carcinoma cells, such as GT3TKB tumor cells, in the following manner: the sample is degraded in 1 M NaOH at 37° C. until complete degradation is observed. The solution is then neutralized with 1M HCl. About 200 microliters of various concentrations of the degraded sample products are placed in 96-well tissue culture plates and seeded with human gastric carcinoma cells (GT3TKB) at 104/well density. The degraded sample products are incubated with the GT3TKB cells for 48 hours. The results of the assay may be plotted as % relative growth vs. concentration of degraded sample in the tissue-culture well. In addition, polymers and formulations of the present invention may also be evaluated by well-known in vivo tests, such as subcutaneous implantations in rats to confirm that they do not cause significant levels of irritation or inflammation at the subcutaneous implantation sites.

The terms "bioabsorbable," "biodegradable," "bioerodible," and "bioresorbable," are art-recognized synonyms. These terms are used herein interchangeably. Bioabsorbable polymers typically differ from non-bioabsorbable polymers in that the former may be absorbed (e.g.; degraded) during use. In certain embodiments, such use involves in vivo use, such as in vivo therapy, and in other certain embodiments, such use involves in vitro use. In general, degradation attributable to biodegradability involves the degradation of a bioabsorbable polymer into its component subunits, or digestion, e.g., by a biochemical process, of the polymer into smaller, non-polymeric subunits. In certain embodiments, biodegradation may occur by enzymatic mediation, degradation in the presence of water (hydrolysis) and/or other chemical species in the body, or both. The bioabsorbabilty of a polymer may be shown in-vitro as described herein or by methods known to one of skill in the art. An in-vitro test for bioabsorbability of a polymer does not require living cells or other biologic materials to show bioabsorption properties (e.g. degradation, digestion). Thus, resorbtion, resorption, absorption, absorbtion, erosion, and dissolution may also be used synonymously with the terms "bioabsorbable," "biodegradable," "bioerodible," and "bioresorbable." Mechanisms of degradation of a bioabsorbable polymer may include, but are not limited to, bulk degradation, surface erosion, and combinations thereof.

In some embodiments, the device comprises a bioabsorbable polymer. A bioabsorbable polymer may comprise, for non-limiting example, at least one of: PLGA, PGA poly (glycolide), LPLA poly(l-lactide), DLPLA poly(dl-lactide), PCL poly(e-caprolactone) PDO, poly(dioxalone) PGA-TMC, 85/15 DLPLG p(dl-lactide-co-glycolide), 75/25 DLPL, 65/35 DLPLG, 50/50 DLPLG, TMC poly(trimethylcarbonate), and p(CPP:SA) poly(1,3-bis-p-(carboxyphenoxy)propane-co-sebacic acid).

As used herein, the term "biodegradation" encompasses both general types of biodegradation. The degradation rate of a biodegradable polymer often depends in part on a variety of factors, including the chemical identity of the linkage responsible for any degradation, the molecular weight, crystallinity, biostability, and degree of cross-linking of such polymer, the physical characteristics (e.g., shape and size) of the implant, and the mode and location of administration. For example, the greater the molecular weight, the higher the degree of crystallinity, and/or the greater the biostability, the biodegradation of any bioabsorbable polymer is usually slower.

Provided herein is a bioabsorbable device comprising a bioabsorbable substrate comprising a first active agent; and a coating on said substrate wherein the coating comprises a first polymer, wherein the first active agent comprises at least one of: extracellular matrix and an extracellular matrix component.

Provided herein is a bioabsorbable device comprising a bioabsorbable substrate; and a coating on said substrate wherein the coating comprises a first polymer and a first active agent, wherein the first active agent comprises at least one of: extracellular matrix and an extracellular matrix component.

In some embodiments, the extracellular matrix component comprises at least one of: heparin sulfate, chondroitin sulfate, keratan sulfate, hyaluronic acid, collagen, elastin, fibronectin, laminin, merosin, tenascin, vitronectin, and fibrillin.

In some embodiments, the bioabsorbable device is a bioabsorbable stent. In some embodiments, the bioabsorbable substrate comprises a bioabsorbable metal framework. In some embodiments, the bioabsorbable metal framework comprises magnesium. In some embodiments, the first polymer degrades by bulk erosion. In some embodiments, the bioabsorbable substrate comprises a second polymer. In some embodiments, the first polymer and the second polymer are the same polymer. In some embodiments, the second polymer degrades by surface erosion. In some embodiments the first polymer degrades by surface erosion.

In some embodiments, the coating comprises a second active agent. In some embodiments, the bioabsorbable substrate comprises a second active agent. In some embodiments, the second active agent comprises at least one of a pharmaceutical agent and a biologic agent. In some embodiments, the pharmaceutical agent comprises a macrolide immunosuppressive (limus) drug. In some embodiments, the macrolide immunosuppressive (limus) drug comprises one or more of: rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin, 40-O-(2-Hydroxy)ethoxycar-bonylmethyl-rapamycin, 40-O-(3-Hydroxy)propyl-rapamycin, 40-O-(6-Hydroxy)hexyl-rapamycin, 40-O-[2-(2-Hydroxy)ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin, 40-O-(2-Nicotinoyloxy)ethyl-rapamycin, 40-O-[2-(N-Morpholino)acetoxy]ethyl-rapamycin, 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin, 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof.

In some embodiments, the device is delivered to a target tissue and returns endothelial function to the target tissue at 28 days from device delivery. In some embodiments, the endothelial function is determined using Rapid Atrial Pacing. In some embodiments, the endothelial function is determined using acetylcholine challenge testing in an animal model. In some embodiments, the endothelial function is determined by detection of eNOS protein in an animal model.

Provided herein is a method of preparing a bioabsorbable device; said method comprising: providing a bioabsorbable substrate comprising a first active agent; and forming a coating on said substrate wherein the coating comprises a first polymer, wherein at least a portion of the active agent comprises at least one of extracellular matrix and an extracellular matrix component.

Provided herein is a method of preparing a bioabsorbable device; said method comprising providing a bioabsorbable substrate; and forming a coating on said substrate wherein the coating comprises a first polymer and a first active agent, wherein the first active agent comprises at least one of: extracellular matrix and an extracellular matrix component.

In some embodiments, the extracellular matrix component comprises at least one of: heparin sulfate, chondroitin sulfate, keratan sulfate, hyaluronic acid, collagen, elastin, fibronectin, laminin, merosin, tenascin, vitronectin, and fibrillin.

In some embodiments, the bioabsorbable device is a bioabsorbable stent. In some embodiments, the bioabsorbable substrate comprises a bioabsorbable metal framework. In some embodiments, the bioabsorbable metal framework comprises magnesium. In some embodiments, the first polymer degrades by bulk erosion. In some embodiments, the bioabsorbable substrate comprises a second polymer. In some embodiments, the first polymer and the second polymer are the same polymer. In some embodiments, the second polymer degrades by surface erosion. In some embodiments the first polymer degrades by surface erosion.

In some embodiments, the coating comprises a second active agent. In some embodiments, the bioabsorbable substrate comprises a second active agent. In some embodiments, the second active agent comprises at least one of a pharmaceutical agent and a biologic agent. In some embodiments, the pharmaceutical agent comprises a macrolide immunosuppressive (limus) drug. In some embodiments, the macrolide immunosuppressive (limus) drug comprises one or more of: rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin, 40-O-(2-Hydroxy)ethoxycar-bonylmethyl-rapamycin, 40-O-(3-Hydroxy)propyl-rapamycin, 40-O-(6-Hydroxy)hexyl-rapamycin, 40-O-[2-(2-Hydroxy)ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin, 40-O-(2-Nicotinoyloxy)ethyl-rapamycin, 40-O-[2-(N-Morpholino)acetoxy]ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin, 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), picrolimus, novolimus, myolimus, and salts, derivatives, isomers, racemates, diastereoisomers, prodrugs, hydrate, ester, or analogs thereof.

In some embodiments, the device is delivered to a target tissue and returns endothelial function to the target tissue at 28 days from device delivery. In some embodiments, the endothelial function is determined using Rapid Atrial Pacing. In some embodiments, the endothelial function is determined using acetylcholine challenge testing in an animal model. In some embodiments, the endothelial function is determined by detection of eNOS protein in an animal model.

As used herein, the term "durable polymer" refers to a polymer that is not bioabsorbable (and/or is not bioerodable, and/or is not biodegradable, and/or is not bioresorbable) and is, thus biostable. In some embodiments, the device comprises a durable polymer. The polymer may include a cross-linked durable polymer. Example biocompatible durable polymers include, but are not limited to: polyester, aliphatic polyester, polyanhydride, polyethylene, polyorthoester, polyphosphazene, polyurethane, polycarbonate urethane, aliphatic polycarbonate, silicone, a silicone containing polymer, polyolefin, polyamide, polycaprolactam, polyamide, polyvinyl alcohol, acrylic polymer, acrylate, polystyrene, epoxy, polyethers, celluiosics, expanded polytetrafluoroethylene, phosphorylcholine, polyethyleneyerphthalate, polymethylmethavrylate, poly(ethylmethacrylate/n-butylmethacrylate), parylene C, polyethylene-co-vinyl acetate, polyalkyl methacrylates, polyalkylene-co-vinyl acetate, polyalkylene, polyalkyl siloxanes, polyhydroxyalkanoate, polyfluoroalkoxyphasphazine, poly(styrene-b-isobutylene-b-styrene), poly-butyl methacrylate, poly-bytadiene, and blends, combinations, homopolymers, condensation polymers, alternating, block, dendritic, cross-linked, and copolymers thereof. The polymer may include a thermoset material. The polymer may provide strength for the coated implanable medical device. The polymer may provide durability for the coated implanable medical device. The coatings and coating methods provided herein provide substantial protection from these by establishing a multi-layer coating which can be bioabsorbable or durable or a combination thereof, and which can both deliver active agents and provide elasticity and radial strength for the vessel in which it is delivered.

In some embodiments, the polymer comprises is at least one of: a fluoropolymer, PVDF-HFP comprising vinylidene fluoride and hexafluoropropylene monomers, PC (phosphorylcholine), Polysulfone, polystyrene-b-isobutylene-b-styrene, PVP (polyvinylpyrrolidone), alkyl methacrylate, vinyl acetate, hydroxyalkyl methacrylate, and alkyl acrylate. In some embodiments, the alkyl methacrylate comprises at least one of methyl methacrylate, ethyl methacrylate, propyl methacrylate, butyl methacrylate, hexyl methacrylate, octyl methacrylate, dodecyl methacrylate, and lauryl methacrylate. In some embodiments, the alkyl acrylate comprises at least one of methyl acrylate, ethyl acrylate, propyl acrylate, butyl acrylate, hexyl acrylate, octyl acrylate, dodecyl acrylates, and lauryl acrylate.

"Therapeutically desirable morphology" as used herein refers to the gross form and structure of the pharmaceutical agent, once deposited on the substrate, so as to provide for optimal conditions of ex vivo storage, in vivo preservation and/or in vivo release. Such optimal conditions may include, but are not limited to increased shelf life, increased in vivo stability, good biocompatibility, good bioavailability or modified release rates. Typically, for the present invention, the desired morphology of a pharmaceutical agent would be crystalline or semi-crystalline or amorphous, although this may vary widely depending on many factors including, but not limited to, the nature of the pharmaceutical agent, the disease to be treated/prevented, the intended storage conditions for the substrate prior to use or the location within the body of any biomedical implant. Preferably at least 10%, 20%, 30%, 40%, 50%, 60%, 70%, 80%, 90% or 100% of the pharmaceutical agent is in crystalline or semi-crystalline form.

"Stabilizing agent" as used herein refers to any substance that maintains or enhances the stability of the biological agent. Ideally these stabilizing agents are classified as Generally Regarded As Safe (GRAS) materials by the US Food and Drug Administration (FDA). Examples of stabilizing agents include, but are not limited to carrier proteins, such as albumin, gelatin, metals or inorganic salts. Pharmaceutically acceptable excipient that may be present can further be found in the relevant literature, for example in the Handbook of Pharmaceutical Additives: An International Guide to More Than 6000 Products by Trade Name, Chemical, Function, and Manufacturer; Michael and Irene Ash (Eds.); Gower Publishing Ltd.; Aldershot, Hampshire, England, 1995.

"Compressed fluid" as used herein refers to a fluid of appreciable density (e.g., >0.2 g/cc) that is a gas at standard temperature and pressure. "Supercritical fluid", "near-critical fluid", "near-supercritical fluid", "critical fluid", "densified fluid" or "densified gas" as used herein refers to a compressed fluid under conditions wherein the temperature is at least 80% of the critical temperature of the fluid and the pressure is at least 50% of the critical pressure of the fluid, and/or a density of +50% of the critical density of the fluid.

Examples of substances that demonstrate supercritical or near critical behavior suitable for the present invention include, but are not limited to carbon dioxide, isobutylene, ammonia, water, methanol, ethanol, ethane, propane, butane, pentane, dimethyl ether, xenon, sulfur hexafluoride, halogenated and partially halogenated materials such as chlorofluorocarbons, hydrochlorofluorocarbons, hydrofluorocarbons, perfluorocarbons (such as perfluoromethane and perfluoropropane, chloroform, trichloro-fluoromethane, dichloro-difluoromethane, dichloro-tetrafluoroethane) and mixtures thereof. Preferably, the supercritical fluid is hexafluoropropane (FC-236EA), or 1,1,1,2,3,3-hexafluoropropane. Preferably, the supercritical fluid is hexafluoropropane (FC-236EA), or 1,1,1,2,3,3-hexafluoropropane for use in PLGA polymer coatings.

"Sintering" as used herein refers to the process by which parts of the polymer or the entire polymer becomes continuous (e.g., formation of a continuous polymer film). As discussed below, the sintering process is controlled to produce a fully conformal continuous polymer (complete sintering) or to produce regions or domains of continuous coating while producing voids (discontinuities) in the polymer. As well, the sintering process is controlled such that some phase separation is obtained or maintained between polymer different polymers (e.g., polymers A and B) and/or to produce phase separation between discrete polymer particles. Through the sintering process, the adhesions properties of the coating are improved to reduce flaking of detachment of the coating from the substrate during manipulation in use. As described below, in some embodiments, the sintering process is controlled to provide incomplete sintering of the polymer. In embodiments involving incomplete sintering, a polymer is formed with continuous domains, and voids, gaps, cavities, pores, channels or, interstices that provide space for sequestering a therapeutic agent which is released under controlled conditions. Depending on the nature of the polymer, the size of polymer particles and/or other polymer properties, a compressed gas, a densified gas, a near critical fluid or a super-critical fluid may be employed. In one example, carbon dioxide is used to treat a substrate that has been coated with a polymer and a active agent, using dry powder and RESS electrostatic coating processes. In another example, isobutylene is employed in the sintering process. In other examples a mixture of carbon dioxide and isobutylene is employed. In another example, 1,1,2,3,3-hexafluoropropane is employed in the sintering process.

When an amorphous material is heated to a temperature above its glass transition temperature, or when a crystalline material is heated to a temperature above a phase transition temperature, the molecules comprising the material are more mobile, which in turn means that they are more active and thus more prone to reactions such as oxidation. However, when an amorphous material is maintained at a temperature below its glass transition temperature, its molecules are substantially immobilized and thus less prone to reactions. Likewise, when a crystalline material is maintained at a temperature below its phase transition temperature, its molecules are substantially immobilized and thus less prone to reactions. Accordingly, processing active agent components at mild conditions, such as the deposition and sintering conditions described herein, minimizes cross-reactions and degradation of the active agent component. One type of reaction that is minimized by the processes of the invention relates to the ability to avoid conventional solvents which in turn minimizes-oxidation of active agent, whether in amorphous, semi-crystalline, or crystalline form, by reducing exposure thereof to free radicals, residual solvents, protic materials, polar-protic materials, oxidation initiators, and autoxidation initiators.

"Rapid Expansion of Supercritical Solutions" or "RESS" as used herein involves the dissolution of a polymer into a compressed fluid, typically a supercritical fluid, followed by rapid expansion into a chamber at lower pressure, typically near atmospheric conditions. The rapid expansion of the supercritical fluid solution through a small opening, with its accompanying decrease in density, reduces the dissolution capacity of the fluid and results in the nucleation and growth of polymer particles. The atmosphere of the chamber is maintained in an electrically neutral state by maintaining an isolating "cloud" of gas in the chamber. Carbon dioxide, nitrogen, argon, helium, or other appropriate gas is employed to prevent electrical charge is transferred from the substrate to the surrounding environment.

"Bulk properties" properties of a coating including a pharmaceutical or a biological agent that can be enhanced through the methods of the invention include for example: adhesion, smoothness, conformality, thickness, and compositional mixing.

"Electrostatically charged" or "electrical potential" or "electrostatic capture" or "e-" as used herein refers to the collection of the spray-produced particles upon a substrate that has a different electrostatic potential than the sprayed particles. Thus, the substrate is at an attractive electronic potential with respect to the particles exiting, which results in the capture of the particles upon the substrate. i.e. the substrate and particles are oppositely charged, and the particles transport through the gaseous medium of the capture vessel onto the surface of the substrate is enhanced via electrostatic attraction. This may be achieved by charging the particles and grounding the substrate or conversely charging the substrate and grounding the particles, by charging the particles at one potential (e.g. negative charge) and charging the substrate at an opposite potential (e.g. positive charge), or by some other process, which would be easily envisaged by one of skill in the art of electrostatic capture. E-RESS (or e-RESS), thus, may refer to Electrostatically charged Rapid Expansion of Supercritical Solutions.

"Intimate mixture" as used herein, refers to two or more materials, compounds, or substances that are uniformly distributed or dispersed together.

"Layer" as used herein refers to a material covering a surface or forming an overlying part or segment. Two different layers may have overlapping portions whereby material from one layer may be in contact with material from another layer. Contact between materials of different layers can be measured by determining a distance between the materials. For example, Raman spectroscopy may be employed in identifying materials from two layers present in close proximity to each other.

While layers defined by uniform thickness and/or regular shape are contemplated herein, several embodiments described below relate to layers having varying thickness and/or irregular shape. Material of one layer may extend into the space largely occupied by material of another layer. For example, in a coating having three layers formed in sequence as a first polymer layer, a pharmaceutical agent layer and a second polymer layer, material from the second polymer layer which is deposited last in this sequence may extend into the space largely occupied by material of the pharmaceutical agent layer whereby material from the second polymer layer may have contact with material from the pharmaceutical layer. It is also contemplated that material from the second polymer layer may extend through the entire layer largely occupied by pharmaceutical agent and contact material from the first polymer layer.

It should be noted however that contact between material from the second polymer layer (or the first polymer layer) and material from the pharmaceutical agent layer (e.g.; a pharmaceutical agent crystal particle or a portion thereof) does not necessarily imply formation of a mixture between the material from the first or second polymer layers and material from the pharmaceutical agent layer. In some embodiments, a layer may be defined by the physical three-dimensional space occupied by crystalline particles of a pharmaceutical agent (and/or biological agent). It is contemplated that such layer may or may not be continuous as physical space occupied by the crystal particles of pharmaceutical agents may be interrupted, for example, by polymer material from an adjacent polymer layer. An adjacent polymer layer may be a layer that is in physical proximity to be pharmaceutical agent particles in the pharmaceutical agent layer. Similarly, an adjacent layer may be the layer formed in a process step right before or right after the process step in which pharmaceutical agent particles are deposited to form the pharmaceutical agent layer.

As described below, material deposition and layer formation provided herein are advantageous in that the pharmaceutical agent remains largely in crystalline form during the entire process. While the polymer particles and the pharmaceutical agent particles may be in contact, the layer formation process is controlled to avoid formation of a mixture between the pharmaceutical agent particles the polymer particles during formation of a coated device.

"Laminate coating" as used herein refers to a coating made up of two or more layers of material. Means for creating a laminate coating as described herein (e.g.; a laminate coating comprising polymer(s) and active agent comprising ECM) may include coating the substrate with active agent and polymer as described herein (e-RESS, e-DPC, compressed-gas sintering). The process comprises performing multiple and sequential coating steps (with sintering steps for polymer materials) wherein different materials may be deposited in each step, thus creating a laminated structure with a multitude of layers (at least 2 layers) including polymer layers and active agent layers to build the final device (e.g.; laminate coated stent).

The coating methods provided herein may be calibrated to provide a coating bias whereby the mount of polymer and active agent deposited in the albuminal surface of the substrate (e.g. exterior surface of a stent) is greater than the amount of active agent and amount of polymer deposited on the luminal surface of the substrate (e.g. interior surface of a stent). The resulting configuration may be desirable to provide preferential elution of the agent toward the vessel wall (luminal surface of the stent) where the therapeutic effect of anti-restenosis is desired, without providing the same active agent(s) on the albuminal surface, where they may retard healing, which in turn is suspected to be a cause of late-stage safety problems with current DESs.

As well, the methods described herein provide a device wherein the coating on the stent is biased in favor of increased coating at the ends of the device (whether a stent or another substrate). For example, a stent having three portions along the length of the stent (e.g.; a central portion flanked by two end portions) may have end portions coated with increased amounts of pharmaceutical agent and/or polymer compared to the central portion.

The present invention allows for employing a platform combining layer formation methods based on compressed fluid technologies; electrostatic capture and sintering methods. The platform results in coated substrates having enhanced therapeutic and mechanical properties. The invention is particularly advantageous in that it employs a laminate polymer technology. In particular, the invention in some embodiments allows the formation of discrete layers of specific active agent platforms. As indicated above, the shape of a discrete layer of crystal particles may be irregular, including interruptions of said layer by material from another layer (polymer layer) positioned in space between particles of an active agent.

Conventional processes for spray coating stents require that drug and polymer be dissolved in solvent or mutual solvent before spray coating can occur. The platform provided herein the drugs and polymers are coated on the stent framework in discrete steps, which can be carried out simultaneously or alternately. This allows discrete deposition of the active agent (e.g., a drug) within a polymer thereby allowing the placement of more than one drug on a single medical device with or without an intervening polymer layer. For example, the present platform provides a dual drug eluting stent.

The present invention in some embodiments includes employing compressed fluids (e.g., supercritical fluids, for example e-RESS based methods); solvent free deposition methodology; a platform that allows processing at lower temperatures thereby preserving the qualities of the active agent and the polymer; the ability to incorporate two, three or more active agents while minimizing deleterious effects from direct interactions between the various active agents and/or their excipients during the fabrication and/or storage of the active agent stents; a dry deposition; enhanced adhesion and mechanical properties of the layers on the stent framework; precision deposition and rapid batch processing; and ability to form intricate structures.

Means for creating the bioabsorbable polymer(s)+active agent (s) coating of the device with or without a substrate:
Spray coat the coating-form with active agent and polymer as is done in Micell process (e-RESS, e-DPC, compressed-gas sintering).
Perform multiple and sequential coating-sintering steps where different materials may be deposited in each step, thus creating a laminated structure with a multitude of thin layers of active agent(s), polymer(s) or active agent+polymer that build the final device.
Perform the deposition of polymer(s)+active agent (s) laminates with the inclusion of a mask on the inner (luminal) surface of the device. Such a mask could be as simple as a non-conductive mandrel inserted through the internal diameter of the coating form. This masking could take place prior to any layers being added, or be purposefully inserted after several layers are deposited continuously around the entire coating-form.

Other methods for preparing the coating include solvent based coating methods and plasma based coating methods.

Provided herein is a device comprising a stent; and a coating on said stent comprising a polymer and an active agent, wherein the active agent comprises at least one of: extracellular matrix and an extracellular matrix component.

Provided herein is a device comprising a substrate; and a coating on said substrate comprising a polymer and an active agent, wherein the active agent comprises at least one of: extracellular matrix and an extracellular matrix component.

In some embodiments, the coating comprises a plurality of layers. In some embodiments at least one of said layers comprises the polymer. In some embodiments, at least one of said layers comprises the active agent. In some embodiments, the polymer and the active agent are in different layers. In some embodiments, the coating is a laminate coating.

In some embodiments, the extracellular matrix component comprises at least one of: heparin sulfate, chondroitin sulfate, keratan sulfate, hyaluronic acid, collagen, elastin, fibronectin, laminin, merosin, tenascin, vitronectin, and fibrillin.

In some embodiments, the polymer is at least one of: a bioabsorbable polymer and a durable polymer. In some embodiments, bioabsorbable polymer comprises a PLGA copolymer. In some embodiments, bioabsorbable polymer is selected from the group PLGA, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid). In some embodiments, the durable polymer comprises at least one of a polyester, aliphatic polyester, polyanhydride, polyethylene, polyorthoester, polyphosphazene, polyurethane, polycarbonate urethane, aliphatic polycarbonate, silicone, a silicone containing polymer, polyolefin, polyamide, polycaprolactam, polyamide, polyvinyl alcohol, acrylic polymer, acrylate, polystyrene, epoxy, polyethers, celluiosics, expanded polytetrafluoroethylene, phosphorylcholine, polyethyleneyerphthalate, polymethylmethavrylate, poly (ethylmethacrylate/n-butylmethacrylate), parylene C, polyethylene-co-vinyl acetate, polyalkyl methacrylates, polyalkylene-co-vinyl acetate, polyalkylene, polyalkyl siloxanes, polyhydroxyalkanoate, polyfluoroalkoxyphasphazine, poly(styrene-b-isobutylene-b-styrene), poly-butyl methacrylate, poly-byta-diene, and blends, combinations, homopolymers, condensation polymers, alternating, block, dendritic, crosslinked, and copolymers thereof.

In some embodiments, the device has at least one active agent layer defined by a three-dimensional physical space occupied by the active agent and said three dimensional physical space is free of polymer. In some embodiments, at least some of the active agent in said three dimensional physical space defining said at least one active agent layer is in contact with polymer particles present in a polymer layer adjacent to said at least one active agent layer defined by said three-dimensional space free of polymer. In some embodiments, the stent has a stent longitudinal length and the coating has a coating outer surface along said stent longitudinal length, wherein said coating comprises active agent present in the coating below said coating outer surface. In some embodiments, the stent has a stent longitudinal length and the coating has a coating outer surface along said stent longitudinal length, wherein said coating comprises active agent present in the coating up to at least 1 µm below said coating outer surface. In some embodiments, the stent has a stent longitudinal length and the coating has a coating outer surface along said stent longitudinal length, wherein said coating comprises active agent present in the coating up to at least 5 µm below said coating outer surface. In some embodiments, said stent has a stent longitudinal axis and a stent length along said stent longitudinal axis, wherein said coating is conformal to the stent along substantially said stent length. In some embodiments, said stent has a stent longitudinal axis and a stent length along said stent longitudinal axis, wherein said coating is conformal to the stent along at least one of: at least 75% of said stent length, at least 85% of said stent length, at least 90% of said stent length, at least 95% of said stent length, and at least 99% of said stent length. In some embodiments, said stent has a stent longitudinal axis and a plurality of struts along said stent longitudinal axis, wherein said coating is conformal to at least one of: at least 50% of said struts, at least 75% of said struts, at least 90% of said struts, and at least 99% of said struts. In some embodiments, coating conformality is shown by an electron microscopy examination of the device.

In some embodiments, said stent has a stent longitudinal axis and a stent length along said stent longitudinal axis, wherein said coating has a substantially uniform thickness along substantially said stent length. In some embodiments, said stent has a stent longitudinal axis and a stent length along said stent longitudinal axis, wherein said coating has a substantially uniform thickness along at least one of: at least 75% of said stent length, and at least 95% of said stent length. In some embodiments, said stent has a stent longitudinal axis and a stent length along said stent longitudinal axis, wherein said coating has an average thickness determined by an average calculated from coating thickness values measured at a plurality of points along said stent longitudinal axis; wherein a thickness of the coating measured at any point along stent longitudinal axis is at least one of: from about 75% to about 125% of said average thickness, and from about 95% to about 105% of said average thickness.

The polymer layer portion may be a sub layer which, at least in part, extends along the albuminal surface of the stent along the longitudinal axis of the stent (where the longitudinal axis of the stent is the central axis of the stent along its tubular length). For example, when a coating is removed from the albuminal surface of the stent, such as when the stent is cut along its length, flattened, and the coating is removed by scraping the coating off using a scalpel, knife or other sharp tool, the coating that is removed (despite having a pattern consistent with the stent pattern) has a layer that can be shown to have the characteristics described herein. This may be shown by sampling multiple locations of the coating that is representative of the entire coating.

Alternatively, and/or additionally, since stents or other complex substrates may include struts and voids and/or other features, the methods provided herein advantageously allow for coatings extending around each feature, the layers of coating are likewise disposed around each feature. Thus, a polymer layer portion may be a layer which, at least, extends around each feature a distance from said feature (although the distance may vary where the coating thickness on the albuminal surface is different than the coating thickness on the luminal and/or sidewalls).

In some embodiments wherein the device comprises a stent, the stent comprises at least five struts, each strut having a strut length along said stent longitudinal axis, wherein said second layer portion extends substantially along substantially the strut length of at least two struts. In some embodiments, the stent comprises at least five struts, each strut having a strut length along said stent longitudinal axis, wherein said second layer portion extends substantially along substantially the strut length of at least three struts. In some embodiments, the stent comprises at least five struts, each strut having a strut length along said stent longitudinal axis, wherein said second layer portion extends substantially along substantially the strut length of least four struts. In some embodiments, the stent comprises at least five struts, each strut having a strut length along said stent longitudinal axis, wherein said second layer portion extends substantially along substantially the strut length of all said at least five struts. In some embodiments, the stent has a stent length along said stent longitudinal axis and said second layer portion extends substantially along said stent length.

In some embodiments, the polymer comprises an intimate mixture of two or more polymers.

In some embodiments, said coating has a thickness of at least one of: from about 5 µm to about 50 µm, from about 10 µm to about 20 µm, and from about 50 µm to about 80 µm.

In some embodiments, the device has at least one active agent layer defined by a three-dimensional physical space occupied by the active agent and said three dimensional physical space is free of polymer. In some embodiments, at least some of the active agent in said three dimensional physical space defining said at least one active agent layer is in contact with polymer particles present in a polymer layer adjacent to said at least one active agent layer defined by said three-dimensional space free of polymer. In some embodiments, the substrate has a substrate longitudinal length and the coating has a coating outer surface along said stent longitudinal length, wherein said coating comprises active agent present in the coating below said coating outer surface. In some embodiments, the substrate has a substrate longitudinal length and the coating has a coating outer surface along said stent longitudinal length, wherein said coating comprises active agent present in the coating up to at least 1 µm below said coating outer surface. In some embodiments, the substrate has a substrate longitudinal length and the coating has a coating outer surface along said stent longitudinal length, wherein said coating comprises active agent present in the coating up to at least 5 µm below said coating outer surface. In some embodiments, the substrate has a substrate longitudinal axis and a substrate length along said substrate longitudinal axis, wherein said coating is conformal to the substrate along substantially said substrate length. In some embodiments, the substrate has a substrate longitudinal axis and a substrate length along said substrate longitudinal axis, wherein said coating is conformal to the substrate along at least one of: at least 75% of said substrate length, at least 85% of said substrate length, at least 90% of said substrate length, at least 95% of said substrate length, and at least 99% of said substrate length. In some embodiments, the coating conformality is shown by an electron microscopy examination of the device. In some embodiments, the substrate has a substrate longitudinal axis and a substrate length along said substrate longitudinal axis, wherein said coating has a substantially uniform thickness along substantially said substrate length. In some embodiments, the substrate has a substrate longitudinal axis and a substrate length along said substrate longitudinal axis, wherein said coating has a substantially uniform thickness along at least one of: at least 75% of said substrate length, and at least 95% of said substrate length. In some embodiments, the substrate has a substrate longitudinal axis and a substrate length along said stent longitudinal axis, wherein said coating has an average thickness determined by an average calculated from coating thickness values measured at a plurality of points along said substrate longitudinal axis; wherein a thickness of the coating measured at any point along stent longitudinal axis is at least one of: from about 75% to about 125% of said average thickness, and from about 95% to about 105% of said average thickness. In some embodiments, the polymer comprises an intimate mixture of two or more polymers. In some embodiments, the coating has a thickness of at least one of: from about 5 µm to about 50 µm, from about 10 µm to about 20 µm, and from about 50 µm to about 80 µm.

Provided herein is a device comprising: a stent; a plurality of layers that form a laminate coating on said stent, wherein a first layer comprises a first polymer, a second layer comprises an active agent, a third layer comprises a second polymer, a fourth layer comprises the active agent, and a fifth layer comprises a third polymer, wherein the active agent comprises at least one of: extracellular matrix and an extracellular matrix component.

Provided herein is a device comprising: a substrate; a plurality of layers that form a laminate coating on said substrate, wherein a first layer comprises a first polymer, a second layer comprises an active agent, a third layer comprises a second polymer, a fourth layer comprises the active agent, and a fifth layer comprises a third polymer, wherein the active agent comprises at least one of: extracellular matrix and an extracellular matrix component.

In some embodiments, the laminate coating has a total thickness and said second polymer layer portion has a thickness of from about 0.01% to about 10% of the total thickness of said laminate coating. In some embodiments, the laminate coating has a total thickness and said horizontal second polymer layer portion has a thickness of from about 1% to about 5% of the total thickness of said laminate coating. In some embodiments, the laminate coating has a total thickness of from about 5 µm to about 50 µm and said horizontal second polymer layer portion has a thickness of from about 0.001 µm to about 5 µm. In some embodiments, the laminate coating has a total thickness of from about 10 µm to about 20 µm and said second polymer layer portion has a thickness of from about 0.01 µm to about 5 µm.

In some embodiments, the laminate coating is at least 25% by volume active agent. In some embodiments, the laminate coating is at least 35% by volume active agent. In some embodiments, the laminate coating is about 50% by volume active agent.

In some embodiments, the extracellular matrix component comprises at least one of: heparin sulfate, chondroitin sulfate, keratan sulfate, hyaluronic acid, collagen, elastin, fibronectin, laminin, merosin, tenascin, vitronectin, and fibrillin.

In some embodiments, at least two of said first polymer, said second polymer and said third polymer are the same polymer. In some embodiments, said first polymer, said second polymer and said third polymer are the same polymer.

In some embodiments, at least one of said first polymer, said second polymer and said third polymer is a bioabsorbable polymer. In some embodiments, the bioabsorbable polymer comprises a PLGA copolymer. In some embodiments, the bioabsorbable polymer is selected from the group PLGA, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid).

In some embodiments, at least one of said first polymer, said second polymer and said third polymer is a durable polymer. In some embodiments, the durable polymer comprises at least one of a polyester, aliphatic polyester, polyanhydride, polyethylene, polyorthoester, polyphosphazene, polyurethane, polycarbonate urethane, aliphatic polycarbonate, silicone, a silicone containing polymer, polyolefin, polyamide, polycaprolactam, polyamide, polyvinyl alcohol, acrylic polymer, acrylate, polystyrene, epoxy, polyethers, celluiosics, expanded polytetrafluoroethylene, phosphorylcholine, polyethyleneyerphthalate, polymethylmethavrylate, poly(ethylmethacrylate/n-butylmethacrylate), parylene C, polyethylene-co-vinyl acetate, polyalkyl methacrylates, polyalkylene-co-vinyl acetate, polyalkylene, polyalkyl siloxanes, polyhydroxyalkanoate, polyfluoroalkoxyphasphazine, poly(styrene-b-isobutylene-b-styrene), poly-butyl methacrylate, poly-byta-diene, and blends, combinations, homopolymers, condensation polymers, alternating, block, dendritic, crosslinked, and copolymers thereof.

In some embodiments, at least two of said first polymer, said second polymer and said third polymer are different polymers.

Provided herein is a method of preparing a device comprising a stent and a plurality of layers that form a laminate coating on said stent; said method comprising: providing a stent; and forming a plurality of layers on said stent; wherein at least one of said layers comprises a polymer and at least one of said layers comprises one or more active agents; wherein at least a portion of the active agent comprises at least one of extracellular matrix and an extracellular matrix component.

Provided herein is a method of preparing a device comprising a substrate and a plurality of layers that form a laminate coating on said substrate; said method comprising: providing a substrate; and forming a plurality of layers on said substrate to form said laminate coating on said substrate; wherein at least one of said layers comprises a polymer and at least one of said layers comprises one or more active agents; wherein at least a portion of the active agent comprises at least one of extracellular matrix and an extracellular matrix component.

In some embodiments, the extracellular matrix component comprises at least one of: heparin sulfate, chondroitin sulfate, keratan sulfate, hyaluronic acid, collagen, elastin, fibronectin, laminin, merosin, tenascin, vitronectin, and fibrillin.

Provided herein is a method of preparing a device comprising a stent and a plurality of layers that form a laminate coating on said stent; said method comprising: providing a stent; and forming a plurality of layers to form said laminate coating on said stent; wherein at least one of said layers comprises a polymer and at least one of said layers comprises an active agent comprising at least one of extracellular matrix and an extracellular matrix component, wherein said method creates at least one active agent layer defined by a three-dimensional physical space occupied by the active agent and said three dimensional physical space is free of polymer.

Provided herein is a method of preparing a device comprising a substrate and a plurality of layers that form a laminate coating on said substrate; said method comprising: providing a substrate; and forming a plurality of layers to form said laminate coating on said substrate; wherein at least one of said layers comprises a polymer and at least one of said layers comprises an active agent comprising at least one of extracellular matrix and an extracellular matrix component, wherein said method creates at least one active agent layer defined by a three-dimensional physical space occupied by the active agent and said three dimensional physical space is free of polymer.

Provided herein is a method of preparing a device comprising a stent and a plurality of layers that form a laminate coating on said stent; said method comprising: (a) providing a stent; (b) discharging at least one active agent in dry powder form through a first orifice; (c) forming a supercritical or near supercritical fluid solution comprising at least one supercritical fluid solvent and at least one polymer and discharging said supercritical or near supercritical fluid solution through a second orifice under conditions sufficient to form solid particles of the polymer; (d) depositing the polymer and particles of the active agent onto said stent, wherein an electrical potential is maintained between the stent and the polymer and active agent particles, thereby forming said coating; and (e) sintering said polymer under conditions that do not substantially modify activity of said active agent, wherein said active agent comprises at least one of extracellular matrix and an extracellular matrix component.

Provided herein is a method of preparing a device comprising a substrate and a plurality of layers that form a laminate coating on said substrate; said method comprising: (a) providing substrate stent; (b) discharging at least one active agent in dry powder form through a first orifice; (c) forming a supercritical or near supercritical fluid solution comprising at least one supercritical fluid solvent and at least one polymer and discharging said supercritical or near supercritical fluid solution through a second orifice under conditions sufficient to form solid particles of the polymer; (d) depositing the polymer and particles of the active agent onto said substrate, wherein an electrical potential is maintained between the substrate and the polymer and active agent particles, thereby forming said coating; and (e) sintering said polymer under conditions that do not substantially modify activity of said active agent, wherein said active agent comprises at least one of extracellular matrix and an extracellular matrix component.

In some embodiments, step (b) comprises discharging the active agent wherein at least a portion of the active agent is in active form. In some embodiments, step (c) comprises forming solid particles of a bioabsorbable polymer. In some embodiments, step (c) comprises forming solid particles of a durable polymer.

In some embodiments, step (e) comprises forming a polymer layer having a length along a horizontal axis of said device wherein said polymer layer has a layer portion along said length, wherein said layer portion is free of active agent. In some embodiments, step (e) comprises contacting said polymer with a densified fluid. In some embodiments, step (e) comprises contacting said polymer with a densified fluid for a period of time at a temperature of from about 5° C. and 150° C. and a pressure of from about 10 psi to about 500 psi. In some embodiments, step (e) comprises contacting said polymer with a densified fluid for a period of time at a temperature of from about 25° C. and 95° C. and a pressure of from about 25 psi to about 100 psi. In some embodiments, step (e) comprises contacting said polymer with a densified fluid for a period of time at a temperature of from about 50° C. and 85° C. and a pressure of from about 35 psi to about 65 psi.

Provided herein is a method of preparing a device comprising a stent and a plurality of layers that form a laminate coating on said stent; said method comprising: (a) providing a stent; (b) forming a supercritical or near supercritical fluid solution comprising at least one supercritical fluid solvent and a first polymer, discharging said supercritical or near supercritical fluid solution under conditions sufficient to form solid particles of said first polymer, depositing said first polymer particles onto said stent, wherein an electrical potential is maintained between the stent and the first polymer, and sintering said first polymer; (c) depositing active agent particles in dry powder form onto said stent, wherein an electrical potential is maintained between the stent and said active agent particles, and wherein said active agent comprises at least one of extracellular matrix and an extracellular matrix component; and (d) forming a supercritical or near supercritical fluid solution comprising at least one supercritical fluid solvent and a second polymer and discharging said supercritical or near supercritical fluid solution under conditions sufficient to form solid particles of said second polymer, wherein an electrical potential is maintained between the stent and the second polymer, and sintering said second polymer.

Provided herein is a method of preparing a device comprising a substrate and a plurality of layers that form a laminate coating on said substrate; said method comprising: (a) providing a substrate; (b) forming a supercritical or near supercritical fluid solution comprising at least one supercritical fluid solvent and a first polymer, discharging said supercritical or near supercritical fluid solution under conditions sufficient to form solid particles of said first polymer, depositing said first polymer particles onto said substrate, wherein an electrical potential is maintained between the substrate and the first polymer, and sintering said first polymer; (c) depositing active agent particles in dry powder form onto said substrate, wherein an electrical potential is maintained between the substrate and said active agent particles, and wherein said active agent comprises at least one of extracellular matrix and an extracellular matrix component; and (d) forming a supercritical or near supercritical fluid solution comprising at least one supercritical fluid solvent and a second polymer and discharging said supercritical or near supercritical fluid solution under conditions sufficient to form solid particles of said second polymer, wherein an electrical potential is maintained between the substrate and the second polymer, and sintering said second polymer.

In some embodiments, step (c) and step (d) are repeated at least once. In some embodiments, steps (c) and step (d) are repeated 2 to 20 times.

In some embodiments, the active agent comprises at least one of extracellular matrix and an extracellular matrix component, wherein at least a portion of the active agent is in active form. In some embodiments, the active agent is in active form before the method begins, during the method steps, and when the method steps are complete.

In some embodiments, said first and second polymers are bioabsorbable. In some embodiments, said first and second polymers are durable.

In some embodiments, step (d) comprises forming a polymer layer having a length along a horizontal axis of said device wherein said polymer layer has a layer portion along said length, wherein said layer portion is free of active agent.

In some embodiments, sintering said first and/or sintering said second polymer comprises contacting said first and/or second polymer with a densified fluid.

In some embodiments, said contacting step is carried out for a period of from about 1 minute to about 60 minutes. In some embodiments, said contacting step is carried out for a period of from about 10 minutes to about 30 minutes.

In some embodiments, maintaining said electrical potential between said polymer particles and or active agent particles and said stent comprises maintaining a voltage of from about 5 kvolts to about 100 kvolts. In some embodiments, maintaining said electrical potential between said polymer particles and or active agent particles and said stent comprises maintaining a voltage of from about 20 kvolts to about 30 kvolts.

Provided herein is a device prepared by any process described herein.

Provided herein is a method of treating a subject comprising delivering a device described herein in a body lumen of the subject. Provided herein is a method of treating a subject comprising delivering a device described herein in a body of the subject.

Provided herein is a method of treating a subject comprising delivering in the body of the subject a device comprising: a stent; and a plurality of layers that form a laminate coating on said stent, wherein a first layer comprises a first polymer, a second layer comprises an active agent, a third layer comprises a second polymer, a fourth layer comprises the active agent, and a fifth layer comprises a third polymer, wherein the active agent comprises at least one of extracellular matrix and an extracellular matrix component, wherein at least a portion of the active agent is in active form, and wherein at least one of said first polymer, second polymer and third polymer comprises a PLGA copolymer. In some embodiments, the active agent is in active form before the method begins, during the method steps, and when the method steps are complete.

Provided herein is a method of treating a subject comprising delivering in the body of the subject a device comprising: a substrate; and a plurality of layers that form a laminate coating on said substrate, wherein a first layer comprises a first polymer, a second layer comprises an active agent, a third layer comprises a second polymer, a fourth layer comprises the active agent, and a fifth layer comprises a third polymer, wherein the active agent comprises at least one of extracellular matrix and an extracellular matrix component, wherein at least a portion of the active agent is in active form, and wherein at least one of said first polymer, second polymer and third polymer comprises a PLGA copolymer. In some embodiments, the active agent is in active form before the method begins, during the method steps, and when the method steps are complete.

In some embodiments, said method comprises treating restenosis in a blood vessel of the subject.

Provided herein is a method of treating a subject comprising delivering in the body of the subject a device comprising: a stent; and a plurality of layers that form a laminate coating on said stent, wherein a first layer comprises a first polymer, a second layer comprises an active agent, a third layer comprises a second polymer, a fourth layer comprises the active agent, and a fifth layer comprises a third polymer, wherein the active agent comprises at least one of extracellular matrix and an extracellular matrix component, wherein at least a portion of the active agent is in active form, and wherein at least one of said first polymer, second polymer and third polymer comprises a durable polymer. In some embodiments, the active agent is in active form before the method begins, during the method steps, and when the method steps are complete.

Provided herein is a method of treating a subject comprising delivering in the body of the subject a device comprising: a substrate; and a plurality of layers that form a laminate coating on said substrate, wherein a first layer comprises a first polymer, a second layer comprises an active agent, a third layer comprises a second polymer, a fourth layer comprises the active agent, and a fifth layer comprises a third polymer, wherein the active agent comprises at least one of extracellular matrix and an extracellular matrix component, wherein at least a portion of the active agent is in active form, and wherein at least one of said first polymer, second polymer and third polymer comprises a durable polymer. In some embodiments, the active agent is in active form before the method begins, during the method steps, and when the method steps are complete.

In some embodiments, said method comprises treating restenosis in a blood vessel of the subject.

Provided herein is a device comprising: a stent; and a coating comprising an active agent comprising at least one of extracellular matrix and an extracellular matrix component, wherein at least a portion of the active agent is in active form, and a bioabsorbable polymer wherein the coating has an initial polymer amount; wherein when said device is delivered in a body lumen of a subject, at least about 75% of polymer is released from the device 90 days or more after the device is delivered in the body lumen of the subject. In some embodiments, the active agent is in active form before the method begins, during the method steps, and when the method steps are complete.

In some embodiments, when said device is delivered in a body lumen of a subject about 75% of polymer is released from the device about 90 days after the device is delivered in the body lumen of the subject. In some embodiments, when said device is delivered in a body lumen of a subject about 85% of polymer is released from the device about 90 days after the device is delivered in the body lumen of the subject. In some embodiments, when said device is delivered in a body lumen of a subject about 100% of polymer is released from the device about 90 days after the device is delivered in the body lumen of the subject.

In some embodiments, the subject is a pig and the amount of polymer released from the device is determined as follows: delivering the device in the pig's blood vessel lumen; euthanizing the pig at predetermined period of time after the device is delivered in the pig's blood vessel lumen and explanting the device; and measuring the amount of polymer released from the device. In some embodiments, measuring the amount of polymer released from the device comprises LC/MS/MS measurements. In some embodiments, measuring the amount released from the device comprises weight loss measurement. In some embodiments, weight loss measurement comprises measuring an amount of polymer remaining in the device and subtracting said remaining amount from the initial amount present in the device prior to delivering the device to the pig's blood vessel lumen.

In some embodiments the dissolution profile of the polymer and the elution profile of the active agent is measured using tests noted herein using tissue samples tested following in-vivo implantation of stents prepared and implanted as described herein. In some embodiments the dissolution profile of the polymer and the elution profile of the active agent is measured by in-vitro testing described herein of stents prepared as described herein.

In some embodiments, there is a correlation between the dissolution of at least one of the polymers and the release of the active agent. In some embodiments, the correlation is a parallel relationship between the release of the active agent, and the dissolution profile of the polymer measured between at least two time points (and may or may not include the time points). In some embodiments, the correlation is a parallel relationship between the release of the active agent, and the dissolution profile of the polymer measured between at least three time points. In some embodiments, the parallel relationship has a variation of about 10%, and is still considered parallel. In some embodiments, the parallel relationship has a variation of about 25%, and is still considered parallel. In some embodiments, the parallel relationship has a variation of about 30%, and is still considered parallel. In some embodiments, the correlation is non-parallel.

In some embodiments, wherein there is at least one of an association, a correlation, a coincident relationship between the release of the active agent and the dissolution profile of the polymer, the potential for inflammation of the vessel is controlled. In some embodiments, wherein there is at least one of an association, a correlation, a coincident relationship between the release of the active agent and the dissolution rate of the polymer, the potential for inflammation of the vessel is controlled. In some embodiments, wherein there is at least one of an association, a correlation, a coincident relationship between the release of the active agent and the dissolution rate of the polymer, there is an acceptable level and/or amount inflammation of the vessel. In some embodiments, wherein there is at least one of an association, a correlation, a coincident relationship between the release of the active agent and the dissolution rate of the polymer, there is substantially no inflammation of the vessel. As used herein, substantially no inflammation means no inflammation that is unacceptable to a clinician. In some embodiments, wherein there is at least one of an association, a correlation, a coincident relationship between the release of the active agent and the dissolution rate of the polymer, the device provides reduced inflammation over the course of polymer dissolution compared to a conventional stent.

Provided herein is a method of treating a subject comprising delivering a device as described herein in a body lumen. Provided herein is a method of treating a subject comprising delivering a device as described herein in a body of a subject.

In some embodiments, coating on an albuminal surface of said stent has a greater thickness than coating on a luminal surface of said stent. In some embodiments, a ratio of coating on the albuminal surface to coating on the luminal surface of the device is 80:20. In some embodiments, a ratio of coating on the albuminal surface to coating on the luminal surface of the device is 75:25. In some embodiments, a ratio of coating on the albuminal surface to coating on the luminal surface of the device is 70:30. In some embodiments, a ratio of coating on the albuminal surface to coating on the luminal surface of the device is 60:40.

In some embodiments, said stent is a coronary stent, a vascular stent, a peripheral stent, biliary stent, and intercranial stent.

Provided herein is a stent delivery system comprising: an elongate member having an inflation lumen and a guidewire lumen therein; a balloon having an interior that is in fluid communication with the inflation lumen; and a coated stent mounted on the balloon, wherein the coated stent comprises a stent and a plurality of layers that form a coating on said stent; wherein at least one of said layers comprises a polymer and at least one of said layers comprises an active agent, wherein the active agent comprises at least one of: extracellular matrix and an extracellular matrix component.

In some embodiments, the coating is a laminate coating.

In some embodiments, the extracellular matrix component comprises at least one of: heparin sulfate, chondroitin sulfate, keratan sulfate, hyaluronic acid, collagen, elastin, fibronectin, laminin, merosin, tenascin, vitronectin, and fibrillin.

In some embodiments, the polymer is at least one of: a bioabsorbable polymer and a durable polymer.

Provided herein is a method of preparing a stent delivery system comprising an elongate member having an inflation lumen and a guidewire lumen therein, a balloon having an interior that is in fluid communication with the inflation lumen, a stent and a plurality of layers that form a laminate coating on said stent; said method comprising: providing the stent; forming a coated stent by forming a plurality of layers to form said laminate coating on said stent; wherein at least one of said layers comprises a polymer and at least one of said layers comprises an active agent comprising at least one of extracellular matrix and an extracellular matrix component; and mounting the coated stent to the balloon, wherein said method creates at least one active agent layer on the stent, the active agent layer defined by a three-dimensional physical space occupied by the active agent and said three dimensional physical space is free of polymer.

Provided herein is a coated implantable medical device, comprising: a substrate; and a coating disposed on said substrate, wherein said coating comprises at least one polymer and an agent comprising at least one of extracellular matrix and an extracellular matrix component; wherein substantially all of the active agent remains within said coating and on said substrate until the implantable device is deployed at an intervention site inside the body of a subject, wherein upon deployment of said medical device in the body of said subject a portion of the active agent is delivered at said intervention site along with at least a portion of said polymer, and wherein the coated device is adapted to be delivered to a body lumen.

In some embodiments, upon deployment within the body of the subject, the coating partially or entirely dissociates from or is transferred from the device and the active agent is deposited at the site of placement of the device within the body along with at least a portion of said polymer. In some embodiments, the coating formulation provides at least one of: at least 10% deposition of the active agent within the body, at least 20% deposition of the active agent within the body, at least 30% deposition of the active agent within the body, at least 50% deposition of the active agent within the body, at least 75% deposition of the active agent within the body, at least 85% deposition of the active agent within the body, at least 90% deposition of the active agent within the body, at least 95% deposition of the active agent within the body, and at least 99% deposition of the active agent within the body.

In some embodiments, deposition is achieved within one day after deployment of the device within the body. In some embodiments, deposition is achieved instantaneously after deployment of the device within the body. In some embodiments, the coating dissociates from the substrate upon deployment of the device at the body site by plastic deformation of the coating, by compressive force, shear force, internally generated and/or externally generated force, shearing of the coating from the surface of the device, and/or bulk migration of the coating from the device into the tissue at the body site.

One embodiment provides a percutaneous medical device with a coating that, upon deployment in the body, delivers some or all of the coating to a specific therapeutic site in the body. The device can be a permanent implant, for example a stent, or a transient device, such as a balloon catheter. Several other types of devices are contemplated in the present application. Another embodiment provides intraocular active agent delivery device. Another embodiment provides a surgical tool. An illustrative but non-exhaustive list of devices contemplated herein is provided below.

Some embodiments provide devices that can serve interventional purposes in addition to delivery of therapeutics, such as a 'cutting balloon'.

In one embodiment, delivery of the coating to the tissue at a site inside the body of a subject occurs by a coating that dissociates from the device via: (1) plastic deformation of the coating by compressive, shear, internally generated and/or externally generated forces, (2) shearing of the coating from the surface of the device, (3) bulk migration of the coating from the device into the tissue, and/or (4) separation from the device due to hydrolysis of the polymer, resulting in a week bond between the coating and the device. The devices provided herein all for the transfer of some or all of the coating from the device to the local tissue to provide a targeted therapeutic effect.

The devices and method provided herein allow for intervention at targeted disease-states that in some embodiments are site-specific medical indications, including without limitation lesions, occlusions, infections, tumors, regional sites for tumor therapy such as intraperitoneal delivery, local sites of angiogenesis or inflammation such as sites within the eye or retina, gingival delivery for periodontal disease, within the joints in the synovial fluid, in the ventricle to deliver to the CNS spinal fluid, and embolic devices that also deliver active agents. The coated device may be adapted to be delivered to a peripheral vessel, and/or to lumens or areas peripheral to the heart and to coronary arteries.

The devices and methods provided herein are contemplated to be used in the treatment of any disease that would benefit from targeted local delivery of a pharmaceutical and/or active biological agent. Examples of diseases include without limitation coronary artery disease, peripheral artery disease (e.g. carotid, femoral, etc), urinary tract obstructions and/or infections, biliary tract obstructions and/or infections, tumors/cancer, vascular obstructions (e.g. embolisms, lacunar or embolic stroke, varicose veins, etc.), neurological disorders, post-operative infections, diseases of the GI tract, diseases of the reproductive system (fallopian tubes), diseases of the Ear-Nose-Throat and any disease associated with an impairment of flow through a body tubular structure (e.g., dry eye).

For example, and without limitation, the devices and methods provided herein may be advantageously employed in the local treatment of vascular diseases, the local treatment of internal diseases via providing active agent 'upstream' in the vasculature from disease sites for: infection, oncology, etc., the local or regional treatment of tumors, the local treatment infections, particularly those that are hard to treat with systemic antibiotics, for example due to poor circulation to the infected site (e.g.; orthopedic, extremities in diabetics, etc), the local treatment of neurological disorders such as pain ailments.

In embodiments involving vascular diseases, the devices and methods provided herein may advantageously employ coating technology to mitigate the formation of free particles that could become entrained in the blood stream and cause negative complications such as emboli. For example, some embodiments are based on the utilization of soft coatings that undergo facile bulk flow under stress. Other embodiments are based on the utilization of biodegradable materials such as PLGA polymers that are mechanically sound at the time of implant, then over time degrade to lose their cohesion and/or adhesion to the surface of the device. Yet other embodiments are based on utilization of layered or laminated coatings to directly control the transfer mechanisms of plastic deformation, shear and bulk-migration. Yet other embodiments use all three aspects described above.

In some embodiments, the coating dissociates from the substrate through facile bulk flow under stress. In some embodiments, the coating comprises laminated layers that allow direct control of the transfer of plastic deformation, shear and bulk-migration.

In some embodiments, the extracellular matrix component comprises at least one of: heparin sulfate, chondroitin sulfate, keratan sulfate, hyaluronic acid, collagen, elastin, fibronectin, laminin, merosin, tenascin, vitronectin, and fibrillin.

In some embodiments, the substrate is an angioplasty balloon.

In some embodiments, the substrate is a cutting balloon.

In some embodiments, the coating comprises a soft material that undergoes plastic deformation at pressures provided by the inflation of the balloon. In some embodiments, the coating comprises a soft material that undergoes plastic deformation at pressures provided by the inflation of the balloon at 2-25 ATM. In some embodiments, the coating comprises a soft material that undergoes plastic deformation at pressures provided by the inflation of the balloon at 10-18 ATM.

In some embodiments, the coating comprises material that dissociates upon implant in the body in response to external stimuli. In some embodiments, stimuli comprise stimuli that induce a chemical transformation of the coating material. In some embodiments, the chemical transformation involves an acid base reaction. In some embodiments, the stimuli that induce a chemical transformation of the coating material comprise one or more of light, heat, and radiation. In some embodiments, the stimuli comprise stimuli that induce mechanical forces to augment the transfer of the coating into the tissue. In some embodiments, the stimuli that induce mechanical forces to augment the transfer of the coating into the tissue comprise ultrasound, translation, rotation, vibration and combinations thereof. In some embodiments, the coating comprises material that dissociates upon implant in the body in response to in-situ enzymatic reactions and/or material that dissociates upon implant in the body due to hydrolysis of the polymer, resulting in a week bond between the coating and the device.

In some embodiments, the at least one polymer is a durable polymer. In some embodiments, the durable polymer is selected from the group consisting of: polyester, aliphatic polyester, polyanhydride, polyethylene, polyorthoester, polyphosphazene, polyurethane, polycarbonate urethane, aliphatic polycarbonate, silicone, a silicone containing polymer, polyolefin, polyamide, polycaprolactam, polyamide, polyvinyl alcohol, acrylic polymer, acrylate, polystyrene, epoxy, polyethers, celluiosics, expanded polytetrafluoroethylene, phosphorylcholine, polyethyleneyerphthalate, polymethylmethavrylate, poly(ethylmethacrylate/n-butylmethacrylate), parylene C, polyethylene-co-vinyl acetate, polyalkyl methacrylates, polyalkylene-co-vinyl acetate, polyalkylene, polyalkyl siloxanes, polyhydroxyalkanoate, polyfluoroalkoxyphasphazine, poly(styrene-b-isobutylene-b-styrene), poly-butyl methacrylate, poly-bytadiene, and blends, combinations, homopolymers, condensation polymers, alternating, block, dendritic, cross-linked, and copolymers thereof.

In some embodiments, the coating comprises one or more resorbable polymers. In some embodiments, the one or more resorbable polymers are selected the group consisting of: PLGA (poly(lactide-co-glycolide); DLPLA—poly(dl-lactide); LPLA—poly(l-lactide); PGA—polyglycolide; PDO—poly(dioxanone); PGA-TMC—poly(glycolide-co-trimethylene carbonate); PGA-LPLA—poly(l-lactide-co-glycolide); PGA-DLPLA—poly(dl-lactide-co-glycolide); LPLA-DLPLA—poly(l-lactide-co-dl-lactide); and PDO-PGA-TMC—poly(glycolide-co-trimethylene carbonate-co-dioxanone). In some embodiments, the one or more resorbable polymers comprise between 1% and 95% glycolic acid content PLGA-based polymer. In some embodiments, the coating comprises a polymer having a dry modulus between 3,000 and 12,000 KPa.

In some embodiments, the coating comprises a hydrogel.

In some embodiments, the polymer film comprises a microstructure. In some embodiments, active agent particles are sequestered or encapsulated within said microstructure. In some embodiments, said microstructure comprises microchannels, micropores and/or microcavities.

In some embodiments, the coating is formed on said substrate through a process comprising depositing said polymer active agent by an e-RESS, an e-SEDS, or an e-DPC process. In some embodiments, forming said coating provides improved adherence of the coating to the substrate prior to deployment of the medical device at a body site and facilitates dissociation of said coating from said substrate after deployment of the medical device at said body site.

In some embodiments, the device is a cutting balloon having coated wire shaped in the form of an outward pointing wedge.

In some embodiments, the coating forms a sheath.

In some embodiments, the device comprises an inflatable balloon. In some embodiments, the coating comprises a soft material that undergoes plastic deformation at pressures provided by the inflation of the balloon. In some embodiments, the coating comprises a soft material that undergoes plastic deformation at pressures provided by the inflation of the balloon at 2-25 ATM. In some embodiments, the coating comprises a soft material that undergoes plastic deformation at pressures provided by the inflation of the balloon at 10-18 ATM.

In some embodiments, the polymer becomes soft after implantation. In some embodiments, the coating comprises a polymer that becomes soft after implant by hydration, degradation or by a combination of hydration and degradation.

In some embodiments, the device is adapted for delivery to at least one of a peripheral artery, a peripheral vein, a carotid artery, a vein, an aorta, and a biliary duct. In some embodiments, the device is adapted for delivery to a superficial femoral artery. In some embodiments, the device is adapted for delivery to a renal artery. In some embodiments, the device is adapted for delivery to an iliac artery. In some embodiments, the device is adapted for delivery to a bifurcated vessel. In some embodiments, the device is adapted for delivery to a vessel having a side branch at an intended delivery site of the vessel.

In some embodiments, the polymer is a durable polymer. In some embodiments, the polymer comprises a cross-linked durable polymer. In some embodiments, the polymer comprises a thermoset material. In some embodiments, the polymer comprises a cross-linked bioabsorbable polymer.

In some embodiments, the coating comprises a plurality of layers deposited on a device framework to form said device. In some embodiments, the plurality of layers comprises five layers deposited as follows: a first polymer layer, a first active agent layer, a second polymer layer, a second active agent layer and a third polymer layer. In some embodiments, the active agent and polymer are in the same layer; in separate layers or form overlapping layers. In some embodiments, the plurality of layers comprises at least 4 or more layers. In some embodiments, the plurality of layers comprises 10, 20, 50, or 100 layers. In some embodiments, the plurality of layers comprises alternate active agent and polymer layers. In some embodiments, the active agent layers are substantially free of polymer and the polymer layers are substantially free of active agent. In some embodiments, the polymer provides radial strength for the device. In some embodiments, the polymer provides durability for the device. In some embodiments, the polymer is impenetrable by a broken piece of the device framework.

The base (framework) of the implantable medical device may be thin to be a base for the polymer to build upon, and the polymer itself may provide the strength and durability to withstand the forces encountered in the body, including but not limited to internal forces from blood flow, and external forces, such as may be encountered in peripheral vessels, other body lumens, and other implantation sites. The coatings and coating methods provided herein provide substantial protection from these by establishing a multi-layer coating which can be bioabsorbable or durable or a combination thereof, and which can both deliver active agents and provide elasticity and radial strength for the vessel (or other site) in or to which it is delivered.

In some embodiments, the device comprises a geometric configuration that maximizes the shear forces on the coating. In some embodiments, the geometric design of the device provides (1) increased and/or concentrated force to plastically deform the active agent+polymer coating (2) decreased force of adhesion of the coating to the substrate. In some embodiments, geometric aligns the forces of deformation along a shear plane as opposed to direct compression. In some embodiments, geometric design provides for: (1) increased efficiency in terms of % of the coating transferred into the site upon deployment of the device in the body (2) increased precision in amount of active agent/polymer transferred (3) utilization of 'harder/stiffer' materials (biopolymers) that would otherwise not deform and/or not bulk-migrate under deployment conditions and/or (4) minimize the chance of particulate shedding.

In some embodiments, the device comprises a geometric configuration comprising layers. In some embodiments, the geometric configuration comprises a coating having a laminate structure. In some embodiments, the laminate structure in the coating modulates and controls the plastic deformation, shearing and bulk-migration of the coating into the tissue.

In some embodiments, the device is adapted for delivery to at least one of a peripheral artery, a peripheral vein, a carotid artery, a vein, an aorta, and a biliary duct.

Some of the embodiments provided herein are based on transfer of the coating from the device to the body tissue involve one or more of (1) plastic deformation by compressive and/or shear force induced by deployment and/or induced by the native surrounding tissue and/or induced by the in-growth of new tissue catalyzed by the deployment of the device (2) shear transfer (wiping off) of the coating from the device outward (relative to the device) into the tissue, (3) bulk migration, and (4) separation from the device due to hydrolysis of the polymer, resulting in a week bond to the device.

Plastic deformation is the change in the physical shape of the coating upon deployment by pressures induced on the device after deployment. Plastic deformation results in increasing the contact area of the coating on the tissue and decreasing the contact area of the coating on the device. This change in contact area results in some or all of the coating being preferentially exposed to the tissue instead of the device.

Shear transfer is the force (or component of forces) orthogonal to the device that would drive the coating away from the device substrate. This could be induced on the device by deployment, pressure-response from the surrounding tissue and/or in-growth of tissue around the coating.

Bulk migration is the incorporation of the coating onto/into the tissue provided by the removal of the device and/or provided by degradation of the coating over time and/or provided by hydration of the coating over time. Degradation and hydration of the coating may reduce the coating's cohesive and adhesive binding to the device, thereby facilitating transfer of the coating to the tissue.

One embodiment may be described by analogy to contact printing whereby a biochemically active 'ink' (the polymer+ active agent coating) from a 'die' (the device) to the 'stock' (the site in the body).

The devices and methods described in conjunction with some of the embodiments provided herein are advantageously based on specific properties provided for in the active agent-delivery formulation. One such property, especially well-suited for non-permanent implants such as balloon catheters, cutting balloons, etc. is 'soft' coating that undergoes plastic deformation at pressures provided by the inflation of the balloon (range 2-25 ATM, typically 10-18 ATM). Another such property, especially well-suited to permanent implants such as stents is coatings where the polymer becomes 'soft' at some point after implant either by hydration or by degradation or by combinations of hydration and degradation.

Some embodiments provide devices that can advantageously be used in conjunction with methods that can aid/promote the transfer of the coating. These include introducing stimuli to the coated device once on-site in the body (where the device is delivered either transiently or permanently). Such stimuli can be provided to induce a chemical response (light, heat, radiation, etc.) in the coating or can provide mechanical forces to augment the transfer of the coating into the tissue (ultrasound, translation, rotation, vibration and combinations thereof).

One embodiment provides coated percutaneous devices (e.g.; balloons) that, upon deployment at a specific site in the patient, transfer some or all of the active agent-delivery formulation (5-10%, 10-25%, 25-50%, 50-90%, 90-99%, 99-100%) to the site of therapeutic demand.

Another embodiment provides catheter-based devices where the active agent-delivery formulation is delivered to the therapeutic site in the vasculature via inflation of a balloon.

One illustration devices provided herein include a cutting balloon for the treatment of vascular disease (e.g.; occluded lesions in the coronary or peripheral vasculature). In this embodiment, the coating may be preferentially located on the 'cutting wire' portion of the device. Upon deployment, the wire pushes into the plaque to provide the desired therapeutic 'cutting' action. During this cutting, the polymer and active agent coating is plastically deformed off of the wire by the combination of compressive and shear forces acting on the wire-leaving some or all of the coating embedded in the plaque and/or artery wall. A similar approach may be applied to delivery of oncology active agents (a) directly to tumors and/or, (b) to the arteries delivering blood to the tumors for site-specific chemotherapy, and/or (c) to the voids left after the removal of a tumor (lumpectomy). These oncology (as well as other non-vascular) applications may not require the 'cutting' aspects and could be provided by coatings directly onto the balloon or onto a sheath over the balloon or according to an embodiment wherein the coating forms a sheath over the deflated (pleated) balloon.

A cutting balloon embodiment described herein provides several advantages. Such embodiment allows for concentrating the mechanical force on the coating/wire as the balloon is inflated—the wire may serve to concentrate the point-of-contact-area of the balloon expansion pressure resulting in a much higher force for plastic deformation of the active agent and polymer coating vs. the non-cutting plain balloon which may distribute the pressure over a much larger area (therefore lower force proportional to the ratio of the areas). Embodiments involving a cutting balloon provide for the use of polymers that would otherwise be too rigid (higher modulus) to deform from a non-cutting balloon.

One pervasive challenge to alternative technologies to deliver active agents via percutaneous catheter devices is 'how to insure that the active agent-formulation is not shed during positioning of the device to the therapeutic site. In other words: how to insure that the active agent is not washed off during insertion. This challenge leads to an advantage of the current invention vs. prior art because of the specific use of a polymeric formulation in the coating and the method of creating the coating and its formulation.

Embodiments provided herein maintain the active agent within a mechanically sound polymeric coating (as opposed to coated as particles or formulated in a viscous oil), the coating is much more likely to maintain adhesion to the device during insertion. In these embodiments, there is little or no release of the coating until the device is deployed at the therapeutic site.

One particular advantage provided herein for embodiments wherein the device is a stent (coronary, peripheral, etc.) is the ability to deliver the coating to a much greater area/volume of the arterial wall due to the 'spreading' of the active agent and polymer formulation. This is in contrast to a traditional DES that delivers active agent solely by diffusion of the active agent out of the coating that permanently remains on the stent strut. This embodiment may provide clinical advantages, especially as stent struts advance to thinner and smaller diameters, of treating more, and more homogenously, the entire site of arterial injury caused by deployment of the stent.

Other embodiments provided herein are based on geometric configurations of the device that optimize both the deformation and the bulk-migration of the coating from the device. In one embodiment wherein the device is a cutting balloon, the (coated) wire of the cutting balloon is shaped like a wedge, pointed outward.

Provided herein are device geometries that maximize the shear forces on the coating. Such geometric design of the device provides two advantages: (1) increases (concentrates) the force to plastically deform the active agent and polymer coating (2) decreases the force of adhesion of the coating. For example, a wedge-shape aligns the forces of deformation along a shear plan as opposed to direct compression. This embodiment provides for: (1) increased efficiency in terms of % of the coating transferred (2) increased precision in amount transferred on a case-by-case basis (3) utilization of 'harder/stiffer' materials (biopolymers) that would otherwise not deform and/or not bulk-migrate under deployment conditions (4) minimize the chance of particulate shedding via purposefully designing the shape and direction of both the deformation and bulk migration. For example for a wedge, particles would be less likely because the coating would be pre-disposed as a shear from the device in a sheet form—with the use of soft materials, this may be illustrated as a coating of silicone caulk being extruded from the pressure of a rod being pushed into a mattress.

Another embodiment provide a geometric arrangement of the coating whereby layers, e.g. a laminate structure, are provided in the coating to modulate and control the plastic deformation, shearing and bulk-migration of the coating into the tissue.

Provided herein are devices and methods adapted for the peripheral vessels of the vasculature, which may exhibit symptoms of peripheral artery disease. These vessels may require release of a active agent which extends over a longer period of time than a coronary lesion might, thus, the methods and devices provided herein can be formulated to provide extended release of the active agent by controlling the release such that a minimal of active agent is washed away over time allowing more of the actual active agent deposited on the substrate to be eluted into the vessel. This provides a higher ratio of therapeutic active agent to active agent lost during delivery and post delivery, and thus the total amount of active agent can be lower if less is lost during and post delivery. This can be useful for active agents which may have higher toxicities at lower concentrations, but which may be therapeutic nonetheless if properly controlled. The methods and devices provided herein are capable of eluting the active agent in a more controlled manner, and, thus, less active agent overall is deposited on the substrate when less is lost by being washed away during and post delivery to the delivery site.

Provided herein is a method of delivering a therapeutic agent to a site within the body of the subject comprising: providing a coated implantable medical device, comprising a substrate; and a coating disposed on said substrate, wherein said coating comprises at least one polymer and at least one active agent comprising at least one of extracellular matrix and an extracellular matrix component; wherein substantially all of the active agent remains within said coating and on said substrate until the implantable device is deployed at an intervention site inside the body of a subject and wherein upon deployment of said medical device in the body of said subject a portion of said active agent is delivered at said intervention site; and disposing the medical device at a selected site within the body of the subject, wherein the device is adapted for delivery to a body lumen.

In some embodiments, upon deployment within the body of the subject, the coating partially or entirely dissociates from the device and the active agent is deposited at the site of placement of the device within the body. In some embodiments, the coating formulation provides at least one of: at least 10% deposition of the active agent within the body, at least 20% deposition of the active agent within the body, at least 30% deposition of the active agent within the body, at least 50% deposition of the active agent within the body, at least 75% deposition of the active agent within the body, at least 85% deposition of the active agent within the body, at least 90% deposition of the active agent within the body, at least 95% deposition of the active agent within the body, and at least 99% deposition of the active agent within the body. In some embodiments, the coating dissociates from the substrate upon deployment of the device at the body site by plastic deformation of the coating, by compressive force, shear force, internally generated and/or externally generated force, shearing of the coating from the surface of the device, and/or bulk migration of the coating from the device into the tissue at the body site. In some embodiments, the method further comprises applying external stress so that the coating dissociates from the substrate through facile bulk flow under stress.

In some embodiments, the coating comprises biodegradable materials that are mechanically sound at the time of implant, then over time degrade to lose their cohesion and/or adhesion to the surface of the device.

In some embodiments, the extracellular matrix component comprises at least one of: heparin sulfate, chondroitin sulfate, keratan sulfate, hyaluronic acid, collagen, elastin, fibronectin, laminin, merosin, tenascin, vitronectin, and fibrillin.

In some embodiments, the substrate is an angioplasty balloon. In some embodiments, the substrate is a cutting balloon. In some embodiments, the coating comprises a soft material that undergoes plastic deformation at pressures provided by the inflation of the balloon and the method further comprises applying at pressures provided by the inflation of the balloon. In some embodiments, the method comprises applying the inflation of the balloon at 2-25 ATM.

In some embodiments, the coating comprises material that dissociates upon implant in the body in response to external stimuli. In some embodiments, the method comprises providing stimuli that induce a chemical transformation of the coating material. In some embodiments, the chemical transformation involves an acid base reaction. In some embodiments, the stimuli comprise one or more of light, heat, and radiation. In some embodiments, the method comprises providing stimuli that induce mechanical forces to augment the transfer of the coating into the tissue. In some embodiments, the stimuli that induce mechanical forces to augment the transfer of the coating into the tissue comprise ultrasound, translation, rotation, vibration and combinations thereof. In some embodiments, the coating comprises material that dissociates upon implant in the body in response to in-situ enzymatic reactions.

In some embodiments, the site in the body of the subject is the site of at least one of: a tumor or a void created by removal of tissue/tumor; vascular occlusion or stenosis; an infection; a wound; a diseased conduit in the body; and a conduit in the body fluidly connected to a disease site.

In some embodiments, the device is adapted for delivery to at least one of a superficial femoral artery, a renal artery, an iliac artery, and a bifurcated vessel a vessel having a side branch at an intended delivery site of the vessel. In some embodiments, the device is adapted for delivery to at least one of a peripheral artery, a peripheral vein, a carotid artery, a vein, an aorta, and a biliary duct.

Some embodiments of the devices described herein further comprise a pharmaceutical agent. In some embodiments, the pharmaceutical agent is selected from rapamycin, a prodrug, a derivative, an analog, a hydrate, an ester, and a salt thereof; wherein at least a portion of the pharmaceutical agent is in crystalline form.

In some embodiments, the device comprises a first polymer that comprises a PLGA copolymer with a ratio of about 40:60 to about 60:40 and a second polymer that comprises a PLGA copolymer with a ratio of about 70:30 to about 90:10. In some embodiments, the first polymer is PLGA copolymer having a molecular weight of about 10 kD and the second polymer is a PLGA copolymer having a molecular weight of about 19 kD. In some embodiments, measuring the in vitro dissolution rate of said polymers comprises contacting the device with elution media and determining polymer weight loss at one or more selected time points.

FIG. 1 depicts a cross sectional view of a device according to an embodiment herein, for non-limiting example, a stent strut, comprising a substrate 6 having a coating 2 coated thereon with a polymer 4 and ECM 8 or at least one ECM component.

Figure 2:
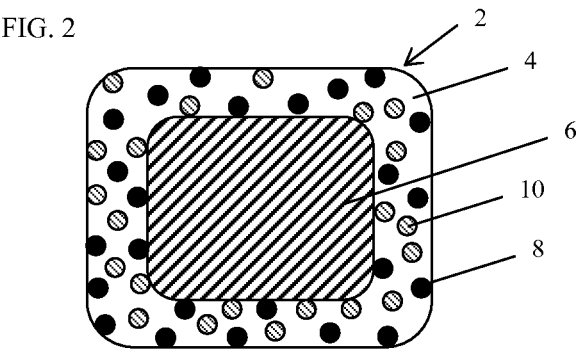
FIG. 2 depicts a cross sectional view of a device according to an embodiment herein, for non-limiting example, a stent strut, comprising a substrate coated with a polymer and ECM or at least one ECM component and a pharmaceutical agent.

FIG. 2 depicts a cross sectional view of a device according to an embodiment herein, for non-limiting example, a stent strut, comprising a substrate 6 having a coating 2 coated thereon with a polymer 4 and ECM 8 or at least one ECM component and a pharmaceutical agent 10.

Figure 3:
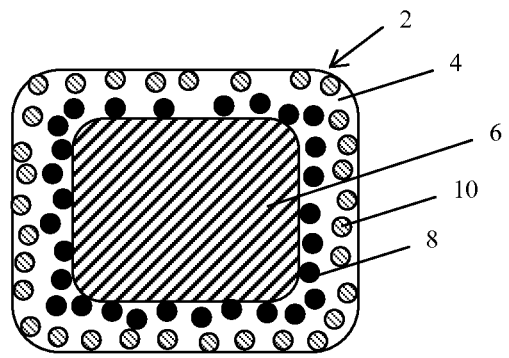
FIG. 3 depicts a cross sectional view of a device according to an embodiment herein, for non-limiting example, a stent strut, comprising a substrate coated with a polymer and ECM or at least one ECM component and a pharmaceutical agent, wherein the pharmaceutical agent is in a layer of the coating that is closest to the device surface than the layer of the coating closest to the substrate which has the ECM or at least one ECM component.

FIG. 3 depicts a cross sectional view of a device according to an embodiment herein, for non-limiting example, a stent strut, comprising a substrate 6 having a coating 2 coated thereon with a polymer 4 and ECM 8 or at least one ECM component and a pharmaceutical agent 10, wherein the pharmaceutical agent 10 is in a layer of the coating 2 that is closest to the device surface than the layer of the coating closest to the substrate 6 which has the ECM 8 or at least one ECM component.

EXAMPLES

The following examples are provided to illustrate selected embodiments. They should not be considered as limiting the scope of the invention, but merely as being illustrative and representative thereof. For each example listed below, multiple analytical techniques may be provided. Any single technique of the multiple techniques listed may be sufficient to show the parameter and/or characteristic being tested, or any combination of techniques may be used to show such parameter and/or characteristic. Those skilled in the art will be familiar with a wide range of analytical techniques for the characterization of active agent/polymer coatings. Techniques presented here, but not limited to, may be used to additionally and/or alternatively characterize specific properties of the coatings with variations and adjustments employed which would be obvious to those skilled in the art.
Sample Preparation Generally speaking, coatings on stents, on coupons, or samples prepared for in-vivo models are prepared as below. Nevertheless, modifications for a given analytical method are presented within the examples shown, and/or would be obvious to one having skill in the art. Thus, numerous variations, changes, and substitutions will now occur to those skilled in the art without departing from the invention. It should be understood that various alternatives to the embodiments of the invention described herein and examples provided may be employed in practicing the invention and showing the parameters and/or characteristics described.
Coatings on Stents Coated stents as described herein and/or made by a method disclosed herein are prepared. In some examples, the coated stents have a targeted thickness of ~15 microns (~5 microns of active agent). In some examples, the coating process is PAPAP (Polymer, sinter, Active agent, Polymer, sinter, Active agent, Polymer, sinter) using deposition of active agent in dry powder form and deposition of polymer particles by RESS methods and equipment described herein. In the illustrations below, resulting coated stents may have a 3-layer coating comprising polymer (for example, PLGA) in the first layer, active agent (for example, ECM) in a second layer and polymer in the third layer, where a portion of the third layer is substantially active agent free (e.g. a sub-layer within the third layer having a thickness equal to a fraction of the thickness of the third layer). As described layer, the middle layer (or active agent layer) may be overlapping with one or both first (polymer) and third (polymer) layer. The overlap between the active agent layer and the polymer layers is defined by extension of polymer material into physical space largely occupied by the active agent. The overlap between the active agent and polymer layers may relate to partial packing of the active agent particles during the formation of the active agent layer. When active agent particles are deposited on top of the first polymer layer, voids and or gaps may remain between the active agent particles. The voids and gaps are available to be occupied by particles deposited during the formation of the third (polymer) layer. Some of the particles from the third (polymer) layer may rest in the vicinity of active agent particles in the second (active agent) layer. When the sintering step is completed for the third (polymer) layer, the third polymer layer particles fuse to form a continuous film that forms the third (polymer) layer. In some embodiments, the third (polymer) layer however will have a portion along the longitudinal axis of the stent whereby the portion is free of contacts between polymer material and active agent particles. The portion of the third layer that is substantially of contact with active agent particles can be as thin as 1 nanometer.

Polymer-coated stents having coatings comprising polymer but no active agent are made by a method disclosed herein and are prepared having a targeted thickness of, for example, ~5 microns. An example coating process is PPP (PLGA, sinter, PLGA, sinter, PLGA, sinter) using RESS methods and equipment described herein. These polymer-coated stents may be used as control samples in some of the examples, infra.

In some examples, the stents are made of a cobalt-chromium alloy and are 5 to 50 mm in length, preferably 10-20 mm in length, with struts of thickness between 20 and 100 microns, preferably 50-70 microns, measuring from an albuminal surface to a luminal surface, or measuring from a side wall to a side wall. In some examples, the stent may be cut lengthwise and opened to lay flat be visualized and/or assayed using the particular analytical technique provided.

The coating may be removed (for example, for analysis of a coating band and/or coating on a strut, and/or coating on the albuminal surface of a flattened stent) by scraping the coating off using a scalpel, knife or other sharp tool. This coating may be sliced into sections which may be turned 90 degrees and visualized using the surface composition techniques presented herein or other techniques known in the art for surface composition analysis (or other characteristics, such as crystallinity, for example). In this way, what was an analysis of coating composition through a depth when the coating was on the stent or as removed from the stent (i.e. a depth from the albuminal surface of the coating to the surface of the removed coating that once contacted the strut or a portion thereof), becomes a surface analysis of the coating which can, for example, show the layers in the slice of coating, at much higher resolution. Coating removed from the stent may be treated the same way, and assayed, visualized, and/or characterized as presented herein using the techniques described and/or other techniques known to a person of skill in the art.

Coatings on Coupons

In some examples, samples comprise coupons of glass, metal, e.g. cobalt-chromium, or another substance that are prepared with coatings as described herein, with a plurality of layers as described herein, and/or made by a method disclosed herein. In some examples, the coatings comprise polymer. In some examples, the coatings comprise polymer and active agent. In some examples, the coated coupons are prepared having a targeted thickness of ~10 microns (with ~5 microns of active agent), and have coating layers as described for the coated stent samples, infra.

Coatings on Substrates Other than Stents

Where coating is on a substrate other than a stent the coating may be prepared as noted herein, and the coating may be removed by a stimulation means as designed (and described herein). For example, wherein the substrate is an inflatable balloon, expanding and deflating the balloon may dissociate the coating (or a portion thereof) from the balloon. If the coating is designed to dissociate from the substrate with another and/or alternative stimulation means (whether physical, chemical, or other means described herein), then the additional stimulation means may be used to remove the coating from the substrate. The coating may alternatively (or additionally) be removed by scraping the coating from the substrate, as noted in the stent preparation description herein.

Sample Preparation for In-Vivo Models

Devices comprising stents having coatings disclosed herein are implanted in the porcine coronary arteries of pigs (domestic swine, juvenile farm pigs, or Yucatan miniature swine). Porcine coronary stenting is exploited herein since such model yields results that are comparable to other investigations assaying neointimal hyperplasia in human subjects. The stents are expanded to a 1:1.1 balloon:artery ratio. At multiple time points, animals are euthanized (e.g. t=1 day, 7 days, 14 days, 21 days, and 28 days), the stents are explanted, and assayed.

Devices comprising stents having coatings disclosed herein alternatively are implanted in the common iliac arteries of New Zealand white rabbits. The stents are expanded to a 1:1.1 balloon:artery ratio. At multiple time points, animals are euthanized (e.g., t=1 day, 7 days, 14 days, 21 days, and 28 days), the stents are explanted, and assayed.

Example 1

This example illustrates embodiments that provide a coated coronary stent, comprising: a stent framework and an ECM-polymer coating wherein the ECM-polymer coating comprises one or more resorbable polymers. The ECM is in active form in this example.

In these experiments two different polymers are employed:
Polymer A: ~50:50 PLGA-Ester End Group, MW ~19 kD, degradation rate ~1-2 months
Polymer B: ~50:50 PLGA-Carboxylate End Group, MW ~10 kD, degradation rate ~28 days
Metal stents are coated as follows:
AS1: Polymer A/ECM/Polymer A/ECM/Polymer A
AS2: Polymer A/ECM/Polymer A/ECM/Polymer B
AS1 (B) or AS1 (213): Polymer B/ECM/Polymer B/ECM/Polymer B
AS1b: Polymer A/ECM/Polymer A/ECM/Polymer A
AS2b: Polymer A/ECM/Polymer A/ECM/Polymer B Example 2: Determination of Bioabsorbability/Bioresorbability/Dissolution Rate of a Polymer Coating a Device Gel Permeation Chromatography In-vivo Weight Loss Determination Standard methods known in the art can be applied to determine polymer weight loss, for example gel permeation chromatography and other analytical techniques such as described in Jackson et al., "Characterization of perivascular poly(lactic-co-glycolic acid) films containing paclitaxel" *Int. J. of Pharmaceutics,* 283:97-109 (2004), incorporated in its entirety herein by reference.

For example rabbit in vivo models as described above are euthanized at multiple time points (t=1 day, 2 days, 4 days, 7 days, 14 days, 21 days, 28 days, 35 days n=5 per time point). Alternatively, pig in vivo models as described above are euthanized at multiple time points (t=1 day, 2 days, 4 days, 7 days, 14 days, 21 days, 28 days, 35 days n=5 per time point). The stents are explanted, and dried down at 30° C. under a stream of gas to complete dryness. A stent that has not been implanted in the animal is used as a control for no loss of polymer.

The remaining polymer on the explanted stents is removed using a solubilizing solvent (for example chloroform). The solutions containing the released polymers for each time point are filtered. Subsequent GPC analysis is used for quantification of the amount of polymer remaining in the stent at each explant time point. The system, for example, comprises a Shimadzu LC-10 AD HPLC pump, a Shimadzu RID-6A refractive index detector coupled to a 50A Hewlett Packard PI-Gel column. The polymer components are detected by refractive index detection and the peak areas are used to determine the amount of polymer remaining in the stents at the explant time point. A calibration graph of log molecular weight versus retention time is established for the 50A PI-Gel column using polystyrene standards with molecular weights of 300, 600, 1.4 k, 9 k, 20 k, and 30 k g/mol. The decreases in the polymer peak areas on the subsequent time points of the study are expressed as weight percentages relative to the 0 day stent.

Gel Permeation Chromatography In-Vitro Testing

Gel Permeation Chromatography (GPC) can also be used to quantify the bioabsorbability/bioresorbability, dissolution rate, and/or biodegradability of the polymer coating. The in vitro assay is a degradation test where the concentration and molecular weights of the polymers can be assessed when released from the stents in an aqueous solution that mimics physiological surroundings. See for example, Jackson et al., "Characterization of perivascular poly(lactic-co-glycolic acid) films containing paclitaxel" *Int. J. of Pharmaceutics,* 283:97-109 (2004), incorporated in its entirety herein by reference.

For example Stents (n=15) described herein are expanded and then placed in a solution of 1.5 ml solution of phosphate buffered saline (pH=7.4) with 0.05% wt of Tween20, or in the alternative 10 mM Tris, 0.4 wt. % SDS, pH 7.4, in a 37° C. bath with bath rotation at 70 rpm. Alternatively, a coated coupon could be tested in this method. The solution is then collected at the following time points: 0 min., 15 min., 30 min., 1 hr, 2 hr, 4 hr, 6 hr, 8 hr, 12 hr, 16 hr, 20 hr, 24 hr, 30 hr, 36 hr, 48 hr, and daily up to 70 days, for example. The solution is replaced at least at each time point, and/or periodically (e.g. every four hours, daily, weekly, or longer for later time points) to prevent saturation, the removed solution is collected, saved, and assayed. The solutions containing the released polymers for each time point are filtered to reduce clogging the GPC system. For time points over 4 hours, the multiple collected solutions are pooled together for liquid extraction.

1 ml Chloroform is added to the phosphate buffered saline solutions and shaken to extract the released polymers from the aqueous phase. The chloroform phase is then collected for assay via GPC.

The system comprises a Shimadzu LC-10 AD HPLC pump, a Shimadzu RID-6A refractive index (RI) detector coupled to a 50 Å Hewlett Packard PI-Gel column. The mobile phase is chloroform with a flow rate of 1 mL/min. The injection volume of the polymer sample is 100 μL of a polymer concentration. The samples are run for 20 minutes at an ambient temperature.

For determination of the released polymer concentrations at each time point, quantitative calibration graphs are first made using solutions containing known concentrations of each polymer in chloroform. Stock solutions containing each polymer in 0-5 mg/ml concentration range are first analyzed by GPC and peak areas are used to create separate calibration curves for each polymer.

For polymer degradation studies, a calibration graph of log molecular weight versus retention time is established for a 50 Å PI-Gel column (Hewlett Packard) using polystyrene standards with molecular weights of 300, 600, 1.4 k, 9 k, 20 k, and 30 k g/mol. In the alternative, a Multi angle light scattering (MALS) detector may be fitted to directly assess the molecular weight of the polymers without the need of polystyrene standards.

To perform an accelerated in-vitro dissolution of the bioresorbable polymers, a protocol is adapted from ISO Standard 13781 "Poly(L-lactide) resides and fabricated an accelerated forms for surgical implants—in vitro degradation testing" (1997), incorporated in its entirety herein by reference. Briefly, elution buffer comprising 18% v/v of a stock solution of 0.067 mol/L $KH_2PO_4$ and 82% v/v of a stock solution of 0.067 mol/L $Na_2HPO_4$ with a pH of 7.4 is used. Stents described herein are expanded and then placed in 1.5 ml solution of this accelerated buffer in a 70° C. bath with rotation at 70 rpm. The solutions are then collected at the following time points: 0 min., 15 min., 30 min., 1 hr, 2 hr, 4 hr, 6 hr, 8 hr, 12 hr, 16 hr, 20 hr, 24 hr, 30 hr, 36 hr and 48 hr. Fresh accelerated elution buffer are added periodically every two hours to replace the incubated buffers that are collected and saved in order to prevent saturation. The solutions containing the released polymers for each time point are filtered to reduce clogging the GPC system. For time points over 2 hours, the multiple collected solutions are pooled together for liquid extraction by chloroform. Chloroform extraction and GPC analysis is performed in the manner described above.

Scanning Electron Microscopy (SEM) with Focused Ion Beam (FIB) Milling In-Vitro Testing Focused ion beam FIB is a tool that allows precise site-specific sectioning, milling and depositing of materials. FIB can be used in conjunction with SEM, at ambient or cryo conditions, to produce in-situ sectioning followed by high-resolution imaging. FIB-SEM can produce a cross-sectional image of the polymer layers on the stent. The image can be used to quantitate the thickness of the layers to reveal rate of bioresorbability of single or multiple polymers as well as show whether there is uniformity of the layer thickness at manufacture and at time points after stenting (or after in-vitro elution at various time points).

For example, testing is performed at multiple time points. Stents are removed from the elution media and dried, the dried stent is visualized using FIB-SEM for changes in the coating. Alternatively, a coated coupon or other substrate could be tested in this method.

Stents (n=15) described herein are expanded and then placed in 1.5 ml solution of phosphate buffered saline (pH=7.4) with 0.05% wt of Tween20 in a 37° C. bath with bath rotation at 70 rpm. Alternatively, a coated coupon could be tested in this method. The phosphate buffered saline solution is periodically replaced with fresh solution at each time point and/or every four hours to prevent saturation. The stents are collected at the following time points: 30 min, 1 hr, 2 hr, 4 hr, 6 hr, 8, hr, 12 hr, 16 hr, 20 hr, 24 hr, 30 hr, 36 hr, 48 hr, 60 h and 72 h. The stents are dried down at 30° C. under a stream of gas to complete dryness. A stent that not been subjected to these conditions is used as a t=0 control.

A FEI Dual Beam Strata 235 FIB/SEM system is a combination of a finely focused Ga ion beam (FIB) accelerated by 30 kV with a field emission electron beam in a scanning electron microscope instrument and is used for imaging and sectioning the stents. Both beams focus at the same point of the sample with a probe diameter less than 10 nm. The FIB can also produce thinned down sections for TEM analysis.

To prevent damaging the surface of the stent with incident ions, a Pt coating is first deposited via electron beam assisted deposition and ion beam deposition prior to FIB sectioning. For FIB sectioning, the Ga ion beam is accelerated to 30 kV and the sectioning process is about 2 h in duration. Completion of the FIB sectioning allows one to observe and quantify by SEM the thickness of the polymer layers that are left on the stent as they are absorbed.

Raman Spectroscopy In-Vitro Testing

Raman spectroscopy can be applied to characterize the chemical structure and relative concentrations of active agent and polymer coatings. This can also be applied to characterize in-vitro tested polymer coatings on stents or other substrates.

For example, confocal Raman Spectroscopy/microscopy can be used to characterize the relative active agent to polymer ratio at the outer ~1 μm of the coated surface as a function of time exposed to elution media. In addition confocal Raman x-z or z (maps or line scans) microscopy can be applied to characterize the relative active agent to polymer ratio as a function of depth at time t after exposure to elution media.

For example a sample (a coated stent) is prepared as described herein and placed in elution media (e.g., 10 mM tris(hydroxymethyl)aminomethane (Tris), 0.4 wt. % Sodium dodecyl sulphate (SDS), pH 7.4 or 1.5 ml solution of phosphate buffered saline (pH=7.4) with 0.05% wt of Tween20) in a 37° C. bath with bath rotation at 70 rpm. Confocal Raman Images are taken on the coating before elution. At least four elution time points within a 48 day interval, (e.g. 0 min., 15 min., 30 min., 1 hr, 2 hr, 4 hr, 6 hr, 8, hr, 12 hr, 16 hr, 20 hr, 24 hr, 30 hr, 36 hr and 48 hr) the sample is removed from the elution, and dried (for example, in a stream of nitrogen). The dried stent is visualized using Raman Spectroscopy for changes in coating. Alternatively, a coated coupon could be tested in this method. After analysis, each is returned to the buffer for further elution.

Raman spectroscopy and other analytical techniques such as described in Balss, et al., "Quantitative spatial distribution of sirolimus and polymers in drug-eluting stents using confocal Raman microscopy" *J. of Biomedical Materials Research Part A*, 258-270 (2007), incorporated in its entirety herein by reference, and/or described in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

For example a WITec CRM 200 scanning confocal Raman microscope using a Nd:YAG laser at 532 nm is applied in the Raman imaging mode to generate an x-z map. The sample is placed upon a piezoelectrically driven table, the laser light is focused upon the sample using a 100× dry objective (numerical aperture 0.90), and the finely focused laser spot is scanned into the sample. As the laser scans the sample, over each 0.33 micron interval a Raman spectrum with high signal to noise is collected using 0.3 Seconds of integration time. Each confocal cross-sectional image of the coatings displays a region 70 µm wide by 10 µm deep, and results from the gathering of 6300 spectra with a total imaging time of 32 min.

SEM-In-Vitro Testing

Testing is performed at multiple time points (e.g. 0 min., 15 min., 30 min., 1 hr, 2 hr, 4 hr, 6 hr, 8, hr, 12 hr, 16 hr, 20 hr, 24 hr, 30 hr, 36 hr and 48 hr). Stents are removed from the elution media (described supra) and dried at these time points. The dried stent is visualized using SEM for changes in coating.

For example the samples are observed by SEM using a Hitachi S-4800 with an accelerating voltage of 800V. Various magnifications are used to evaluate the coating integrity, especially at high strain regions. Change in coating over time is evaluated to visualize the bioabsorption of the polymer over time.

X-ray photoelectron spectroscopy (XPS)—In-Vitro Testing

XPS can be used to quantitatively determine elemental species and chemical bonding environments at the outer 5-10 nm of sample surface. The technique can be operated in spectroscopy or imaging mode. When combined with a sputtering source, XPS can be utilized to give depth profiling chemical characterization.

XPS testing can be used to characterize the active agent to polymer ratio at the very surface of the coating of a sample. Additionally XPS testing can be run in time lapse to detect changes in composition. Thus, in one test, samples are tested using XPS at multiple time points (e.g. 0 min., 15 min., 30 min., 1 hr, 2 hr, 4 hr, 6 hr, 8, hr, 12 hr, 16 hr, 20 hr, 24 hr, 30 hr, 36 hr and 48 hr). Stents are removed from the elution media (e.g., 10 mM Tris, 0.4 wt. % SDS, pH 7.4 or 1.5 ml solution of phosphate buffered saline (pH=7.4) with 0.05% wt of Tween20) in a 37° C. bath with rotation at 70 rpm and dried at these time points.

XPS (ESCA) and other analytical techniques such as described in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

For example, XPS analysis is performed using a Physical Electronics Quantum 2000 Scanning ESCA. The monochromatic Al Kα source is operated at 15 kV with a power of 4.5 W. The analysis is performed at a 45° take off angle. Three measurements are taken along the length of each stent with the analysis area—20 microns in diameter. Low energy electron and Ar$^+$ ion floods are used for charge compensation.

Time of Flight Secondary Ion Mass Spectrometry (TOF-SIMS)

TOF-SIMS can be used to determine molecular species at the outer 1-2 nm of sample surface when operated under static conditions. The technique can be operated in spectroscopy or imaging mode at high spatial resolution. When operated under dynamic experimental conditions, known in the art, depth profiling chemical characterization can be achieved.

TOF-SIMS testing can be used to characterize the presence of polymer and or active agent at uppermost surface of the coating of a sample. Additionally TOF-SIMS testing can be run in time lapse to detect changes in composition. Thus, in one test, samples are tested using TOF-SIMS at multiple time points (e.g., 0 min., 15 min., 30 min., 1 hr, 2 hr, 4 hr, 6 hr, 8, hr, 12 hr, 16 hr, 20 hr, 24 hr, 30 hr, 36 hr and 48 hr). Stents are removed from the elution media (e.g. 10 mM Tris, 0.4 wt. % SDS, pH 7.4 or 1.5 ml solution of phosphate buffered saline (pH=7.4) with 0.05% wt of Tween20) in a 37° C. bath with rotation at 70 rpm and dried at these time points.

For example, to analyze the uppermost surface only, static conditions (for example a ToF-SIMS IV (IonToF, Munster)) using a 25 Kv Bi$^{++}$ primary ion source maintained below $10^{12}$ ions per cm$^2$ is used. Where necessary a low energy electron flood gun (0.6 nA DC) is used to charge compensate insulating samples.

Cluster Secondary Ion Mass Spectrometry, may be employed for depth profiling as described Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference.

For example, a stent as described herein is obtained. The stent is prepared for SIMS analysis by cutting it longitudinally and opening it up with tweezers. The stent is then pressed into multiple layers of indium foil with the outer diameter facing outward.

TOF-SIMS depth profiling experiments are performed using an Ion-TOF IV instrument equipped with both Bi and SF5+ primary ion beam cluster sources. Sputter depth profiling is performed in the dual-beam mode, while preserving the chemical integrity of the sample. For example, the analysis source is a pulsed, 25-keV bismuth cluster ion source, which bombarded the surface at an incident angle of 45° to the surface normal. The target current is maintained at ~0.3 pA (+10%) pulsed current with a raster size of 200 micron×200 micron for all experiments. Both positive and negative secondary ions are extracted from the sample into a reflectron-type time-of-flight mass spectrometer. The secondary ions are then detected by a microchannel plate detector with a post-acceleration energy of 10 kV. A low-energy electron flood gun is utilized for charge neutralization in the analysis mode.

The sputter source used is a 5-keV SF5+ cluster source also operated at an incident angle of 45° to the surface normal. For thin model samples on Si, the SF5+ current is maintained at ~2.7 nA with a 750 micron×750 micron raster. For the thick samples on coupons and for the samples on stents, the current is maintained at 6 nA with a 500 micron× 500 micron raster. All primary beam currents are measured with a Faraday cup both prior to and after depth profiling.

All depth profiles are acquired in the noninterlaced mode with a 5-ms pause between sputtering and analysis. Each spectrum is averaged over a 7.37 second time period. The analysis is immediately followed by 15 seconds of $SF_5^+$ sputtering. For depth profiles of the surface and subsurface regions only, the sputtering time was decreased to 1 second for the 5% active agent sample and 2 seconds for both the 25% and 50% active agent samples.

Temperature-controlled depth profiles are obtained using a variable-temperature stage with Eurotherm Controls temperature controller and IPSG V3.08 software. Samples are first placed into the analysis chamber at room temperature. The samples are brought to the desired temperature under ultra high-vacuum conditions and are allowed to stabilize for 1 minute prior to analysis. All depth profiling experiments are performed at −100° C. and 25° C.

Infrared (IR) Spectroscopy for In-Vitro Testing

Infrared (IR) Spectroscopy such as, but not limited to, FTIR, ATR-IR and micro ATR-IR are well utilized techniques that can be applied to show the quantitative polymer content in the coating, and the distribution of polymer in the coating.

For example using FTIR, a coupon of crystalline ZnSe is coated by the processes described herein, creating a PAPAP (Polymer, Active agent, Polymer, Active agent, Polymer) layered coating that is about 10 microns thick. At time=0 and at least four elution time points within a 48 day interval (e.g., 0 min., 15 min., 30 min., 1 hr, 2 hr, 4 hr, 6 hr, 8, hr, 12 hr, 16 hr, 20 hr, 24 hr, 30 hr, 36 hr and 48 hr), the sample (coated crystal) is tested by FTIR for polymer content. The sample is placed in an elution media (e.g. 10 mM Tris, 0.4 wt. % SDS, pH 7.4 or 1.5 ml solution of phosphate buffered saline (pH=7.4) with 0.05% wt of Tween20) in a 37° C. bath with bath rotation at 70 rpm and at each time point, the sample is removed from the elution media and dried (e.g. in a stream of nitrogen). FTIR spectrometry is used to quantify the polymer on the sample. After analysis, each is returned to the buffer for further elution.

In another example using FTIR, sample elution media at each time point is tested for polymer content. In this example, a coated stent was prepared that was coated by the processes described herein, creating a PAPAP (Polymer, Active agent, Polymer, Active agent, Polymer) layered coating that is about 10 microns thick. The coated stent is placed in an elution media (e.g. 10 mM Tris, 0.4 wt. % SDS, pH 7.4 or 1.5 ml solution of phosphate buffered saline (pH=7.4) with 0.05% wt of Tween20) in a 37° C. bath with rotation at 70 rpm. and at each time point (e.g., 0 min., 15 min., 30 min., 1 hr, 2 hr, 4 hr, 6 hr, 8, hr, 12 hr, 16 hr, 20 hr, 24 hr, 30 hr, 36 hr and 48 hr), a sample of the elution media is removed and dried onto a crystalline ZnSe window (e.g. in a stream of nitrogen). At each elution time point, the sample elution media is tested by FTIR for polymer content.

Atomic Force Microscopy (AFM)

AFM is a high resolution surface characterization technique. AFM is used in the art to provide topographical imaging, in addition when employed in Tapping Mode™ can image material and or chemical properties of the surface. The technique can be used under ambient, solution, humidified or temperature controlled conditions. Other modes of operation are well known and can be readily employed here by those skilled in the art. The AFM topography images can be run in time-lapse to characterize the surface as a function of elution time. Three-dimensionally rendered images show the surface of a coated stent, which can show holes or voids of the coating which may occur as the polymer is absorbed and the active agent is eluted over time.

A stent as described herein is obtained. AFM is used to determine the active agent polymer distribution. AFM may be employed as described in Ranade et al., "Physical characterization of controlled release of paclitaxel from the TAXUS Express2 drug-eluting stent" *J. Biomed. Mater. Res.* 71(4):625-634 (2004) incorporated herein in its entirety by reference.

For example a multi-mode AFM (Digital Instruments/Veeco Metrology, Santa Barbara, Calif.) controlled with Nanoscope IIIa and NanoScope Extender electronics is used. Samples are examined in the dry state using AFM before elution of the active agent. Samples are also examined at select time points through an elution period (e.g. 48 hours) by using an AFM probe-tip and flow-through stage built to permit analysis of wet samples. The wet samples are examined in the presence of the same elution medium used for in-vitro kinetic active agent release analysis (e.g. PBS-Tween20, or 10 mM Tris, 0.4 wt. % SDS, pH 7.4). Saturation of the solution is prevented by frequent exchanges of the release medium with several volumes of fresh medium. TappingMode™ AFM imaging may be used to show topography (a real-space projection of the coating surface microstructure) and phase-angle changes of the AFM over the sample area to contrast differences in the material and physical structure.

Nano X-Ray Computer Tomography

Another technique that may be used to view the physical structure of a device in 3-D is Nano X-Ray Computer Tomography (e.g. such as made by SkyScan), which could be used in an elution test and/or bioabsorbability test, as described herein to show the physical structure of the coating remaining on stents at each time point, as compared to a scan prior to elution/bioabsorption.

pH Testing

The bioabsorbability of PLGA of a coated stent can be shown by testing the pH of an elution media (EtOH/PBS, for example) in which the coated stent is placed. Over time, a bioabsorbable PLGA coated stent (with or without the active agent) will show a decreased pH until the PLGA is fully bioabsorbed by the elution media.

Example 3: Visualization of Polymer/Active Agent Layers Coating a Device

Raman Spectroscopy

Raman spectroscopy can be applied to characterize the chemical structure and relative concentrations of active agent and polymer coatings. For example, confocal Raman Spectroscopy/microscopy can be used to characterize the relative active agent to polymer ratio at the outer ~1 μm of the coated surface. In addition confocal Raman x-z or z (maps or line scans) microscopy can be applied to characterize the relative active agent to polymer ratio as a function of depth. Additionally cross-sectioned samples can be analysed. Raman spectroscopy and other analytical techniques such as described in Balss, et al., "Quantitative spatial distribution of sirolimus and polymers in drug-eluting stents using confocal Raman microscopy" *J. of Biomedical Materials Research Part A*, 258-270 (2007), incorporated in its entirety herein by reference, and/or described in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

A sample (a coated stent) is prepared as described herein. Images are taken on the coating using Raman Spectroscopy. Alternatively, a coated coupon could be tested in this method. To test a sample using Raman microscopy and in particular confocal Raman microscopy, it is understood that to get appropriate Raman high resolution spectra sufficient acquisition time, laser power, laser wavelength, sample step size and microscope objective need to be optimized.

For example a WITec CRM 200 scanning confocal Raman microscope using a Nd:YAG laser at 532 nm is applied in the Raman imaging mode to give x-z maps. The sample is placed upon a piezoelectrically driven table, the laser light is focused upon the sample using a 100× dry objective (numerical aperture 0.90), and the finely focused laser spot is scanned into the sample. As the laser scans the sample, over each 0.33 micron interval a Raman spectrum with high signal to noise is collected using 0.3 Seconds of integration time. Each confocal cross-sectional image of the coatings displays a region 70 μm wide by 10 μm deep, and results from the gathering of 6300 spectra with a total imaging time of 32 min. Multivariate analysis using reference spectra from samples of active agent and polymer are used to deconvolve the spectral data sets, to provide chemical maps of the distribution.

In another test, spectral depth profiles (x-z maps) of samples are performed with a CRM200 microscope system from WITec Instruments Corporation (Savoy, Ill.). The instrument is equipped with a Nd:YAG frequency doubled laser (532 excitation), a single monochromator (Acton) employing a 600 groove/mm grating and a thermoelectrically cooled 1024 by 128 pixel array CCD camera (Andor Technology). The microscope is equipped with appropriate collection optics that include a holographic laser bandpass rejection filter (Kaiser Optical Systems Inc.) to minimize Rayleigh scatter into the monochromator. The Raman scattered light are collected with a 50 micron optical fiber. Using the "Raman Spectral Imaging" mode of the instrument, spectral images are obtained by scanning the sample in the x, z direction with a piezo driven xyz scan stage and collecting a spectrum at every pixel. Typical integration times are 0.3 s per pixel. The spectral images are 4800 total spectra corresponding to a physical scan dimension of 40 by 20 microns. For presentation of the confocal Raman data, images are generated based on unique properties of the spectra (i.e. integration of a Raman band, band height intensity, or band width). The microscope stage is modified with a custom-built sample holder that positioned and rotated the stents around their primary axis. The x direction is defined as the direction running parallel to the length of the stent and the z direction refers to the direction penetrating through the coating from the air-coating to the coating-metal interface. Typical laser power is <10 mW on the sample stage. All experiments can be conducted with a plan achromat objective, 100×$N_A$=0.9 (Nikon).

Samples (n=5) comprising stents made of L605 (0.05-0.15% C, 1.00-2.00% Mn, maximum 0.040% Si, maximum 0.030% P, maximum 0.3% S, 19.00-21.00% Cr, 9.00-11.00% Ni, 14.00-16.00% W, 3.00% Fe, and Bal. Co) and having coatings as described herein and/or produced by methods described herein can be analyzed. For each sample, three locations are selected along the stent length. The three locations are located within one-third portions of the stents so that the entire length of the stent are represented in the data. The stent is then rotated 180 degrees around the circumference and an additional three locations are sampled along the length. In each case, the data is collected from the strut portion of the stent. Six random spatial locations are also profiled on coated coupon samples made of L605 and having coatings as described herein and/or produced by methods described herein. The Raman spectra of each individual component present in the coatings are also collected for comparison and reference. Using the instrument software, the average spectra from the spectral image data are calculated by selecting the spectral image pixels that are exclusive to each layer. The average spectra are then exported into GRAMS/AI v. 7.02 software (Thermo Galactic) and the appropriate Raman bands are fit to a Voigt function. The band areas and shift positions are recorded.

The pure component spectrum for each component of the coating (e.g. active agent, polymer) are also collected at 532 and 785 nm excitation. The 785 nm excitation spectra are collected with a confocal Raman microscope (WITec Instruments Corp. Savoy, Ill.) equipped with a 785 nm diode laser, appropriate collection optics, and a back-illuminated thermoelectrically cooled 1024×128 pixel array CCD camera optimized for visible and infrared wavelengths (Andor Technology).

X-Ray Photoelectron Spectroscopy (XPS)

XPS can be used to quantitatively determine elemental species and chemical bonding environments at the outer 5-10 nm of sample surface. The technique can be operated in spectroscopy or imaging mode. When combined with a sputtering source XPS can be utilized to give depth profiling chemical characterization. XPS (ESCA) and other analytical techniques such as described in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

For example, in one test, a sample comprising a stent coated by methods described herein and/or a device as described herein is obtained. XPS analysis is performed on a sample using a Physical Electronics Quantum 2000 Scanning ESCA. The monochromatic Al Kα source is operated at 15 kV with a power of 4.5 W. The analysis is done at a 45° take off angle. Three measurements are taken along the length of each sample with the analysis area ~20 microns in diameter. Low energy electron and $Ar^+$ ion floods are used for charge compensation.

Time of Flight Secondary Ion Mass Spectrometry (TOF-SIMS)

TOF-SIMS can be used to determine molecular species (active agent and polymer) at the outer 1-2 nm of sample surface when operated under static conditions. The technique can be operated in spectroscopy or imaging mode at high spatial resolution. Additionally cross-sectioned samples can be analysed. When operated under dynamic experimental conditions, known in the art, depth profiling chemical characterization can be achieved.

For example, to analyze the uppermost surface only, static conditions (for example a ToF-SIMS IV (IonToF, Munster)) using a 25 Kv $Bi^{++}$ primary ion source maintained below $10^{12}$ ions per $cm^2$ is used. Where necessary a low energy electron flood gun (0.6 nA DC) is used to charge compensate insulating samples.

Cluster Secondary Ion Mass Spectrometry, may be employed for depth profiling as described Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference.

For example, a stent as described herein is obtained. The stent is prepared for SIMS analysis by cutting it longitudinally and opening it up with tweezers. The stent is then pressed into multiple layers of indium foil with the outer diameter facing outward.

TOF-SIMS depth profiling experiments are performed using an Ion-TOF IV instrument equipped with both Bi and SF5+ primary ion beam cluster sources. Sputter depth profiling is performed in the dual-beam mode, whilst preserving the chemical integrity of the sample. The analysis source is a pulsed, 25-keV bismuth cluster ion source, which bombarded the surface at an incident angle of 45° to the surface normal. The target current is maintained at ~0.3 pA (+10%) pulsed current with a raster size of 200 um×200 um for all experiments. Both positive and negative secondary ions are extracted from the sample into a reflectron-type time-of-flight mass spectrometer. The secondary ions are then detected by a microchannel plate detector with a post-acceleration energy of 10 kV. A low-energy electron flood gun is utilized for charge neutralization in the analysis mode.

The sputter source used is a 5-keV SF5+ cluster source also operated at an incident angle of 45° to the surface normal. For thin model samples on Si, the SF5+ current is maintained at ~2.7 nA with a 750 um×750 um raster. For the thick samples on coupons and for the samples on stents, the current is maintained at 6 nA with a 500 um×500 um raster. All primary beam currents are measured with a Faraday cup both prior to and after depth profiling.

All depth profiles are acquired in the noninterlaced mode with a 5-ms pause between sputtering and analysis. Each spectrum is averaged over a 7.37 second time period. The analysis is immediately followed by 15 seconds of $SF_5^+$ sputtering. For depth profiles of the surface and subsurface regions only, the sputtering time was decreased to 1 second for the 5% active agent sample and 2 seconds for both the 25% and 50% active agent samples.

Temperature-controlled depth profiles are obtained using a variable-temperature stage with Eurotherm Controls temperature controller and IPSG V3.08 software. Samples are first placed into the analysis chamber at room temperature. The samples are brought to the desired temperature under ultra high-vacuum conditions and are allowed to stabilize for 1 minute prior to analysis. All depth profiling experiments are performed at −100 C and 25 C.

Atomic Force Microscopy (AFM)

AFM is a high resolution surface characterization technique. AFM is used in the art to provide topographical imaging, in addition when employed in Tapping Mode™ can image material and or chemical properties of the surface. Additionally cross-sectioned samples can be analyzed. The technique can be used under ambient, solution, humidified or temperature controlled conditions. Other modes of operation are well known and can be readily employed here by those skilled in the art.

A stent as described herein is obtained. AFM is used to determine the structure of the active agent polymer layers. AFM may be employed as described in Ranade et al., "Physical characterization of controlled release of paclitaxel from the TAXUS Express2 drug-eluting stent" *J. Biomed. Mater. Res.* 71(4):625-634 (2004) incorporated herein in its entirety by reference.

Polymer and active agent morphologies, coating composition, at least may be determined using atomic force microscopy (AFM) analysis. A multi-mode AFM (Digital Instruments/Veeco Metrology, Santa Barbara, Calif.) controlled with Nanoscope Ma and NanoScope Extender electronics is used. Samples are examined in the dry state using AFM before elution of the active agent. Samples are also examined at select time points through a elution period (e.g. 48 hours) by using an AFM probe-tip and flow-through stage built to permit analysis of wet samples. The wet samples are examined in the presence of the same elution medium used for in-vitro kinetic drug release analysis (e.g. PBS-Tween20, or 10 mM Tris, 0.4 wt. % SDS, pH 7.4). Saturation of the solution is prevented by frequent exchanges of the release medium with several volumes of fresh medium. Tapping-Mode™ AFM imaging may be used to show topography (a real-space projection of the coating surface microstructure) and phase-angle changes of the AFM over the sample area to contrast differences in the materials properties. The AFM topography images can be three-dimensionally rendered to show the surface of a coated stent, which can show holes or voids of the coating which may occur as the polymer is absorbed and the drug is eluted over time, for example.

Scanning Electron Microscopy (SEM) with Focused Ion Beam (FIB) Milling

Stents as described herein, and or produced by methods described herein are visualized using SEM-FIB. Alternatively, a coated coupon could be tested in this method. Focused ion beam FIB is a tool that allows precise site-specific sectioning, milling and depositing of materials. FIB can be used in conjunction with SEM, at ambient or cryo conditions, to produce in-situ sectioning followed by high-resolution imaging. FIB-SEM can produce a cross-sectional image of the polymer and active agent layers on the stent. The image can be used to quantitate the thickness of the layers and uniformity of the layer thickness at manufacture and at time points after stenting (or after in-vitro elution at various time points).

A FEI Dual Beam Strata 235 FIB/SEM system is a combination of a finely focused Ga ion beam (FIB) accelerated by 30 kV with a field emission electron beam in a scanning electron microscope instrument and is used for imaging and sectioning the stents. Both beams focus at the same point of the sample with a probe diameter less than 10 nm The FIB can also produce thinned down sections for TEM analysis.

To prevent damaging the surface of the stent with incident ions, a Pt coating is first deposited via electron beam assisted deposition and ion beam deposition prior to FIB sectioning. For FIB sectioning, the Ga ion beam is accelerated to 30 kV and the sectioning process is about 2 h in duration. Completion of the FIB sectioning allows one to observe and quantify by SEM the thickness of the polymer layers that are, for example, left on the stent as they are absorbed.

Example 4: Analysis of the Thickness of a Device Coating

Analysis can be determined by either in-situ analysis or from cross-sectioned samples.

X-Ray Photoelectron Spectroscopy (XPS)

XPS can be used to quantitatively determine the presence of elemental species and chemical bonding environments at the outer 5-10 nm of sample surface. The technique can be operated in spectroscopy or imaging mode. When combined with a sputtering source XPS can be utilized to give depth profiling chemical characterization. XPS (ESCA) and other analytical techniques such as described in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

Thus, in one test, a sample comprising a stent coated by methods described herein and/or a device as described herein is obtained. XPS analysis is done on a sample using a Physical Electronics Quantum 2000 Scanning ESCA. The monochromatic Al Kα source is operated at 15 kV with a power of 4.5 W. The analysis is done at a 45° take off angle. Three measurements are taken along the length of each sample with the analysis area ~20 microns in diameter. Low energy electron and $Ar^+$ ion floods are used for charge compensation.

Time of Flight Secondary Ion Mass Spectrometry

TOF-SIMS can be used to determine molecular species (active agent and polymer) at the outer 1-2 nm of sample surface when operated under static conditions. The technique can be operated in spectroscopy or imaging mode at high spatial resolution. Additionally cross-sectioned samples can be analysed. When operated under dynamic experimental conditions, known in the art, depth profiling chemical characterization can be achieved.

For example, under static conditions (for example a ToF-SIMS IV (IonToF, Munster)) using a 25 Kv $Bi^{++}$ primary ion source maintained below $10^{12}$ ions per $cm^2$ is used. Where necessary a low energy electron flood gun (0.6 nA DC) is used to charge compensate insulating samples.

Cluster Secondary Ion Mass Spectrometry, may be employed for depth profiling as described Belu et al., "Three-Dimensional Compositional Analysis of Drug Eluting Stent Coatings Using Cluster Secondary Ion Mass Spectroscopy" Anal. Chem. 80: 624-632 (2008) incorporated herein in its entirety by reference.

A stent as described herein is obtained. The stent is prepared for SIMS analysis by cutting it longitudinally and opening it up with tweezers. The stent is then pressed into multiple layers of iridium foil with the outer diameter facing outward.

TOF-SIMS experiments are performed on an Ion-TOF IV instrument equipped with both Bi and SF5+ primary ion beam cluster sources. Sputter depth profiling is performed in the dual-beam mode. The analysis source is a pulsed, 25-keV bismuth cluster ion source, which bombarded the surface at an incident angle of 45° to the surface normal. The target current is maintained at ~0.3 pÅ (+10%) pulsed current with a raster size of 200 um×200 um for all experiments. Both positive and negative secondary ions are extracted from the sample into a reflectron-type time-of-flight mass spectrometer. The secondary ions are then detected by a microchannel plate detector with a post-acceleration energy of 10 kV. A low-energy electron flood gun is utilized for charge neutralization in the analysis mode.

The sputter source used is a 5-keV SF5+ cluster source also operated at an incident angle of 45° to the surface normal. For thin model samples on Si, the SF5+ current is maintained at ~2.7 nA with a 750 um×750 um raster. For the thick samples on coupons and for the samples on stents, the current is maintained at 6 nA with a 500 um×500 um raster. All primary beam currents are measured with a Faraday cup both prior to and after depth profiling.

All depth profiles are acquired in the noninterlaced mode with a 5-ms pause between sputtering and analysis. Each spectrum is averaged over a 7.37 second time period. The analysis is immediately followed by 15 seconds of $SF_5^+$ sputtering. For depth profiles of the surface and subsurface regions only, the sputtering time was decreased to 1 second for the 5% active agent sample and 2 seconds for both the 25% and 50% active agent samples.

Temperature-controlled depth profiles are obtained using a variable-temperature stage with Eurotherm Controls temperature controller and IPSG V3.08 software. Samples are first placed into the analysis chamber at room temperature. The samples are brought to the desired temperature under ultra high-vacuum conditions and are allowed to stabilize for 1 minute prior to analysis. All depth profiling experiments are performed at −100° C. and 25° C.

Atomic Force Microscopy (AFM)

AFM is a high resolution surface characterization technique. AFM is used in the art to provide topographical imaging, in addition when employed in Tapping Mode™ can image material and or chemical properties of the surface. Additionally cross-sectioned samples can be analyzed.

A stent as described herein is obtained. AFM may be alternatively employed as described in Ranade et al., "Physical characterization of controlled release of paclitaxel from the TAXUS Express2 drug-eluting stent" J. Biomed. Mater. Res. 71(4):625-634 (2004) incorporated herein in its entirety by reference.

Polymer and active agent morphologies, coating composition, and cross-sectional thickness at least may be determined using atomic force microscopy (AFM) analysis. A multi-mode AFM (Digital Instruments/Veeco Metrology, Santa Barbara, Calif.) controlled with Nanoscope Ma and NanoScope Extender electronics is used TappingMode™ AFM imaging may be used to show topography (a real-space projection of the coating surface microstructure) and phase-angle changes of the AFM over the sample area to contrast differences in the materials properties. The AFM topography images can be three-dimensionally rendered to show the surface of a coated stent or cross-section.

Scanning Electron Microscopy (SEM) with Focused Ion Beam (FIB)

Stents as described herein, and/or produced by methods described herein, are visualized using SEM-FIB analysis. Alternatively, a coated coupon or other coated substrate could be tested in this method. Focused ion beam FIB is a tool that allows precise site-specific sectioning, milling and depositing of materials. FIB can be used in conjunction with SEM, at ambient or cryo conditions, to produce in-situ sectioning followed by high-resolution imaging. FIB-SEM can produce a cross-sectional image of the polymer layers on the stent. The image can be used to quantitate the thickness of the layers as well as show whether there is uniformity of the layer thickness at manufacture and at time points after stenting (or after in-vitro elution at various time points).

A FEI Dual Beam Strata 235 FIB/SEM system is a combination of a finely focused Ga ion beam (FIB) accelerated by 30 kV with a field emission electron beam in a scanning electron microscope instrument and is used for imaging and sectioning the stents. Both beams focus at the same point of the sample with a probe diameter less than 10 nm The FIB can also produce thinned down sections for TEM analysis.

To prevent damaging the surface of the stent with incident ions, a Pt coating is first deposited via electron beam assisted deposition and ion beam deposition prior to FIB sectioning. For FIB sectioning, the Ga ion beam is accelerated to 30 kV and the sectioning process is about 2 h in duration. Completion of the FIB sectioning allows one to observe and quantify by SEM the thickness of the polymer layers that are, for example, left on the stent as they are absorbed.

Interferometry

Interferometry may additionally and/or alternatively used to determine the thickness of the coating as noted in Belu et al., "Three-Dimensional Compositional Analysis of Drug Eluting Stent Coatings Using Cluster Secondary Ion Mass Spectroscopy" Anal. Chem. 80: 624-632 (2008) incorporated herein in its entirety by reference may be used.

Ellipsometry

Ellipsometry is sensitive measurement technique for coating analysis on a coupon. It uses polarized light to probe the dielectric properties of a sample. Through an analysis of the state of polarization of the light that is reflected from the sample the technique allows the accurate characterization of the layer thickness and uniformity. Thickness determinations ranging from a few angstroms to tens of microns are possible for single layers or multilayer systems. See, for example, Jewell, et al., "Release of Plasmid DNA from Intravascular Stents Coated with Ultrathin Multilayered Polyelectrolyte Films" *Biomacromolecules.* 7: 2483-2491 (2006) incorporated herein in its entirety by reference.

Example 5: Analysis of the Thickness of a Device

Scanning Electron Microscopy (SEM)

A sample coated stent described herein is obtained. Thickness of the device can be assessed using this analytical technique. The thickness of multiple locations on the stent or other substrate may be taken to ensure reproducibility and to characterize the coating and stent. The thickness of the coating may be observed by SEM using a Hitachi S-4800 with an accelerating voltage of 800V. Various magnifications are used. SEM can provide top-down and cross-section images at various magnifications.

Nano X-Ray Computer Tomography

Another technique that may be used to view the physical structure of a device in 3-D is Nano X-Ray Computer Tomography (e.g. such as made by SkyScan).

Example 6: Determination of the Type or Composition of a Polymer Coating a Device Nuclear Magnetic Resonance (NMR)

Composition of the polymer samples before and after elution can be determined by $^1$H NMR spectrometry as described in Xu et al., "Biodegradation of poly(l-lactide-co-glycolide tube stents in bile" *Polymer Degradation and Stability.* 93:811-817 (2008) incorporated herein in its entirety by reference. Compositions of polymer samples are determined for example using a 300M Bruker spectrometer with d-chloroform as solvent at room temperature.

Raman Spectroscopy

FT-Raman or confocal raman microscopy can be employed to determine composition.

For example, a sample (a coated stent) is prepared as described herein. Images are taken on the coating using Raman Spectroscopy. Alternatively, a coated coupon could be tested in this method. To test a sample using Raman microscopy and in particular confocal Raman microscopy, it is understood that to get appropriate Raman high resolution spectra sufficient acquisition time, laser power, laser wavelength, sample step size and microscope objective need to be optimized Raman spectroscopy and other analytical techniques such as described in Balss, et al., "Quantitative spatial distribution of sirolimus and polymers in drug-eluting stents using confocal Raman microscopy" *J. of Biomedical Materials Research Part A,* 258-270 (2007), incorporated in its entirety herein by reference, and/or described in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

For example a WITec CRM 200 scanning confocal Raman microscope using a Nd:YAG laser at 532 nm is applied in the Raman imaging mode. The sample is placed upon a piezoelectrically driven table, the laser light is focused upon the sample using a 100× dry objective (numerical aperture 0.90), and the finely focused laser spot is scanned into the sample. As the laser scans the sample, over each 0.33 micron interval a Raman spectrum with high signal to noise is collected using 0.3 Seconds of integration time. Each confocal cross-sectional image of the coatings displays a region 70 µm wide by 10 um deep, and results from the gathering of 6300 spectra with a total imaging time of 32 min. Multivariate analysis using reference spectra from samples of the active agent (in active or inactive form) and polymer references are used to deconvolve the spectral data sets, to provide chemical maps of the distribution.

In another test, spectral depth profiles of samples are performed with a CRM200 microscope system from WITec Instruments Corporation (Savoy, Ill.). The instrument is equipped with a NdYAG frequency doubled laser (532 excitation), a single monochromator (Acton) employing a 600 groove/mm grating and a thermoelectrically cooled 1024 by 128 pixel array CCD camera (Andor Technology). The microscope is equipped with appropriate collection optics that include a holographic laser bandpass rejection filter (Kaiser Optical Systems Inc.) to minimize Rayleigh scatter into the monochromator. The Raman scattered light are collected with a 50 micron optical fiber. Using the "Raman Spectral Imaging" mode of the instrument, spectral images are obtained by scanning the sample in the x, z direction with a piezo driven xyz scan stage and collecting a spectrum at every pixel. Typical integration times are 0.3 s per pixel. The spectral images are 4800 total spectra corresponding to a physical scan dimension of 40 by 20 microns. For presentation of the confocal Raman data, images are generated based on unique properties of the spectra (i.e. integration of a Raman band, band height intensity, or band width). The microscope stage is modified with a custom-built sample holder that positioned and rotated the stents around their primary axis. The x direction is defined as the direction running parallel to the length of the stent and the z direction refers to the direction penetrating through the coating from the air-coating to the coating-metal interface. Typical laser power is <10 mW on the sample stage. All experiments can be conducted with a plan achromat objective, 100×$N_A$=0.9 (Nikon).

Samples (n=5) comprising stents made of L605 and having coatings as described herein and/or produced by methods described herein can be analyzed. For each sample, three locations are selected along the stent length. The three locations are located within one-third portions of the stents so that the entire length of the stent are represented in the data. The stent is then rotated 180 degrees around the circumference and an additional three locations are sampled along the length. In each case, the data is collected from the strut portion of the stent. Six random spatial locations are also profiled on coated coupon samples made of L605 and having coatings as described herein and/or produced by methods described herein. The Raman spectra of each individual component present in the coatings are also collected for comparison and reference. Using the instrument software, the average spectra from the spectral image data are calculated by selecting the spectral image pixels that are exclusive to each layer. The average spectra are then exported into GRAMS/AI v. 7.02 software (Thermo Galactic) and the appropriate Raman bands are fit to a Voigt function. The band areas and shift positions are recorded.

The pure component spectrum for each component of the coating (e.g. active agent, polymer) are also collected at 532 and 785 nm excitation. The 785 nm excitation spectra are collected with a confocal Raman microscope (WITec Instruments Corp. Savoy, Ill.) equipped with a 785 nm diode laser, appropriate collection optics, and a back-illuminated thermoelectrically cooled 1024×128 pixel array CCD camera optimized for visible and infrared wavelengths (Andor Technology).

Time of Flight Secondary Ion Mass Spectrometry

TOF-SIMS can be used to determine molecular species (active agent and polymer) at the outer 1-2 nm of sample surface when operated under static conditions. The technique can be operated in spectroscopy or imaging mode at high spatial resolution. Additionally cross-sectioned samples can be analysed. When operated under dynamic experimental conditions, known in the art, depth profiling chemical characterization can be achieved.

For example, under static conditions (for example a ToF-SIMS IV (IonToF, Munster)) using a 25 Kv $Bi^{++}$ primary ion source maintained below $10^{12}$ ions per $cm^2$ is used. Where necessary a low energy electron flood gun (0.6 nA DC) is used to charge compensate insulating samples.

Cluster Secondary Ion Mass Spectrometry, may be employed as described Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference.

A stent as described herein is obtained. The stent is prepared for SIMS analysis by cutting it longitudinally and opening it up with tweezers. The stent is then pressed into multiple layers of iridium foil with the outer diameter facing outward.

TOF-SIMS experiments are performed on an Ion-TOF IV instrument equipped with both Bi and SF5+ primary ion beam cluster sources. Sputter depth profiling is performed in the dual-beam mode. The analysis source is a pulsed, 25-keV bismuth cluster ion source, which bombarded the surface at an incident angle of 45° to the surface normal. The target current is maintained at ~0.3 pÅ (+10%) pulsed current with a raster size of 200 um×200 um for all experiments. Both positive and negative secondary ions are extracted from the sample into a reflectron-type time-of-flight mass spectrometer. The secondary ions are then detected by a microchannel plate detector with a post-acceleration energy of 10 kV. A low-energy electron flood gun is utilized for charge neutralization in the analysis mode.

The sputter source used is a 5-keV SF5+ cluster source also operated at an incident angle of 45° to the surface normal. For thin model samples on Si, the SF5+ current is maintained at ~2.7 nA with a 750 um×750 um raster. For the thick samples on coupons and for the samples on stents, the current is maintained at 6 nA with a 500 um×500 um raster. All primary beam currents are measured with a Faraday cup both prior to and after depth profiling.

All depth profiles are acquired in the noninterlaced mode with a 5-ms pause between sputtering and analysis. Each spectrum is averaged over a 7.37 second time period. The analysis is immediately followed by 15 seconds of $SF_5^+$ sputtering. For depth profiles of the surface and subsurface regions only, the sputtering time was decreased to 1 second for the 5% active agent sample and 2 seconds for both the 25% and 50% active agent samples.

Temperature-controlled depth profiles are obtained using a variable-temperature stage with Eurotherm Controls temperature controller and IPSG V3.08 software. Samples are first placed into the analysis chamber at room temperature. The samples are brought to the desired temperature under ultra high-vacuum conditions and are allowed to stabilize for 1 minute prior to analysis. All depth profiling experiments are performed at −100 C and 25 C.

Atomic Force Microscopy (AFM)

AFM is a high resolution surface characterization technique. AFM is used in the art to provide topographical imaging, in addition when employed in Tapping Mode™ can image material and or chemical properties of the surface. Additionally cross-sectioned samples can be analyzed. Coating composition may be determined using Tapping Mode™ atomic force microscopy (AFM) analysis. Other modes of operation are well known and can be employed here by those skilled in the art.

A stent as described herein is obtained. AFM may be employed as described in Ranade et al., "Physical characterization of controlled release of paclitaxel from the TAXUS Express2 drug-eluting stent" *J. Biomed. Mater. Res.* 71(4):625-634 (2004) incorporated herein in its entirety by reference.

Polymer and active agent morphologies, coating composition, at least may be determined using atomic force microscopy (AFM) analysis. A multi-mode AFM (Digital Instruments/Veeco Metrology, Santa Barbara, Calif.) controlled with Nanoscope Ma and NanoScope Extender electronics is used. TappingMode™ AFM imaging may be used to show topography (a real-space projection of the coating surface microstructure) and phase-angle changes of the AFM over the sample area to contrast differences in the materials properties.

Infrared (IR) Spectroscopy for In-Vitro Testing

Infrared (IR) Spectroscopy using FTIR, ATR-IR or micro ATR-IR can be used to identify polymer composition by comparison to standard polymer reference spectra.

Example 7: Determination of the Bioabsorbability of a Device

In some embodiments of the device the substrate coated itself is made of a bioabsorbable material, such as the bioabsorbable polymers presented herein, or another bioabsorbable material such as magnesium and, thus, the entire device is bioabsorbable. Techniques presented with respect to showing Bioabsorbability of a polymer coating may be used to additionally and/or alternatively show the bioabsorbability of a device, for example, by GPC In-Vivo testing, HPLC In-Vivo Testing, GPC In-Vitro testing, HPLC In-Vitro Testing, SEM-FIB Testing, Raman Spectroscopy, SEM, and XPS as described herein with variations and adjustments which would be obvious to those skilled in the art. Another technique to view the physical structure of a device in 3-D is Nano X-Ray Computer Tomography (e.g. such as made by SkyScan), which could be used in an elution test and/or bioabsorbability test, as described herein to show the physical structure of the coating remaining on stents at each time point, as compared to a scan prior to elution/bioabsorption.

Example 8: Determination of Secondary Structures Presence of a Biological Agent

Raman Spectroscopy

FT-Raman or confocal raman microscopy can be employed to determine secondary structure of a biological Agent. For example fitting of the Amide I, II, or III regions of the Raman spectrum can elucidate secondary structures (e.g. alpha-helices, beta-sheets). See, for example, Iconomidou, et al., "Secondary Structure of Chorion Proteins of the Teleosetan Fish Dentex dentex by ATR FR-IR and FT-Raman Spectroscopy" *J. of Structural Biology*, 132, 112-122 (2000); Griebenow, et al., "On Protein Denaturation in Aqueous-Organic Mixtures but Not in Pure Organic Solvents" *J. Am. Chem. Soc., Vol* 118, No. 47, 11695-11700 (1996).

Infrared (IR) Spectroscopy for In-Vitro Testing

Infrared spectroscopy, for example FTIR, ATR-IR and micro ATR-IR can be employed to determine secondary structure of a biological Agent. For example fitting of the Amide I, II, of III regions of the infrared spectrum can elucidate secondary structures (e.g. alpha-helices, beta-sheets).

Example 9: Determination of the Microstructure of a Coating on a Medical Device Atomic Force Microscopy (AFM)

AFM is a high resolution surface characterization technique. AFM is used in the art to provide topographical imaging, in addition when employed in Tapping Mode™ can image material and or chemical properties of the surface. Additionally cross-sectioned samples can be analyzed. The technique can be used under ambient, solution, humidified or temperature controlled conditions. Other modes of operation are well known and can be readily employed here by those skilled in the art.

A stent as described herein is obtained. AFM is used to determine the microstructure of the coating. A stent as described herein is obtained. AFM may be employed as described in Ranade et al., "Physical characterization of controlled release of paclitaxel from the TAXUS Express2 drug-eluting stent" *J. Biomed. Mater. Res.* 71(4):625-634 (2004) incorporated herein in its entirety by reference.

For example, polymer and active agent morphologies, coating composition, and physical structure may be determined using atomic force microscopy (AFM) analysis. A multi-mode AFM (Digital Instruments/Veeco Metrology, Santa Barbara, Calif.) controlled with Nanoscope Ma and NanoScope Extender electronics is used. Samples are examined in the dry state using AFM before elution of the active agent. Samples are also examined at select time points through an elution period (e.g. 48 hours) by using an AFM probe-tip and flow-through stage built to permit analysis of wet samples. The wet samples are examined in the presence of the same elution medium used for in-vitro kinetic active agent release analysis (e.g. PBS-Tween20, or 10 mM Tris, 0.4 wt. % SDS, pH 7.4). Saturation of the solution is prevented by frequent exchanges of the release medium with several volumes of fresh medium. TappingMode™ AFM imaging may be used to show topography (a real-space projection of the coating surface microstructure) and phase-angle changes of the AFM over the sample area to contrast differences in the materials properties. The AFM topography images can be three-dimensionally rendered to show the surface of a coated stent, which can show holes or voids of the coating which may occur as the polymer is absorbed and the active agent is released from the polymer over time, for example.

Nano X-Ray Computer Tomography

Another technique that may be used to view the physical structure of a device in 3-D is Nano X-Ray Computer Tomography (e.g. such as made by SkyScan), which could be used in an elution test and/or bioabsorbability test, as described herein to show the physical structure of the coating remaining on stents at each time point, as compared to a scan prior to elution/bioabsorption.

Example 10: Determination of the Extent of Aggregation of an Active Agent

Raman Spectroscopy

Confocal Raman microscopy can be used to characterize the active agent aggregation by mapping in the x-y or x-z direction. Additionally cross-sectioned samples can be analysed. Raman spectroscopy and other analytical techniques such as described in Balss, et al., "Quantitative spatial distribution of sirolimus and polymers in drug-eluting stents using confocal Raman microscopy" *J. of Biomedical Materials Research Part A,* 258-270 (2007), incorporated in its entirety herein by reference, and/or described in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference may be used.

A sample (a coated stent) is prepared as described herein. Images are taken on the coating using Raman Spectroscopy. Alternatively, a coated coupon could be tested in this method. A WITec CRM 200 scanning confocal Raman microscope using a NiYAG laser at 532 nm is applied in the Raman imaging mode. The sample is place upon a piezo-electrically driven table, the laser light is focused upon the sample using a 100× dry objective (numerical aperture 0.90), and the finely focused laser spot is scanned into the sample. As the laser scans the sample, over each 0.33 micron interval a Raman spectrum with high signal to noise is collected using 0.3 Seconds of integration time. Each confocal cross-sectional image of the coatings displays a region 70 μm wide by 10 μm deep, and results from the gathering of 6300 spectra with a total imaging time of 32 min. To deconvolute the spectra and obtain separate images of the active agent and the polymer, all the spectral data (6300 spectra over the entire spectral region 500-3500 $cm^{-1}$) are processed using an augmented classical least squares algorithm (Eigenvector Research, Wenatchee Wash.) using basis spectra obtained from samples of the active agent (in active and inactive form) and polymer. For each sample, several areas are measured by Raman to ensure that results are reproducible, and to show layering of active agent and polymer through the coating. Confocal Raman Spectroscopy can profile down micron by micron, can show the composition of the coating through the thickness of the coating.

Time of Flight Secondary Ion Mass Spectrometry

TOF-SIMS can be used to determine active agent aggregation at the outer 1-2 nm of sample surface when operated under static conditions. The technique can be operated in spectroscopy or imaging mode at high spatial resolution. Additionally cross-sectioned samples can be analysed. When operated under dynamic experimental conditions, known in the art, depth profiling chemical characterization can be achieved.

For example, under static conditions (for example a ToF-SIMS IV (IonToF, Munster)) using a 25 Kv $Bi^{++}$ primary ion source maintained below $10^{12}$ ions per $cm^2$ is used. Where necessary a low energy electron flood gun (0.6 nA DC) is used to charge compensate insulating samples.

Cluster Secondary Ion Mass Spectrometry, may be employed as described in Belu et al., "Three-Dimensional Compositional Analysis of Drug Eluting Stent Coatings Using Cluster Secondary Ion Mass Spectroscopy" *Anal. Chem.* 80: 624-632 (2008) incorporated herein in its entirety by reference.

A stent as described herein is obtained. The stent is prepared for SIMS analysis by cutting it longitudinally and opening it up with tweezers. The stent is then pressed into multiple layers of iridium foil with the outer diameter facing outward.

For example TOF-SIMS experiments are performed on an Ion-TOF IV instrument equipped with both Bi and SF5+ primary ion beam cluster sources. Sputter depth profiling is performed in the dual-beam mode. The analysis source is a pulsed, 25-keV bismuth cluster ion source, which bombarded the surface at an incident angle of 45° to the surface normal. The target current is maintained at ~0.3 pÅ (+10%)

pulsed current with a raster size of 200 um×200 um for all experiments. Both positive and negative secondary ions are extracted from the sample into a reflectron-type time-of-flight mass spectrometer. The secondary ions are then detected by a microchannel plate detector with a post-acceleration energy of 10 kV. A low-energy electron flood gun is utilized for charge neutralization in the analysis mode.

The sputter source used is a 5-keV SF5+ cluster source also operated at an incident angle of 45° to the surface normal. For thin model samples on Si, the SF5+ current is maintained at ~2.7 nA with a 750 um×750 um raster. For the thick samples on coupons and for the samples on stents, the current is maintained at 6 nA with a 500 um×500 um raster. All primary beam currents are measured with a Faraday cup both prior to and after depth profiling.

All depth profiles are acquired in the noninterlaced mode with a 5-ms pause between sputtering and analysis. Each spectrum is averaged over a 7.37 second time period. The analysis is immediately followed by 15 seconds of SF5+ sputtering. For depth profiles of the surface and subsurface regions only, the sputtering time was decreased to 1 second for the 5% active agent sample and 2 seconds for both the 25% and 50% active agent samples.

Temperature-controlled depth profiles are obtained using a variable-temperature stage with Eurotherm Controls temperature controller and IPSG V3.08 software. Samples are first placed into the analysis chamber at room temperature. The samples are brought to the desired temperature under ultra high-vacuum conditions and are allowed to stabilize for 1 minute prior to analysis. All depth profiling experiments are performed at −100 C and 25 C.

Atomic Force Microscopy (AFM)

AFM is a high resolution surface characterization technique. AFM is used in the art to provide topographical imaging, in addition when employed in Tapping Mode™ can image material and or chemical properties for example imaging active agent in an aggregated state. Additionally cross-sectioned samples can be analyzed.

A stent as described herein is obtained. AFM may be employed as described in Ranade et al., "Physical characterization of controlled release of paclitaxel from the TAXUS Express2 drug-eluting stent" *J. Biomed. Mater. Res.* 71(4):625-634 (2004) incorporated herein in its entirety by reference.

Polymer and active agent morphologies, coating composition, at least may be determined using atomic force microscopy (AFM) analysis. A multi-mode AFM (Digital Instruments/Veeco Metrology, Santa Barbara, Calif.) controlled with Nanoscope Ma and NanoScope Extender electronics is used. TappingMode™ AFM imaging may be used to show topography (a real-space projection of the coating surface microstructure) and phase-angle changes of the AFM over the sample area to contrast differences in the materials properties.

Example 11: Preparation of Supercritical Solution Comprising Poly(Lactic-Co-Glycolic Acid) (Plga) in hexafluoropropane A view cell at room temperature (with no applied heat) is pressurized with filtered 1,1,1,2,3,3-Hexafluoropropane until it is full and the pressure reaches 4500 psi. Poly(lactic-co-glycolic acid) (PLGA) is added to the cell for a final concentration of 2 mg/ml. The polymer is stirred to dissolve for one hour. The polymer is fully dissolved when the solution is clear and there are no solids on the walls or windows of the cell.

Example 12: Dry Powder ECM Coating on an Electrically Charged L605 Cobalt Chromium Metal Coupon A 1 cm×2 cm L605 cobalt chromium metal coupon serving as a target substrate for ECM coating is placed in a vessel and attached to a high voltage electrode. Alternatively, the substrate may be a stent or another biomedical device or substrate as described herein, for example. The vessel (V), of approximately 1500 cm$^3$ volume, is equipped with two separate nozzles through which active agent or polymers could be selectively introduced into the vessel. Both nozzles are grounded. Additionally, the vessel (V) is equipped with a separate port was available for purging the vessel. Upstream of one nozzle (D) is a small pressure vessel (PV) approximately 5 cm$^3$ in volume with three ports to be used as inlets and outlets. Each port is equipped with a valve which could be actuated opened or closed. One port, port (1) used as an inlet, is an addition port for the dry powdered active agent. Port (2), also an inlet is used to feed pressurized gas, liquid, or supercritical fluid into PV. Port (3), used as an outlet, is used to connect the pressure vessel (PV) with nozzle (D) contained in the primary vessel (V) with the target coupon.

Dry powdered ECM is loaded into (PV) through port (1) then port (1) is actuated to the closed position. The metal coupon is then charged to +7.5 kV using a Glassman Series EL high-voltage power source. The active agent nozzle on port has a voltage setting of −7.5 kV. After approximately 60-seconds, the ECM is injected and the voltage is eliminated. Upon visual inspection of the coupon using an optical microscope, the entire surface area of the coupon is examined for relatively even distribution of powdered material.

Example 13: Polymer Coating on an Electrically Charged L605 Coupon Using Rapid Expansion from a Liquefied Gas A coating apparatus as described in example 12 above is used in the foregoing example. In this example the second nozzle, nozzle (P), is used to feed precipitated polymer particles into vessel (V) to coat a L605 coupon. Alternatively, the substrate may be a stent or another biomedical device or substrate as described herein, for example. Nozzle (P) is equipped with a heater and controller to minimize heat loss due to the expansion of liquefied gases. Upstream of nozzle (P) is a pressure vessel, (PV2), with approximately 25-cm$^3$ internal volume. The pressure vessel (PV2) is equipped with multiple ports to be used for inlets, outlets, thermocouples, and pressure transducers. Additionally, (PV2) is equipped with a heater and a temperature controller. Each port is connected to the appropriate valves, metering valves, pressure regulators, or plugs to ensure adequate control of material into and out of the pressure vessel (PV2). One outlet from (PV2) is connected to a metering valve through pressure rated tubing which was then connected to nozzle (P) located in vessel (V). In the experiment, 150 mg of poly(lactic-co-glycolic acid) (PLGA) is added to pressure vessel (PV2). 1,1,1,2,3,3-hexafluoropropane is added to the pressure vessel (PV2) through a valve and inlet. Pressure vessel (PV2) is set at room temperature with no applied heat and the pressure is 4500 psi. Nozzle (P) is heated to 150° C. A 1-cm×2-cm L605 coupon is placed into vessel (V), attached to an electrical lead and heated via a heat block 110° C. Nozzle (P) is attached to ground. The voltage is set on the polymer spray nozzle and an emitter air beaker to a achieve a current greater than or equal to 0.02 mAmps using a Glassman high-voltage power source at which point the metering valve is opened between (PV2) and nozzle (P) in pressure vessel (PV). Polymer dissolved in liquefied gas and is fed at a constant pressure of 200 psig into vessel (V) maintained at atmospheric pressure through nozzle (P) at an approximate rate of 3.0 cm$^3$/min. After approximately 5 seconds, the metering valve is closed discontinuing the polymer-solvent feed. Vessel (V) is Nitrogen gas for 30 seconds to displace the fluorocarbon. After approximately 30 seconds, the metering valve is again opened for a period of approximately 5 seconds and then closed. This cycle is repeated about 4 times. After an additional 1-minute the applied voltage to the coupon was discontinued and the coupon was removed from pressure vessel (V). Upon inspection by optical microscope, a polymer coating is examined for even distribution on all non-masked surfaces of the coupon.

Example 14: Dual Coating of a Metal Coupon with Active Agent (ECM or a Component Thereof) and Poly(Lactic-Co-Glycolic Acid) (PLGA)

An apparatus described in example 12 and further described in example 13 is used in the foregoing example. In preparation for the coating experiment, active agent (e.g. ECM or a component thereof) is added to (PV) through port (1), then port (1) was closed. Next, 150 mg of poly(lactic-co-glycolic acid) (PLGA) is added to pressure vessel (PV2). 1,1,1,2,3,3-hexafluoropropane is added to the pressure vessel (PV2) through a valve and inlet. Pressure vessel (PV2) is kept at room temperature with no applied heat with the pressure inside the isolated vessel (PV2) approximately 4500 psi. Nozzle (P) is heated to 150° CA 1-cm×2-cm L605 coupon is added to vessel (V) and connected to a high-voltage power lead. Both nozzles (D) and (P) are grounded. To begin, the coupon is charged to +7.5 kV after which port (3) connecting (PV) containing active agent to nozzle (D) charged at −7.5 kV is opened allowing ejection of the active agent into vessel (V) maintained at ambient pressure. Alternatively, the substrate may be a stent or another biomedical device or another substrate as described herein, for example. After closing port (3) and approximately 60-seconds, the metering valve connecting (PV2) with nozzle (P) inside vessel (V) is opened allowing for expansion of liquefied gas to a gas phase and introduction of precipitated polymer particles into vessel (V) while maintaining vessel (V) at ambient pressure. After approximately 15 seconds at a feed rate of approximately 3 cm$^3$/min., the metering valve s closed while the coupon remained charged. The sequential addition of active agent followed by polymer as described above is optionally repeated to increase the number of active agent-polymer layers after which the applied potential is removed from the coupon and the coupon was removed from the vessel. The coupon is then examined using an optical microscope to determine whether a consistent coating is visible on all surfaces of the coupon except where the coupon was masked by the electrical lead.

Example 15: Dual Coating of a Metal Coupon with Active Agent (ECM or a Component Thereof) and Poly(Lactic-Co-Glycolic Acid) (PLGA) Followed by Supercritical Hexafluoropropane Sintering After inspection of the coupon created in example 14, the coated coupon (or other coated substrate, e.g. coated stent) is carefully placed in a sintering vessel that is at a temperature of 75° C. 1,1,1,2,3,3-hexafluoropropane in a separate vessel at 75 psi is slowly added to the sintering chamber to achieve a pressure of 23 to 27 psi. This hexafluoropropane sintering process is done to enhance the physical properties of the film on the coupon. The coupon remains in the vessel under these conditions for approximately 10 min after which the supercritical hexafluoropropane is slowly vented from the pressure vessel and then the coupon was removed and reexamined under an optical microscope. The coating is observed in conformal, consistent, and semi-transparent properties as opposed to the coating observed and reported in example 14 without dense hexafluoropropane treatment.

Example 16: Coating of a Metal Cardiovascular Stent with Active Agent (ECM or a Component Thereof) and Poly(Lactic-Co-Glycolic Acid) (PLGA)

The apparatus described in examples 13, 14 and 15 is used in the foregoing example. The metal stent used is made from cobalt chromium alloy of a nominal size of 18 mm in length with struts of 63 microns in thickness measuring from an albuminal surface to a luminal surface, or measuring from a side wall to a side wall. The stent is coated in an alternating fashion whereby the first coating layer of active agent is followed by a layer of polymer. These two steps, called a active agent/polymer cycle, are repeated twice so there are six layers in an orientation of active agent-polymer-active agent-polymer-active agent-polymer. After completion of each polymer coating step and prior the application of the next active agent coating step, the stent is first removed from the vessel (V) and placed in a small pressure vessel where it is exposed to supercritical hexafluoropropane as described above in example 15.

Example 17: Coating of Stent with ECM (or a Component Thereof) and Poly(Lactic-Co-Glycolic Acid) (PLGA)

ECM (or a component thereof) is obtained. 50:50 PLGA (Mw=~90) are purchased from Aldrich Chemicals. Eurocor CoCr (7cell) stents are used. The stents are coated by dry electrostatic capture followed by supercritical fluid sintering, using 3 stents/coating run and 3 runs/data set. Analysis of the coated stents is performed by multiple techniques on both stents and coupons with relevant control experiments described herein.

In this example, PLGA is dissolved in 1,1,1,2,3,3-Hexafluoropropane with the following conditions: a) room temperature, with no applied heat; b) 4500 psi; and c) at 2 mg/ml concentration. The spray line is set at 4500 psi, 150° C. and nozzle temperature at 150° C. The solvent (Hexafluoropropane) is rapidly vaporized when coming out of the nozzle (at 150° C.). A negative voltage is set on the polymer spray nozzle to achieve a current of greater than or equal to 0.02 mAmps. The stent is loaded and polymer is sprayed for 15 seconds to create a first polymer coating.

The stent is then transferred to a sintering chamber that is at 75° C. The solvent, in this example 1,1,2,3,3-hexafluoropropane, slowly enters the sintering chamber to create a pressure at 23 to 27 psi. Stents are sintered at this pressure for 10 minutes.

The ECM (or a component thereof) is loaded into the Active agent injection port (Active agent injection port). The injection pressure is set at 280 psi with +7.5 kV for the stent holder and −7.5 kV for the active agent injection nozzle.

After the voltage is set for 60 s, the active agent (ECM or a component thereof) is injected into the chamber to create a first active agent coating.

A second polymer coating is applied with two 15 second sprays of dissolved polymer with the above first polymer coating conditions. The second coating is also subsequently sintered in the same manner.

A second ECM (or component thereof) coating is applied with the same parameters as the first active agent (ECM or a component thereof) coating. Lastly, the outer polymer layer is applied with three 15 second sprays of dissolved polymer with the above polymer coating conditions and subsequently sintered.

Example 18: Fully Bioabsorbable Stent Comprising ECM (or a Component Thereof) in the Coating ECM (or a component thereof) is obtained. A bioabsorbable polymer is obtained, for non-limiting example, 50:50 PLGA (Mw=~90) purchased from Aldrich Chemicals. A bioabsorbable substrate is formed in a stent shape and comprises a metal-oxide metal (such as magnesium oxide). The substrate is then coated by dry electrostatic capture followed by supercritical fluid sintering, using 3 stents/coating run and 3 runs/data set. Analysis of the coated stents is performed by multiple techniques on both stents and coupons with relevant control experiments described herein.

In this example, PLGA is dissolved in 1,1,1,2,3,3-Hexafluoropropane with the following conditions: a) room temperature, with no applied heat; b) 4500 psi; and c) at 2 mg/ml concentration. The spray line is set at 4500 psi, 150° C. and nozzle temperature at 150° C. The solvent (Hexafluoropropane) is rapidly vaporized when coming out of the nozzle (at 150° C.). A negative voltage is set on the polymer spray nozzle to achieve a current of greater than or equal to 0.02 mAmps. The substrate is loaded and polymer is sprayed for 15 seconds to create a first polymer coating.

The substrate is then transferred to a sintering chamber that is at 75° C. The solvent, in this example 1,1,2,3,3-hexafluoropropane, slowly enters the sintering chamber to create a pressure at 23 to 27 psi. Stents are sintered at this pressure for 10 minutes.

The ECM (or a component thereof) is loaded into the Active agent injection port (Active agent injection port). The injection pressure is set at 280 psi with +7.5 kV for the stent holder and −7.5 kV for the active agent injection nozzle. After the voltage is set for 60 s, the active agent (ECM or a component thereof) is injected into the chamber to create a first active agent coating.

A second polymer coating is applied with two 15 second sprays of dissolved polymer with the above first polymer coating conditions. The second coating is also subsequently sintered in the same manner.

A second ECM (or component thereof) coating is applied with the same parameters as the first active agent (ECM or a component thereof) coating. Lastly, the outer polymer layer is applied with three 15 second sprays of dissolved polymer with the above polymer coating conditions and subsequently sintered.

Example 19: Fully Bioabsorbable Stent Comprising ECM (or a Component Thereof) in the Coating ECM (or a component thereof) is obtained. A first polymer is obtained, for non-limiting example, a bioabsorbable polymer that absorbs by surface erosion. A bioabsorbable substrate is formed in a stent shape and comprises a second polymer (for non-limiting example, 50:50 PLGA (Mw=~90) which erodes by bulk erosion). The substrate is then coated by dry electrostatic capture followed by supercritical fluid sintering, using 3 stents/coating run and 3 runs/data set. Analysis of the coated stents is performed by multiple techniques on both stents and coupons with relevant control experiments described herein.

In this example, the first polymer is dissolved in an appropriate solvent according to methods described throughout this disclosure, using an RESS or eRESS and/or a DPC or eDPC process. The substrate is loaded and the first polymer is sprayed for 15 seconds to create a first polymer coating.

The substrate may, in some embodiments, be transferred to a sintering chamber that is at 75° C. The solvent slowly enters the sintering chamber to create a pressure at 15 to 40 psi. Stents are sintered at this pressure for 5-30 minutes.

The ECM (or a component thereof) is loaded into the Active agent injection port (Active agent injection port). The injection pressure is set at 280 psi with +7.5 kV for the stent holder and −7.5 kV for the active agent injection nozzle, or another pressure that is appropriate for the particular component. After the voltage is set for 60 s, the active agent (ECM or a component thereof) is injected into the chamber to create a first active agent coating.

A second coating is applied with two 15 second sprays of dissolved first polymer with the above polymer coating conditions. The second coating may also subsequently sintered in the same manner.

A second ECM (or component thereof) coating is applied with the same or similarly appropriate parameters as the first active agent (ECM or a component thereof) coating. Lastly, the outer polymer layer is applied with three 15 second sprays of dissolved first polymer with the above polymer coating conditions and subsequently sintered.

Figure 4:
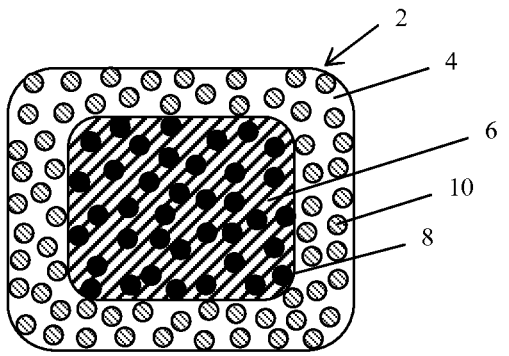
FIG. 4 depicts a cross sectional view of a device according to an embodiment herein, for non-limiting example, a stent strut, the device comprising a substrate comprising ECM or at least one ECM component coated with a polymer and a pharmaceutical agent.

Example 20: Fully Bioabsorbable Stent Comprising ECM (or a Component Thereof) in the Core of the Stent A bioabsorbable substrate is formed in a stent shape. The substrate comprises a first polymer (for non-limiting example, 50:50 PLGA (Mw=~90) which erodes by bulk erosion) and ECM (or a component thereof). The substrate may be formed, for example, by coating a column or patterned shape tube using a coating method such as described in the examples or description provided herein, using ECM as the active agent, and using the desired bioabsorbable substrate polymer having the features of interest in the particular embodiment. Following substrate formation, the substrate may be coated with a second polymer (which may be bioabsorbable at a different rate or by a different mode, or may be the same polymer as the first polymer). The substrate may also and/or alternatively be coated with another active agent, such as a pharmaceutical agent. For non-limiting example, coating methods described in Examples 16-17, at least, may be used wherein the ECM coating step is replaced with a pharmaceutical agent coating step having similar or the same coating parameters as noted therein. A device created in this manner is depicted in FIG. 4, showing a cross sectional view of a device according to an embodiment herein. FIG. 4 depicts, for non-limiting example, a stent strut. The device of FIG. 4 depicts a substrate 6 comprising ECM 8 or at least one ECM component, wherein the substrate 6 is coated with a coating 2 comprising polymer 4 and a pharmaceutical agent 10. The substrate 6 of FIG. 4 further comprises a bioabsorbable polymer. A device created in this manner can provide the extended temporal healing benefits of ECM released to the target tissue in a controlled manner. For example, wherein the coating is comprised of a polymer that erodes by surface erosion, ECM present only in the substrate is not released into the target tissue until the substrate itself is exposed, at a lag as compared to the release of the pharmaceutical or other agent in the coating. Other combinations of release profiles may be contemplated by the combinations of various bioabsorbable polymers having different elution modes, thicknesses, and other properties, as well as the combinations of active agents, whether pharmaceutical or biologic, along with the presence in the device of the ECM for promoted healing and restoration of tissue function.

Example 21: Device Comprising ECM (or a Component Thereof), that Returns Endothelial Function Devices created in the examples above or according to disclosure noted here and elsewhere in this description may restore endothelial function at the location of delivery (target tissue) at least one of: 28 days, 30 days, 45 days, 60 days, 90 days, and 180 days. The return of endothelial function may be determined in any of a number of ways. That is, use of ECM in a device, whether ECM or a component thereof alone or used in conjunction with another therapeutic agent (another biologic agent or pharmaceutical agent) in the device may be used to restore endothelial function at the location of delivery following implantation of the device.

For non-limiting example, although vessels visualized by SEM at 28 days following implantation of a stent—particularly a drug-coated stent, may show complete endothelialization, the function of that endothelial tissue may not be restored. However, a stent comprising ECM, or at least one component thereof, can restore this endothelial function at 28 days, at least.

Return of endothelial tissue function can be shown by Rapid Atrial Pacing testing as described in Hamilos et al. JACC Vol. 51, No. 22, 2008, Endothelium and DES Jun. 3, 2008:2123-9 incorporated herein in its entirety by reference. Restored endothelial function can also and/or alternatively be shown in animal studies which determine endothelial function by acetylcholine challenge (ACH) testing by determining the presence of Nitric Oxide (NO). Normal vessels dilate in response to exercise or acetylcholine (ACH). The dilation response is dependent on the endothelial production of NO (Nitric Oxide). In contrast, atherosclerotic vessels are characterized by having endothelial dysfunction and constrict in response to exercise or ACH. This is explained by either a loss of endothelial cells or loss of eNOS expression and NO production. Thus, despite 100% endothelialization as determined by immunohistochemistry or by SEM, a vessel may not have full endothelial function. Endothelial function, thus, may be shown by evidence of eNOS staining by immunohistochemistry, or by presence of eNOS (endothelial Nitric Oxide Synthase) mRNA expression as determined by RT-PCR. eNOS protein level may alternatively be detected by Western blot analysis tested in an animal model to determine restored endothelial function.

As used herein, the term "about," unless otherwise defined for the aspect to which it refers, means variations of any of 0.01%, 0.05%, 0.1%, 0.5%, 1%, 2%, 5%, 10%, 15%, 20%, 25%, 30%, and 50% on either side of the aspect target or on a single side of the aspect target, depending on the embodiment. When referring to an aspect that is expressed as a percent, the term about does not generally refer to a percent of the percent, but rather a range about the percent—unless otherwise stated. For non-limiting example, if an aspect was "about 5.0%" and the variation for about was 0.5% (depending on the embodiment), this could mean 5.0% plus or minus 0.5%—equating to a range of 4.5% to 5.5%.

The foregoing is illustrative of the present invention, and is not to be construed as limiting thereof. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A device comprising
a substrate; and
a coating on said substrate comprising a first polymer and an active agent, wherein the active agent comprises a macrolide immunosuppressive drug in crystalline form and an extracellular matrix, wherein the extracellular matrix comprises an interlocking mesh of fibrous proteins and glycosaminoglycans (GAGs).

2. The device of claim 1, wherein the extracellular matrix comprises an extracellular matrix component comprising at least one of: heparin sulfate, choindroitin sulfate, keratan sulfate, hayaluronic acid, collagen, elastin, fibronectin, laminin, merosin, tenascin, vitronectin, and fibrillin.

3. The device of claim 1, wherein the substrate is at least one of a stent, an angioplasty balloon and a cutting balloon.

4. The device of claim 1, wherein the first polymer is at least one of: a bioabsorbable polymer and a durable polymer.

5. The device of claim 1, wherein substantially all of the active agent remains within said coating and on said substrate until the implantable device is deployed at an intervention site inside the body of a subject, wherein upon deployment of said device in the body of said subject a portion of the active agent is delivered at said intervention site along with at least a portion of said polymer, and wherein the device is adapted to be delivered to a body lumen.

6. The device of claim 1, wherein active agent particles are sequestered or encapsulated within a microstructure.

7. The device of claim 1, wherein the coating is formed on said substrate through a process comprising depositing said polymer active agent by an e-RESS, an e-SEDS, or an e-DPC process.

8. The device of claim 1, wherein the coating comprises a plurality of layers a first layer comprises the first polymer, a second layer comprises the active agent, a third layer comprises a second polymer, a fourth layer comprises the active agent, and a fifth layer comprises a third polymer.

9. The device of claim 8, wherein at least two of said first polymer, said second polymer and said third polymer are the same polymer.

10. A stent delivery system comprising:
an elongate member having an inflation lumen and a guidewire lumen therein;
a balloon having an interior that is in fluid communication with the inflation lumen; and a coated stent mounted on the balloon, wherein the coated stent comprises a stent and a plurality of layers that form a coating on said stent;

wherein at least one of said layers comprises a polymer and at least one of said layers comprises an active agent, wherein the active agent comprises a macrolide immunosuppressive drug in crystalline form and an extracellular matrix, wherein the extracellular matrix comprises an interlocking mesh of fibrous proteins and glycosaminoglycans (GAGs).

11. A bioabsorbable device comprising
a bioabsorbable substrate comprising a first active agent; and
a coating on said substrate wherein the coating comprises a first polymer,
wherein the first active agent comprises a macrolide immunosuppressive drug in crystalline form and an extracellular matrix, wherein the extracellular matrix comprises an interlocking mesh of fibrous proteins and glycosaminoglycans (GAGs).

12. A bioabsorbable device comprising
a bioabsorbable substrate; and
a coating on said substrate wherein the coating comprises a first polymer, a first active agent and a second active agent, wherein the first active agent comprises extracellular matrix, the extracellular matrix comprises an interlocking mesh of fibrous proteins and glycosaminoglycans (GAGs), and the second active agent comprises a macrolide immunosuppressive drug in crystalline form.

13. The device of one of claims 11 and 12, wherein the bioabsorbable substrate comprises at least one of a bioabsorbable metal framework and a second polymer, wherein the second polymer is bioabsorbable.

14. The device of one of claims 11 and 12, wherein the first polymer degrades by at least one of bulk erosion and surface erosion.

15. The device of one of claims 11 and 12, wherein the device is delivered to a target tissue and returns endothelial function to the target tissue at 28 days from device delivery.

\* \* \* \* \*